(12) United States Patent
Su et al.

(10) Patent No.: US 10,259,846 B2
(45) Date of Patent: *Apr. 16, 2019

(54) BOUVARDIN DERIVATIVES AND THERAPEUTIC USES THEREOF

(71) Applicants: The Regents of the University of Colorado, a body corporate, Denver, CO (US); Suvica, Inc., Menlo Park, CA (US)

(72) Inventors: Tin Tin Su, Boulder, CO (US); Mara N. Gladstone, Boulder, CO (US); Gan Zhang, Niwot, CO (US); Tarek Sammakia, Boulder, CO (US)

(73) Assignees: The Regents of the University of Colorado, Denver, CO (US); Suvica, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/233,167

(22) Filed: Aug. 10, 2016

(65) Prior Publication Data

US 2017/0218025 A1     Aug. 3, 2017

Related U.S. Application Data

(63) Continuation of application No. 14/380,361, filed as application No. PCT/US2013/027200 on Feb. 21, 2013, now Pat. No. 9,452,215.

(60) Provisional application No. 61/702,706, filed on Sep. 18, 2012, provisional application No. 61/601,981, filed on Feb. 22, 2012.

(51) Int. Cl.
| | |
|---|---|
| *A61N 5/10* | (2006.01) |
| *C07K 7/06* | (2006.01) |
| *C07K 7/64* | (2006.01) |
| *A61K 38/00* | (2006.01) |
| *A61K 38/12* | (2006.01) |
| *A61K 45/06* | (2006.01) |
| *A61K 31/704* | (2006.01) |
| *C07K 14/415* | (2006.01) |

(52) U.S. Cl.
CPC ............. *C07K 7/64* (2013.01); *A61K 31/704* (2013.01); *A61K 38/12* (2013.01); *A61K 45/06* (2013.01); *A61N 5/10* (2013.01); *C07K 7/06* (2013.01); *C07K 14/415* (2013.01); *A61K 38/00* (2013.01); *A61N 2005/1098* (2013.01)

(58) Field of Classification Search
None
See application file for complete search history.

(56) References Cited

U.S. PATENT DOCUMENTS

| | | |
|---|---|---|
| 4,226,856 A | 10/1980 | Cole |
| 4,476,299 A | 10/1984 | Itokawa |
| 4,725,578 A | 2/1988 | Itokawa |
| 4,992,445 A | 2/1991 | Lawter et al. |
| 5,001,139 A | 3/1991 | Lawter et al. |
| 5,023,252 A | 6/1991 | Hseih |
| 5,741,772 A | 4/1998 | Chang |
| 5,861,510 A | 1/1999 | Piscopio et al. |
| 5,863,949 A | 1/1999 | Robinson et al. |
| 7,358,262 B2 | 4/2008 | Stockwell |
| 7,645,881 B2 | 1/2010 | Karp et al. |
| 7,695,899 B2 | 4/2010 | Su et al. |
| 9,452,215 B2 | 9/2016 | Su et al. |
| 2002/0051767 A1 | 5/2002 | Chiang et al. |
| 2005/0123906 A1 | 6/2005 | Rana |
| 2005/0226378 A1 | 10/2005 | Cocks et al. |
| 2006/0276527 A1 | 12/2006 | Tidmarsh |
| 2008/0299220 A1 | 12/2008 | Tamarkin et al. |
| 2009/0118362 A1 | 5/2009 | Pelletier et al. |
| 2014/0057844 A1 | 2/2014 | Su et al. |
| 2015/0238562 A1 | 8/2015 | Su et al. |
| 2015/0343016 A1 | 12/2015 | Su et al. |

FOREIGN PATENT DOCUMENTS

| | | |
|---|---|---|
| EP | 0606046 A1 | 7/1994 |
| EP | 0780386 A1 | 6/1997 |
| EP | 0818442 A2 | 1/1998 |
| EP | 0931788 A2 | 7/1999 |
| EP | 0945864 A2 | 9/1999 |
| EP | 1004578 A2 | 5/2000 |
| WO | WO-9005719 A1 | 5/1990 |
| WO | WO-9627583 A1 | 9/1996 |
| WO | WO-9633172 A1 | 10/1996 |
| WO | WO-9803516 A1 | 1/1998 |
| WO | WO-9807697 A1 | 2/1998 |
| WO | WO-9830566 A1 | 7/1998 |
| WO | WO-9833768 A1 | 8/1998 |

(Continued)

OTHER PUBLICATIONS

Office action dated Jun. 16, 2017 for U.S. Appl. No. 14/582,981.
Office Action dated Dec. 15, 2017 for U.S. Appl. No. 14/582,981.
Alice guidance with respect to 35 USC 101, Jun. 2014.
Anderson, et al. Handbook of Clinical Drug Data, Tenth Edition, McGraw-Hill, 2002.
"Arnal, et al. How does taxol stabilize microtubules? Curr Biol. Aug. 1, 1995;5(8):900-8."
"Bigot, et al. Total Synthesis of an Antitumor Agent RA-VII via an Efficient Preparation of Cycloisodityrosine. J. Org. Chem. 1999, 64, 6283-6296."
Boger, et al. Design, synthesis and evaluation of bouvardin, deoxybouvardin and RA-I-XIV pharmacophore analogs. Bioorg Med Chem. Feb. 1994;2(2):85-100.

(Continued)

*Primary Examiner* — Christina Bradley
(74) *Attorney, Agent, or Firm* — Wilson Sonsini Goodrich & Rosati

(57) ABSTRACT

The present invention is directed at bouvardin analogs arid related compounds for the treatment of disorders including cancer. Provided herein are bouvardin analogs and related compounds, pharmaceutical compositions and kits comprising at least one bouvardin analog or related compound, and methods for treating disorders including cancer. In some aspects the compounds inhibit translation elongation at the ribosome. The compounds are used in combination with radiation therapy or with known chemotherapeutic compositions.

24 Claims, 40 Drawing Sheets

(56) References Cited

FOREIGN PATENT DOCUMENTS

| WO | WO-9834915 A1 | 8/1998 |
|---|---|---|
| WO | WO-9834918 A1 | 8/1998 |
| WO | WO-9907675 A1 | 2/1999 |
| WO | WO-9929667 A1 | 6/1999 |
| WO | WO-9952889 A1 | 10/1999 |
| WO | WO-9952910 A1 | 10/1999 |
| WO | WO-2004045532 A2 | 6/2004 |
| WO | WO-2011130677 A1 | 10/2011 |
| WO | WO-2012075472 A2 | 6/2012 |
| WO | WO-2012075472 A3 | 10/2012 |
| WO | WO-2013126617 A1 | 8/2013 |

OTHER PUBLICATIONS

Boger, et al. Key analogues of the tetrapeptide subunit of RA-VII and deoxybouvardin. Bioorg Med Chem. Oct. 1996;4(10):1597-603.
Boger, et al. N-Desmethyl Derivatives of Deoxybouvardin and RA-VII: Synthesis and Evaluation. J. Am. Chem. Soc. 1995; 117(28):7364-7378.
"Boger, et al. Synthesis of (9R,12S)- and (9S,12S)-Cycloisodityrosine and Their N-Methyl Derivatives. J. Org. Chem. 1997, 62, 2054-2069."
Boger, et al. Synthesis of n29-desmethyl ra-vii. Identifiation of the pharmacophore of ra-1=vii and deoxybouvardin and reassignment of the subunit functional roles. J. Org. Chem. (1992) 57(5) p. 1319-1321.
Boger, et al. Total Synthesis of Bouvardin, O-Methylbouvardin, and O-Methyl-N9-desmethylbouvardin. J. Am. Chem. Soc., 1994, 116 (19), pp. 8544-8556.
Chemocare.com page on nitrogen mustard, available online at https://web.archive.org/web/20121105000248/http://chemocare.com/chemotherapy/drug-info/Nitrogen-Mustard.aspx on Nov. 5, 2012.
"Chitnis, et al. Reversal of natural resistance to bouvardin (NSC 259968) in sarcoma 180 cells in vitro and in vivo by verapamil. J Cancer Res Clin Oncol. 1985;110(3):221-4."
Choy. Combining taxanes with radiation for solid tumors. Int J Cancer. Jun. 20, 2000;90(3):113-27.
Dancey, J. mTOR signaling and drug development in cancer. Nature reviews. Clinical oncology, 2010. 7(4): p. 209-19.
Ding, et al. Ribosome dysfunction is an early event in Alzheimer's disease. J Neurosci. Oct. 5, 2005;25(40):9171-5.
Dolma, et al. Identification of genotype-selective antitumor agents using synthetic lethal chemical screening in engineered human tumor cells. Cancer Cell, 2003. 3(3): p. 285-96.
"Duan, et al. Inhibition of ABCB1 (MDR1) and ABCB4 (MDR3) expression by small interfering RNA and reversal of paclitaxel resistance in human ovarian cancer cells. Mol Cancer Ther. Jul. 2004;3(7):833-8."
Edwards, et al. Combinatorial effect of maytansinol and radiation in Drosophila and human cancer cells. Dis Model Mech, 2011. 4(4): p. 496-503.
European search report and opinion dated Jun. 19, 2015 for EP Application No. 13826711.7.
Fannon. Bouvardin Analogs. The University of Arizona, Master Thesis 1986. http://hdl.handle.net/10150/291590.
Field, JB. Clinical Evaluation of Streptovitacin A. Cancer Chemother Rep, 1963. 31: p. 53-9.
Fleming, et al. Nitrile-containing pharmaceuticals: efficacious roles of the nitrile pharmacophore. J Med Chem. Nov. 25, 2010;53(22):7902-17. doi: 10.1021/jm100762r. Epub Aug. 30, 2010.
Gandin, et al. Eukaryotic initiation factor 6 is rate-limiting in translation, growth and transformation. Nature, 2008. 455(7213): p. 684-8.
Gladstone, et al. A translation inhibitor identified in a Drosophila screen enhances the effect of ionizing radiation and taxol in mammalian models of cancer. Dis Model Mech, 2012. in press.

Goodman, et al. The Pharmacological Basis of Therapeutics, Tenth Edition, McGraw Hill, 2001.
Guigay, et al. Nasopharyngeal carcinoma and therapeutic management: the place of chemotherapy. Ann Oncol. Sep. 2006;17 Suppl 10:x304-7.
"Hasuda, et al. Synthesis of [Tyr-5-1P(CH2NMe)-Tyr-6]RA-VII, a reduced peptide bond analogue of RA-VII, an antitumor bicyclic hexapeptide. Bioorganic & Medicinal Chemistry Letters 22 (2012) 2757-2759."
Hilliard, et al. Translational regulation of autoimmune inflammation and lymphoma genesis by programmed cell death 4. J Immunol. Dec. 1, 2006;177(11):8095-102.
"Hitotsuyanagi, et al. Aza-cycloisodityrosine analogue of RA-VII, an antitumor bicyclic hexapeptide. Bioorganic & Medicinal Chemistry Letters, 23 (2013) 6728-6731."
Hitotsuyanagi, et al. Isolation, structural elucidation, and synthesis of RA-XVII, a novel bicyclic hexapeptide from Rubia cordifolia, and the effect of side chain at residue 1 upon the conformation and cytotoxic activity. Tetrahedron Letters. 2004; 45:935-938.
Hitotsuyanagi, et al. Novel water-soluble analogues retaining potent antitumor activity of RA-VII, a cyclic hexapeptide from Rubia plants. Bioorganic & Medicinal Chemistry Letters. 1997; 7(24):3125-3128.
Hitotsuyanagi, et al. Per-N-methylated analogues of an antitumor bicyclic hexapeptide RA-VII. Bioorg Med Chem. Apr. 1, 2011;19(7):2458-63. doi: 10.1016/j.bmc.2011.02.003. Epub Mar. 5, 2011.
Hitotsuyanagi, et al. RA-dimer A, a novel dimeric antitumor bicyclic hexapeptide from Rubia cordifolia L. Tetrahedron Letters. 2000; 41(32):6127-6130.
Hitotsuyanagi, et al. Studies on Rubia akane(RA) derivatives. Part 8. Design, syntheses and antitumour activity of cyclic hexapeptide RA analogues possessing an alkyl substituent on the Tyr-3 aromatic ring. J. Chem. Soc., Perkin Trans. 1. 1996:213-217.
Hitotsuyanagi, et al. Synthesis of [Gly-1]RA-VII, [Gly-2]RA-VII, and [Gly-4]RA-VII. Glycine-containing analogues of RA-VII, an antitumor bicyclic hexapeptide from Rubia plants. J Org Chem. Mar. 5, 2004;69(5):1481-6.
Howard Hughes medical center webpage. "Understanding cancer diversity." available online at http://www.hhmi.org/biointeractive/understandingcancerdiversity, downloaded Jun. 21, 2016.
Hudis. Trastuzumab—mechanism of action and use in clinical practice. N Engl J Med. Jul. 5, 2007;357(1):39-51.
International search report and written opinion dated Jul. 11, 2012 for PCT/US2011/063192.
International search report and written opinion dated Jul. 12, 2013 for PCT Application No. US2013/027200.
Itokawa, et al. Studies on antitumor cyclic hexapeptides RA obtained from Rubiae Radix, Rubiaceae. III. On derivatives of RA-V and their in vivo activities. Chem Pharm Bull (Tokyo). Aug. 1984;32(8):3216-26.
Jaklevic, et al. Contribution of growth and cell cycle checkpoints to radiation survival in Drosophila. Genetics, 2006. 174(4): p. 1963-72.
Jeffes, et al. Actinic keratosis. Current treatment options. Am J Clin Dermatol. May-Jun. 2000;1(3):167-79.
Jeremic, et al. Radiation therapy alone or with concurrent low dose daily either cisplatin or carboplatin in locally advanced unresectable squamous cell carcinoma of the head and neck: a prospective randomized trial. Radiation and Oncology (1997) 43 p. 29-37.
"Jia, et al. Mechanisms of drug combinations: interaction and network perspectives. Nat Rev Drug Discov. Feb. 2009;8(2):111-28. doi: 10.1038/nrd2683."
Jimenez, et al. Novel inhibitors of translation in eukaryotic systems. Antibiotics (1986) 6 p. 248-254.
Katzung, Ed. Basic and Clinical Pharmacology, Ninth Edition, McGraw Hill, 2004.
Le Tourneau, et al. Dose escalation methods in phase I clinical trials. J. Natl. Cancer Inst. (2009) 101 p. 708-720.
Lee, et al. A novel bicyclic hexapeptide, RA-XVIII, from Rubia cordifolia: structure, semi-synthesis, and cytotoxicity. Bioorg Med Chem Lett. Jan. 15, 2008;18(2):808-11. Epub Nov. 17, 2007.

(56) References Cited

OTHER PUBLICATIONS

Martindale. The Extra Pharmacopoeia, Thirty-Second Edition, The Pharmaceutical Press, London, 1999.
Moore. Management of metastatic pancreatic cancer: current strategies and future directions. Cancerworld. 2011; 40:448.
Myriad-Mayo guidance with respect to 35 USC 101, Mar. 2014.
Notice of allowance dated May 19, 2016 for U.S. Appl. No. 14/380,361.
"Office action dated Jan. 5, 2016 for U.S. Appl. No. 14/582,981."
Office action dated Jul. 27, 2015 for U.S. Appl. No. 14/380,361.
Office action dated Jul. 29, 2016 for U.S. Appl. No. 14/582,981.
Office action dated Sep. 2, 2014 for U.S. Appl. No. 13/988,501.
"Orina, et al. Evaluation of current methods used to analyze the expression profiles of ATP-binding cassette transporters yields an improved drug-discovery database. Mol Cancer Ther. Jul. 2009;8(7):2057-66. doi: 10.1158/1535-7163.MCT-09-0256. Epub Jul. 7, 2009."
Park, et al. Integrative analysis of proteomic signatures, mutations, and drug responsiveness in the NCI 60 cancer cell line set. Molecular cancer therapeutics, 2010. 9(2): p. 257-67.
Patani, et al. Bioisosterism: A Rational Approach in Drug Design. Chem Rev. Dec. 19, 1996;96(8):3147-3176.
Pratt, et al. Principles of Drug Action, Third Edition, Churchill Livingston, New York, 1990.
Remington's Pharmaceutical Sciences, 20th Ed., Lippincott Williams & Wilkins, 2000.
Robert, et al. Altering chemosensitivity by modulating translation elongation. PLoS One. 2009;4(5):e5428. doi: 10.1371/journal.pone. 0005428. Epub May 1, 2009.
Ruggero, et al. The translation factor eIF-4E promotes tumor formation and cooperates with c-Myc in lymphomagenesis. Nat Med, 2004. 10(5): p. 484-6.
Sacco, et al. The average body surface area of adult cancer patients in the uk: a multicentre restrospective study. PLoS ONE (2010) 5(1) e8933.
Shi, et al. When translation meets metabolism: multiple links to diabetes. Endocr Rev. Feb. 2003;24(1):91-101.
Silvera, et al. Essential role for eIF4GI overexpression in the pathogenesis of inflammatory breast cancer. Nat Cell Biol, 2009. 11(7): p. 903-8.
Silvera, et al. Translational control in cancer. Nat Rev Cancer, 2010. 10(4): p. 254-66.
Song, et al. Defining the optimal dose of radiation in leukemic patients with extramedullary lesions. BMC Cancer. Oct. 6, 2011;11:428. doi: 10.1186/1471-2407-11-428.
The Jan. 10, 2014 post in the blog "in the pipeline," http://pipeline.corante.com/archives/2014/01/10/a_new_look_at_clinical_attrition.php.
The Jun. 9, 2014 entry in the blog "in the pipeline" http://pipeline.corante.com/archives/2014/06/09/good_news_our_alzheimers_drug_didnt_work.php.
Tobey, et al. Effects of Bouvardin (NSC 259968), a cyclic hexapeptide from Bouvardia ternifolia, on the progression capacity of cultured Chinese hamster. Cancer Res. Dec. 1978;38(12):4415-21.
Walpole, et al. The weight of nations: an estimation of adult human biomass. BMC public health (2012) 12(439) p. 1-6.
Zalacain, et al. The mode of action of the antitumor drug bouvardin, an inhibitor of protein synthesis in eukaryotic cells. FEBS Lett. (1982) 148(1) p. 95-97.
Zhang, et al. Nuclear factor-kappaB inhibition by parthenolide potentiates the efficacy of Taxol in non-small cell lung cancer in vitro and in vivo. Mol Cancer Res. Jul. 2009;7(7):1139-49. doi: 10.1158/1541-7786.MCR-08-0410. Epub Jul. 7, 2009.
EP17204487.7 Extended Search Report dated Apr. 17, 2018.
EP13751205.9 Extended Search Report dated Jun. 19, 2015.

| | IC50 on cancer cell lines, in micro M | | | | | | |
|---|---|---|---|---|---|---|---|
| | lung | HNC | | melanoma | | | |
| Compound | H157 | Det562 | FaDu | WM35 | A375 | 1205Lu | HS294T |
| N-2-9H-RA VII | 0.473 | ND | 0.249 | ND | ND | ND | ND |
| *meta* Br-N-29-H-RA VII | 0.383 | ND | 0.137 | 1.304 | 0.827 | 0.42 | 0.062 |
| *meta* CN-N-29-H-RA VII | 7 | 0.682 | 0.514 | ND | ND | ND | ND |
| *meta* Cl-N-29-H-RA VII | 0.940 | 0.398 | 0.452 | 7.683 | 8.360 | 0.773 | 1.126 |
| N-29-H-Tyr-Fl-RA VII | >10 | ~10 | ~80 | >10 | >10 | ~10 | >10 |

| PLX4032 BRAF inhibitor | FA (+/- 5) | FA50 (average) | FA50 (range) | FA75 (average) | FA75 (range) | FA90 (average) | FA 90 (range) | FA >95 (average) |
|---|---|---|---|---|---|---|---|---|
| | A375 | All Fas above 75 | | | | 0.687 | 0.342-1.276 | none |
| | 1205Lu | none | none | 0.423 | 0.345-0.64 | 1.49 | 0.544-3.77 | none |
| | HS294T | 0.354 | 0.32-0.385 | 0.357 | 0.266-0.481 | 0.875 | 0.22-1.421 | 0.708 |

| TAK-333 MEK Inhibitor | FA(+/-5) | FA50 (average) | FA50 (range) | FA75 (average) | FA75 (range) | FA90 (average) | FA90 (range) | FA>95 (average) | FA>95 (range) |
|---|---|---|---|---|---|---|---|---|---|
| | WM35 | 1.137 | 1.137 | 0.892 | 0.816-0.968 | 2.2 | 0.889-5.161 | 1.743 | 1.254-2.213 |
| | A375 | 4.23 | 2.111-5.705 | 0.48 | 0.093-1.076 | 0.71 | 0.223-1.353 | 0.234 | 0.071-0.417 |
| | 1205Lu | 0.6765 | 0.57-0.783 | 1.024 | 0.953-2.139 | 0.8354 | 0.59-1.093 | 0.218 | 0.084-0.457 |
| | HS294T | 1.087 | 1.087 | 0.7665 | 0.693-0.84 | 2.49 | 0.296-3.202 | 2.19 | 1.76-2.979 |

| PF-04691502 PI3K/TOR dual inhibitor | FA(+/-5) | FA50 (average) | FA50 (range) | FA75 (average) | FA75 (range) | FA90 (average) | FA90 (range) | FA>95 (average) | FA>95 (range) |
|---|---|---|---|---|---|---|---|---|---|
| | WM35 | 0.852 | 0.710-1.01 | 0.823 | 0.766-0.92 | 0.717 | 0.424-1.217 | 0.7 | 0.163-1.432 |
| | A375 | 0.778 | 0.778 | 0.11 | 0.102-0.124 | 0.725 | 0.149-1.849 | 0.565 | 0.339-0.793 |
| | 1205Lu | 1.08 | 1.08 | 0.338 | 0.209-0.588 | 1.208 | 0.241-2.288 | 0.599 | 0.313-1.344 |
| | HS294T | 1.274 | 1.274 | 0.537 | 0.537 | 0.336 | 0.225-0.417 | 0.943 | 0.287-1.589 |

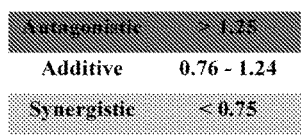

| Antagonistic | >1.25 |
| Additive | 0.76 - 1.24 |
| Synergistic | <0.75 |

FIGURE 22

BOUVARDIN DERIVATIVES AND THERAPEUTIC USES THEREOF

CROSS REFERENCE

This application is a continuation of U.S. patent application Ser. No. 14/380,361 filed Aug. 21, 2014, which is a National Phase Entry of International Application No. PCT/US2013/027200 filed Feb. 21, 2013, which claims the benefit of U.S. Provisional Application No. 61/702,706 filed Sep. 18, 2012 and U.S. Provisional Application No. 61/601,981 filed Feb. 22, 2012, each of which is incorporated herein by reference in its entirety.

BACKGROUND OF THE INVENTION

Cancer is a leading cause of death worldwide and US. It is estimated that 1 in 4 deaths in US is due to cancer. Current cancer therapies target every aspect of cancer cell growth and division except translation of RNA into protein by the ribosome. Increased ribosome activity and protein translation however, is a hallmark of cancer cells and is required for disease progression.

The ribosome is not typically a target for cancer therapy. While ribosome activity and protein translation can be regulated by blocking the elongation step of translation at the ribososome using "anti-ribosomals," these anti-ribosomals have been omitted from cancer therapies as a result of two strong, long-standing biases. First, translation inhibitors are thought to lack the specificity required to target cancer cells. Second, translation inhibitors are thought to be too toxic to be used as therapeutics. For example, Tobey et al. concluded that bouvardin, a translation inhibitor, " . . . does not appear to possess the type of properties normally associated with a useful chemotherapeutic agent" (Tobey et al., CANCER RESEARCH 38, 4415-4421, December 1978). Currently, there is only one FDA-approved anticancer agent that targets the ribosome (homoharringtonine, approved for chronic myeloid leukemia on Oct. 26, 2012). No agents approved for the treatment of solid tumors target the ribosome.

There is a need in the art to develop new cancer therapeutics which target ribosome activity and protein translation for the treatment of cancer.

SUMMARY OF THE INVENTION

The present invention relates to a compound according to Formula I-III, methods of treating disorders including cancer by administrating a compound according to Formula I-III, and pharmaceutical compositions and kits containing a compound according to Formula I-III,

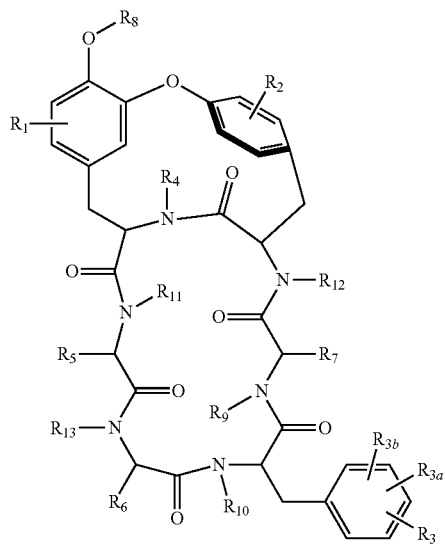

(I)

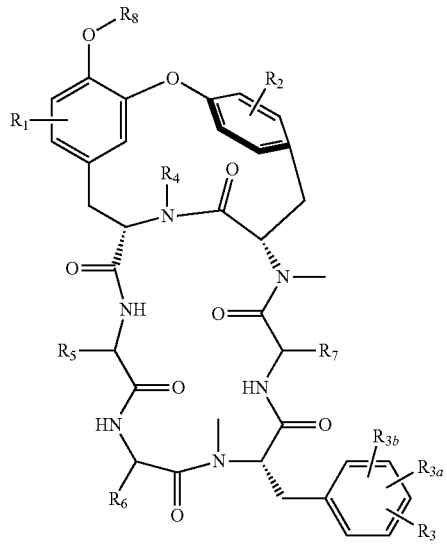

(II)

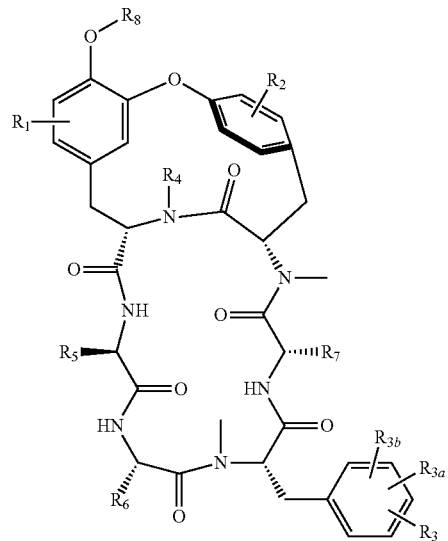

(III)

Wherein:

$R_1$, $R_2$, $R_3$, $R_{3a}$ and $R_{3b}$ are independently selected from the group consisting of H, halogen, hydroxyl, $C_{1-8}$ alkyl, $C_{1-8}$ haloalkyl, heteroalkyl, $C_{3-8}$ cycloalkyl, amino, cyano, nitro, aryl, heteroaryl, aminoacyl and acylamino;

$R_4$ is selected from the group consisting of H, $C_{1-8}$ alkyl, $C_{1-8}$ haloalkyl, $C_{3-8}$ cycloalkyl, heteroalkyl, aryl and heteroaryl;

$R_5$, $R_6$ and $R_7$ are independently selected from the group consisting of H, $C_{1-8}$ alkyl, $C_{1-8}$ haloalkyl, heteroalkyl, $C_{3-8}$ cycloalkyl, alkyl carboxylic acid, alkylaryl, alkylheteroaryl, aryl and heteroaryl;

$R_8$, $R_9$, $R_{10}$, $R_{11}$, $R_{12}$ and $R_{11}$ are independently selected from the group consisting of H, $C_{1-8}$ alkyl, heteroalkyl, aryl, heteroaryl, $C_{1-8}$ haloalkyl and $C_{3-8}$ cycloalkyl; or a pharmaceutically acceptable salt thereof.

In some aspects, compounds of the present invention are not selected from natural products RA-I, RA-II, RA-III, RA-IV, deoxybouvardin(RA-V), RA-VII, RA-VIII, RA-X, RA-XI, RA-XII, RA-XIII and compounds listed in Scheme 1.

Scheme 1

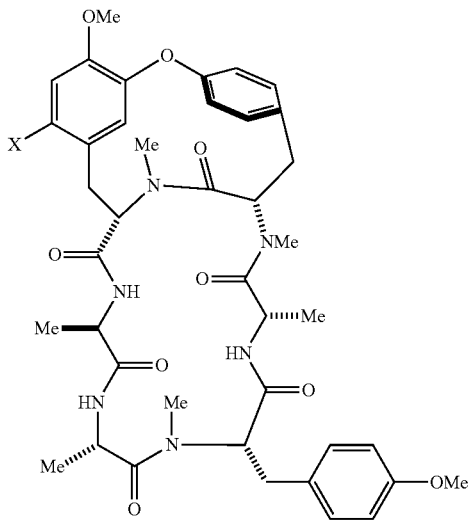

X = NO$_2$, NH$_2$, OH

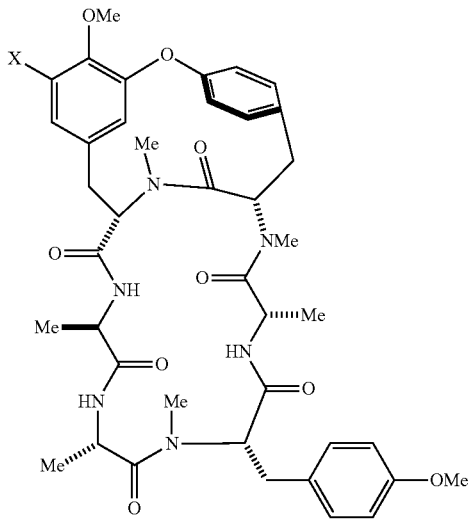

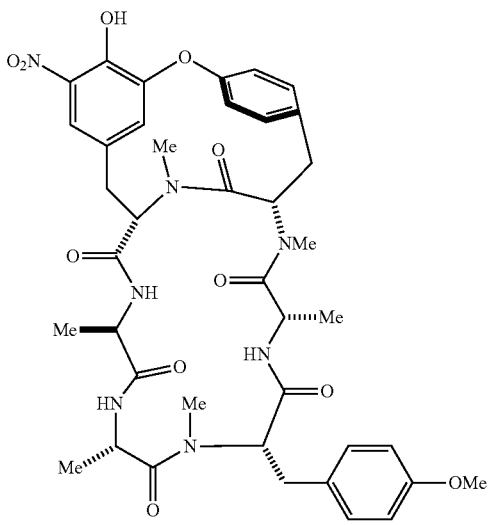

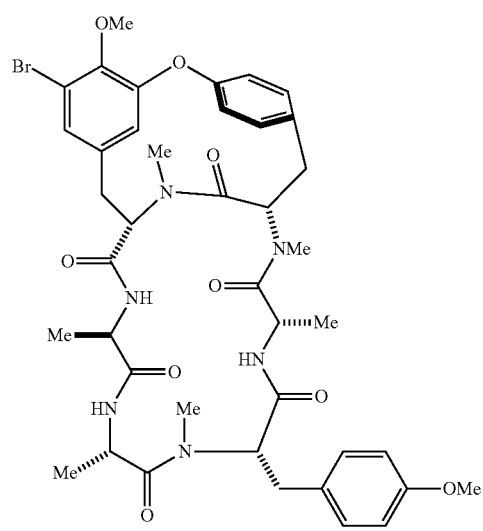

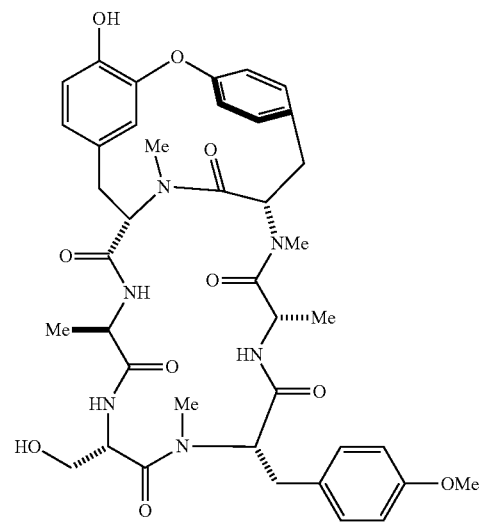

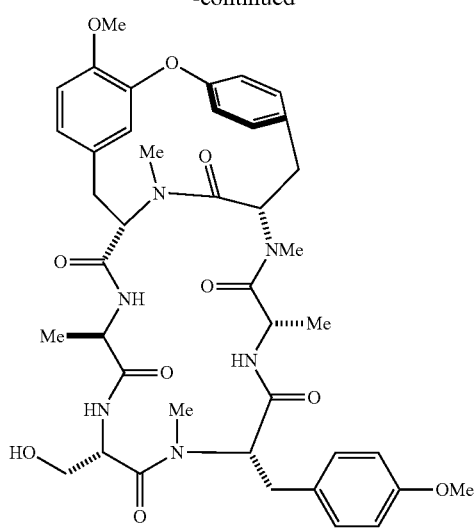
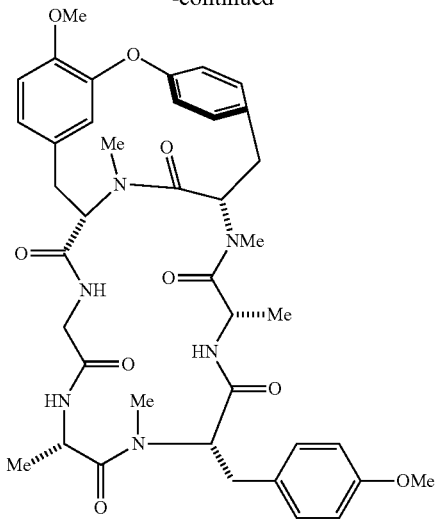
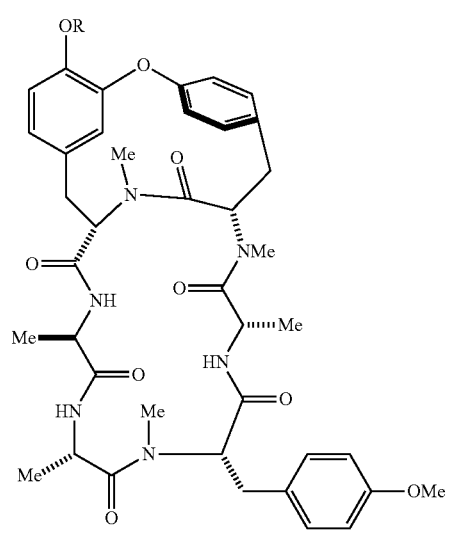
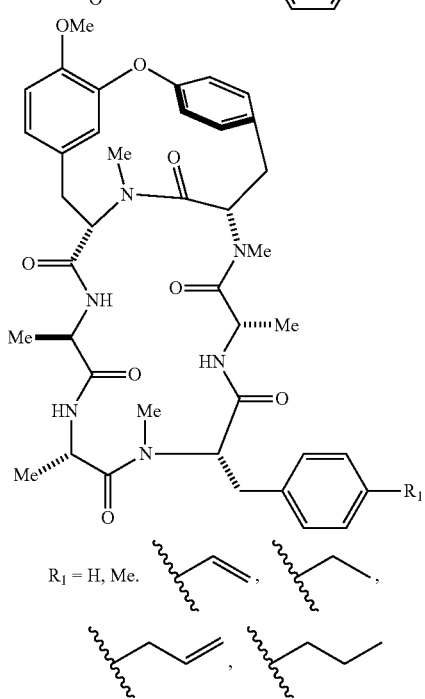
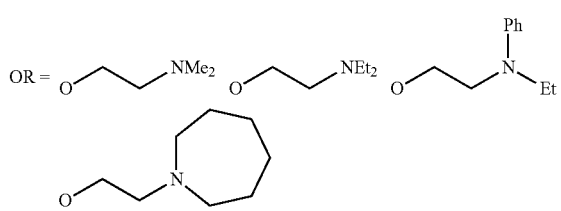
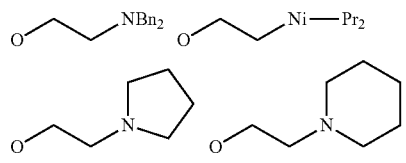
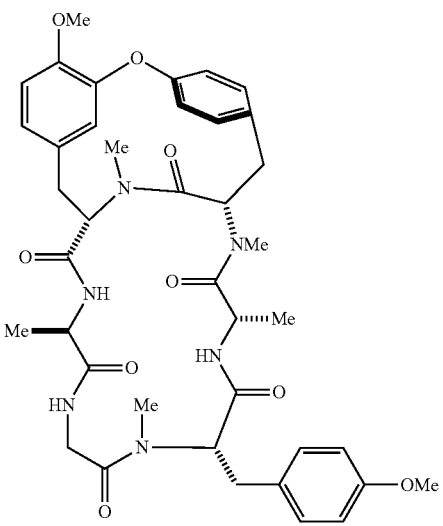

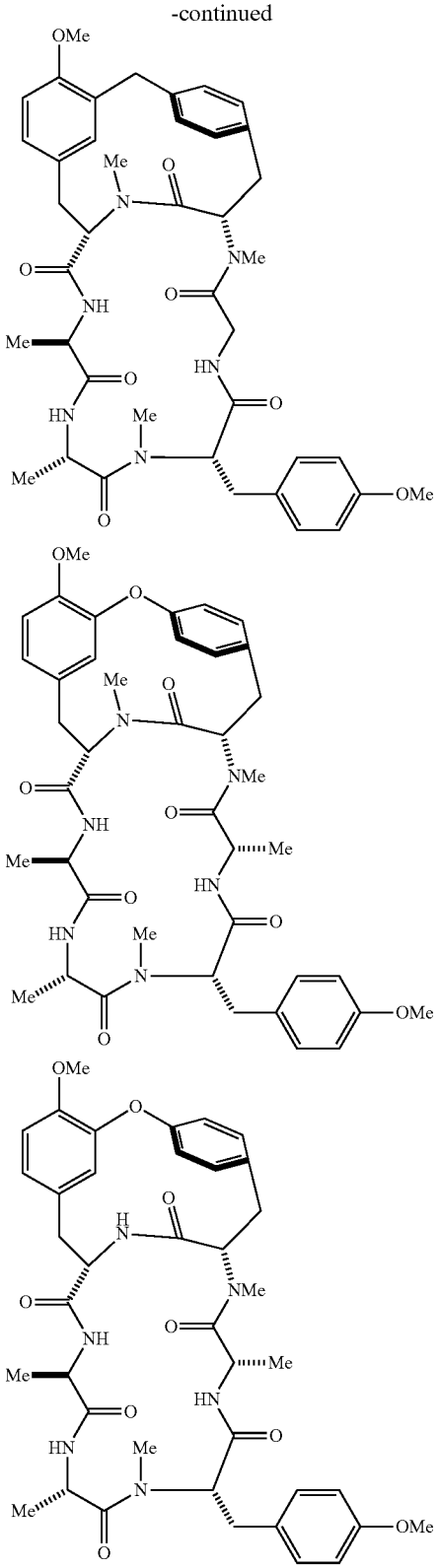

In some aspects, compounds of the present invention are protein-translation inhibitors. In one aspect, the disorders comprise cancer. In another aspect, the disorders comprise an immune disorder. In yet another aspect, the disorders comprise diabetes. In yet another aspect, the disorders comprise a neurological disorder. The disorders may be associated with abnormal protein accumulation and production.

In some aspects, the invention provides methods of inhibiting the activity of a ribosome comprising contacting the ribosome with an effective amount of a compound according to Formula I-III. The methods are useful for treating disorders including cancer in a subject, for example, without being limiting, head and neck cancer, melanoma, blood cancers, lymphatic cancer, central nervous system cancer, immune disorder, diabetes and a neurological disorder associated with abnormal protein accumulation.

In some aspects, the invention provides methods of treating cancer in a subject in need of such treatment comprising administering to a mammal in need thereof a therapeutically effective amount of a compound according to Formula I-III and a second therapeutic agent. In some embodiments, the compound inhibits protein translation. In some embodiments, the second therapeutic agent comprises a chemotherapeutic composition. In some further embodiments, the chemotherapeutic composition comprises a taxane, a platinum-based chemotherapy drug, doxorubicin or a doxorubicin derivative or combination thereof.

In some aspects, the invention provides methods for treating cancer in a subject comprising administering to the subject an effective amount of a compound according to Formula I-III, and an effective amount of radiation therapy. In some embodiments, the compound inhibits protein translation. If desired, the radiation therapy is given at a dosage of 20 Gy to 80 Gy total, fractionated into smaller doses over a course of treatment that may last several weeks.

In some aspects, the invention provides kits comprising an agent and instructions regarding radiation therapy for a human patient in need of radiation treatment. In some embodiments, the agent is selected from compounds according to Formula I-III.

In some aspects, the invention provides pharmaceutical compositions for treating disorders including cancer comprising a therapeutic effective amount of a compound according to Formula I-II, in admixture with at least one pharmaceutically acceptable carrier or diluents.

In one aspect, the invention provides compounds and methods for treating cancer comprising administering to the subject a compound selected from the following:

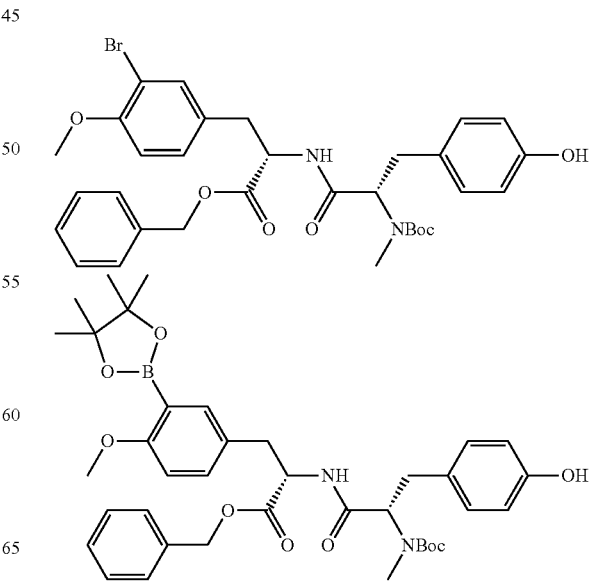

-continued

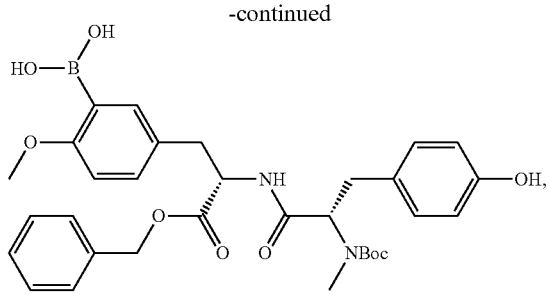

and pharmaceutically acceptable salts thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 22 depicts that meta Br-N-29-H RA-VII synergizes with the inhibitors of BRAF, MEK and P13K/TOR.

DETAILED DESCRIPTION OF THE INVENTION

Figure 1:
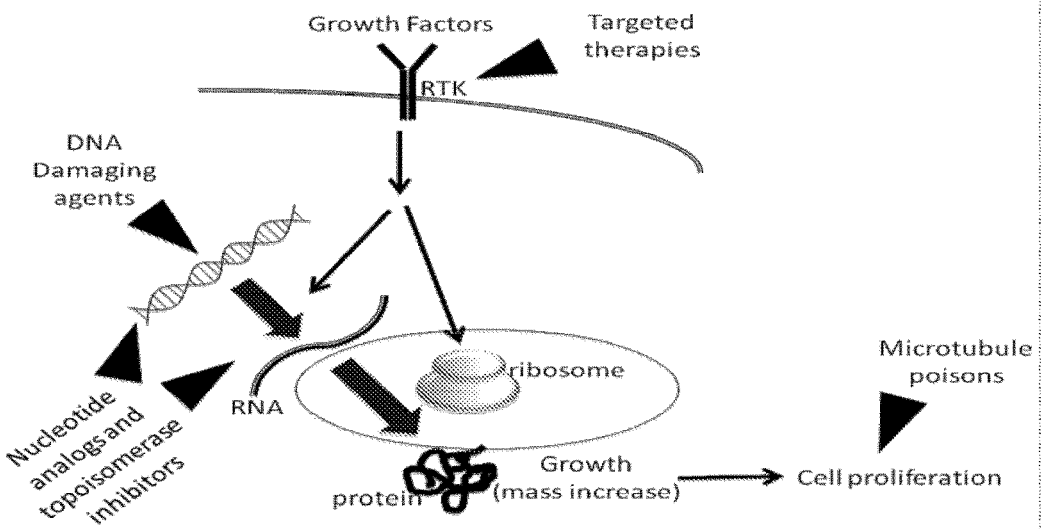
FIG. 1 depicts current targets for cancer therapies (arrowheads). Current therapies target steps from growth factor signaling to cell division, with the exception of the ribosome.
Figure 2:
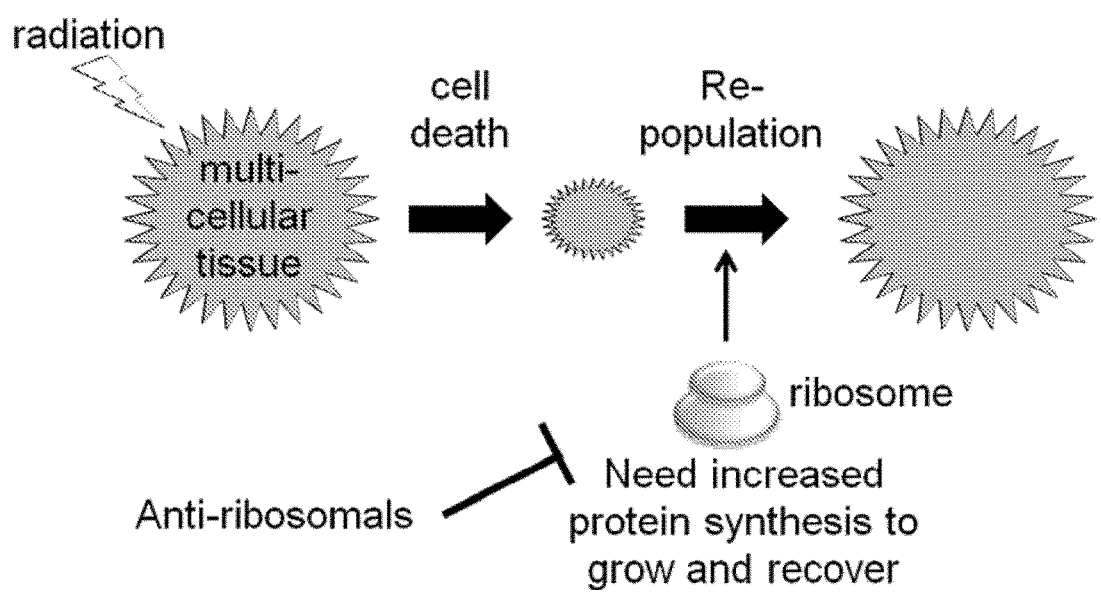
FIG. 2 depicts one rationale for why inhibition of protein synthesis enhances radiation therapy. Radiation kills cells and shrinks tumors but survivors can proliferate to repopulate the tumor.

The present invention is directed at bouvardin analogs and related compounds for the treatment of disorders including cancer. Provided herein are bouvardin analogs and related compounds, pharmaceutical compositions and kits comprising at least one bouvardin analog or related compound, and methods for treating disorders including cancer. Without being bound by theory, some of the compounds of the present invention may act as protein-translation inhibitors, which can be used as a target area for the treatment of disorders including cancer. Compounds of the present invention may be used alone or combine effectively with standard treatments for treating disorders including cancer. The use of protein translational inhibitors for the treatment of disorders including cancer has been described in PCT/US11/63192, which is hereby incorporated by reference in its entirety.

Scheme 2. Bouvardin

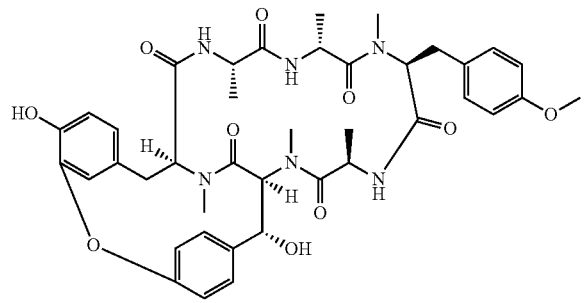

General Considerations

Unless otherwise stated, structures depicted herein are also meant to include compounds that differ by the presence of one or more isotopically enriched atoms. For example, compounds having the present structures except for the replacement of a hydrogen by a deuterium, tritium, or the replacement of a carbon by 13C- or 14C-enriched carbon are within scope of this invention. The compounds of the present invention may also contain unnatural portions of atomic isotopes at one or more of atoms that constitute such compounds. For example, the compounds may be radiolabeled with radioactive isotopes, such as for example tritium, iodine-125, and carbon-14. All isotopic variations of the compounds of the present invention, whether radioactive or not, are encompassed within the scope of the present invention.

When a carbon has four different groups attached to it, the carbon is stereogenic. If the stereochemistry of a stereogenic carbon is not specified, the stereochemistry is meant to include both stereoisomers. Therefore, if a chemical structure has two stereogenic centers and both stereogenic centers are not specified, the structure meant to encompass all four possible stereoisomers providing there is no C2 symmetry within the structure.

Where substituent groups are specified by their conventional chemical formulae, written from left to right, they equally encompass the chemically identical substituents that would result from writing the structure from right to left, e.g., —CH$_2$O— is equivalent to —OCH$_2$—.

When ranges are used herein for physical properties, such as molecular weight, or chemical properties, such as chemical formulae, all combinations and sub combinations of ranges and specific embodiments therein are intended to be included. The term "about" when referring to a number or a numerical range means that the number or numerical range referred to is an approximation within experimental variability (or within statistical experimental error), and thus the number or numerical range may vary, for example, between 1% and 15% of the stated number or numerical range.

Definitions

The following abbreviation and terms have the indicated meanings throughout.

The term "alkyl" as used herein means a branched or unbranched saturated hydrocarbon chain. "C$_{1-8}$ alkyl" has the same meaning but only have from 1-8 total saturated carbons. Examples of C$_{1-8}$ alkyl include, but are not limited to, methyl, ethyl, propyl, i-propyl, n-butyl, i-butyl, t-butyl, pentyl, i-pentyl, neopentyl, and the like.

The term "cycloalkyl" as used herein means a saturated carbocyclic ring. "C$_{3-8}$ cycloalkyl" means a 3-membered to 8-membered carbocyclic ring system. The numbers 3 and 8 denote the size of the ring system. The cycloalkyl may be optionally substituted with at least one group selected from the following: alkyl, halogen, hydroxyl and amino.

The term "halogen" means F, Cl, Br or I.

The term "alkyl radical" means the resulting product after removing a hydrogen radical from a saturated alkane.

The term "haloalkyl" means an alkyl radical as defined above, wherein at least one hydrogen atom is replaced with a halogen. "C$_{1-8}$ haloalkyl" has the same meaning but only have from 1-8 total saturated carbons. The point of attachment of haloalkyl is through a carbon atom. Representative examples of C$_{1-8}$ haloalkyl include, but are not limited to, CF$_3$, CH$_2$CF$_3$, CH$_2$CH$_2$CF$_3$, and the like.

The term "aryl" means an aromatic carbocyclic moiety such as phenyl and naphthyl.

The term "heteroaryl" means an aromatic heterocyclic ring of 5 to 10 members and having at least one heteroatom selected from nitrogen, oxygen and sulfur, and containing at least 1 carbon atom, including both mono- and bicyclic ring systems. Representative heteroaryls are pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, and quinazolinyl.

The term "alkyl carboxylic acid" means an alkyl radical as defined above, wherein at least one hydrogen atom is replaced with a carboxylic acid (COOH) group. The point of attachment of alkyl carboxylic acid is through a carbon atom. Representative examples include, but are not limited to —CH$_2$CH$_2$COOH, —CH$_2$COOH, —CH$_2$CH(COOH) CH$_3$, and the like.

The term "alkylaryl" means an alkyl radical as defined above, wherein at least one hydrogen atom is replaced with an aryl ring. The aryl ring may be optionally substituted with at least one substituent selected from nitro, cyano, hydroxyl, alkyl, heteroalkyl, amino, alkylamino and halogen. The point of attachment of alkylaryl is through a carbon atom. Representative examples include, but are not limited to the following (the dotted line denotes the point of attachment):

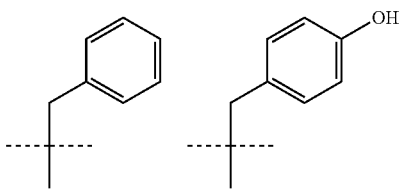

The term "alkylheteroaryl" means an alkyl radical as defined above, wherein at least one hydrogen atom is replaced with a heteroaryl ring. The heteroaryl ring may be optionally substituted with at least one substituent selected from nitro, cyano, hydroxyl, alkyl, heteroalkyl, amino, alkylamino and halogen. The point of attachment of alkylheteroaryl is through a carbon atom. Representative examples include, but are not limited to the following:

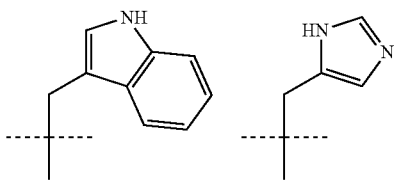

The term "heteroalkyl" means an alkyl radical as defined above wherein one carbon atom is replaced with a substituent independent selected from the group consisting of —OR$^a$, —NR$^b$R$^c$, and —S(O)$_n$R$^d$, wherein n is an integer from 0-2 and with the understanding that the point of attachment of heteroalkyl is through a carbon atom. R$^a$ is selected from hydrogen, acyl, alkyl, cycloalkyl, or cycloalkylalkyl; R$^b$ and R$^c$ are independently selected from hydrogen, acyl, alkyl, cycloalkyl; and when n is 0, R$^d$ is selected hydrogen, alkyl, cycloalkyl, and when n is 1 or 2, R$^d$ is alkyl, cycloalkyl, amino, or acylamino. Representative examples include, but are not limited to, 2-hydroxyethyl, thiomethyl, methylthioethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl,

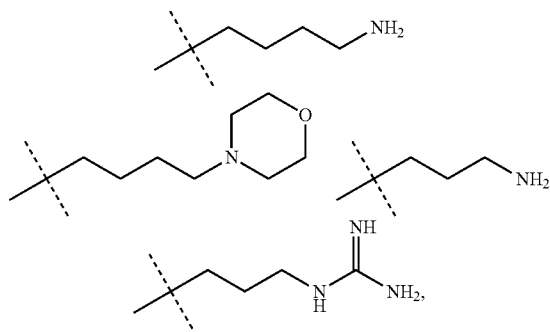

and the like.

The term "alkylamino" means an alkyl radical as defined above wherein one carbon atom is replaced with —NR$^b$R$^c$, wherein R$^b$ and R$^c$ are independently selected from hydrogen, acyl, alkyl, cycloalkyl with the understanding that the point of attachment of alkylamino is through a carbon atom.

The term "aminoacyl" means a group of formula —NR$^e$C(=O)R$^f$, wherein R$^e$ and R$^f$ are independently selected from H, alkyl, aryl or heteroaryl.

The term "acylamino" means a group of formula —C(=O)$^N$R$^e$R$^f$ wherein R$^e$ and R$^f$ are independently selected from H, alkyl, aryl or heteroaryl.

The term "amino" means —NR$^g$R$^h$ or

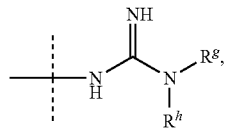

wherein R$^g$ and R$^h$ are independently selected from H, alkyl, heteroalkyl, alkanol, aryl or heteroaryl. R$^g$ and R$^h$ may optionally link to form a heterocycle. The point of attachment of amino is through the nitrogen atom. Representative examples include, but are not limited to the following:

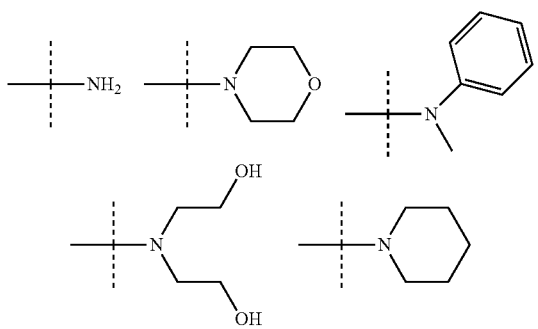

The term "acyl" means a functional group —C(=O)R$^i$, wherein R$^i$ is selected from alkyl, cycloalkyl, heteroakyl, aryl and heteroaryl.

The term "cyano" as used herein refers to a carbon linked to a nitrogen by a triple bond, i.e., —C≡N. The term "nitro" as used herein refers to an NO$_2$ substituent.

Chemical entities include compounds of Formula I, Formula II or Formula III family, and all pharmaceutically acceptable forms thereof. Pharmaceutically acceptable forms of the compounds recited herein include pharmaceutically acceptable salts, chelates, non-covalent complexes, prodrugs, and mixtures thereof. In certain embodiments, the compounds described herein are in the form of pharmaceutically acceptable salts. Hence, the terms "chemical entity" and "chemical entities" also encompass pharmaceutically acceptable salts, chelates, non-covalent complexes, prodrugs, and mixtures.

"Pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

"Pharmaceutically acceptable salt" refers to salts that retain the biological effectiveness and properties of the compounds described herein and, which are not biologically or otherwise undesirable. In many cases, the compounds described herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

"Solvate" refers to a compound (e.g., a compound selected from Formula I or a pharmaceutically acceptable salt thereof) in physical association with one or more molecules of a pharmaceutically acceptable solvent. It will be understood that "a compound of Formula I" encompasses the compound of Formula I and solvates of the compound, as well as mixtures thereof.

A "therapeutic effect," as that term is used herein, encompasses a therapeutic benefit and/or a prophylactic benefit. A prophylactic effect includes delaying or eliminating the appearance of a disease or condition, delaying or eliminating the onset of symptoms of a disease or condition, slowing, halting, or reversing the progression of a disease or condition, or any combination thereof.

"Therapeutically effective amount" or "effective amount" refers to that amount of a compound selected from Formula I, Formula II, or Formula III family, that is sufficient to effect a certain action, such as treatment, as defined below, when administered to a mammal in need of such treatment; modulating the catalytic activity of the ribosome, such as when administered to an environment where modulation of the catalytic activity of a ribosome is desired; or disrupting the function of a ribosome, such as when administered to an environment where disrupting the function of a ribosome is desired. The therapeutically effective amount will vary depending upon the subject and disease condition being treated, the weight and age of the subject, the severity of the disease condition, the particular compound selected from Formula I, Formula II, or Formula III family, the dosing regimen to be followed, timing of administration, the manner of administration and the like, all of which can readily be determined by one of ordinary skill in the art.

Compounds of Formula I, Formula II or Formula III family also include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof. "Crystalline form," "polymorph," and "novel form" may be used interchangeably herein, and are meant to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

In addition, if a compound is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

As noted above, prodrugs also fall within the scope of chemical entities, for example, ester or amide derivatives of the compounds selected from Formula I, Formula II or Formula III. The term "prodrug" includes any compound that becomes a compound of Formula I or Formula II when administered to a patient, e.g., upon metabolic processing of the prodrug. Examples of prodrugs include, but are not limited to, acetate, formate, benzoate, and like derivatives of functional groups (such as alcohol or amine groups) in the compounds selected from Formula I. Formula II or Formula III family.

The term "chelate" refers to the chemical entity formed by the coordination of a compound to a metal ion at two (or more) points.

The term "non-covalent complex" refers to the chemical entity formed by the interaction of a compound and another molecule wherein a covalent bond is not formed between the compound and the molecule. For example, complexation can occur through van der Waals interactions, hydrogen bonding, and electrostatic interactions (also called ionic bonding).

The term "active agent" is used to indicate a chemical entity which has biological activity. In certain embodiments, an "active agent" is a compound having pharmaceutical utility.

The term "subject" refers to an animal, such as a mammal, for example a human that has been or will be the object of treatment, observation or experiment. The methods described herein can be useful in both human therapy and veterinary applications. In some embodiments, the patient is a mammal, and in some embodiments, the patient is human.

The term "treatment" or "treating" means any treatment of a disease in a patient, including: preventing the disease, that is, causing the clinical symptoms of the disease not to develop; inhibiting the disease; slowing or arresting the development of clinical symptoms; and/or relieving the disease, that is, causing the regression of clinical symptoms.

The term "selective inhibition" or "selectively inhibit" as referred to a biologically active agent refers to the agent's ability to preferentially reduce the target signaling activity as compared to off-target signaling activity, via direct or interact interaction with the target.

Compounds and Preparation

Bouvardin belongs to a class of antitumor bicyclic hexapeptide. Many members have been isolated and their biological activities have been studied (see Ji-Ean Lee Yukio Hitotsuyanagi, Ik-Hwi Kim, Tomoyo Hasuda and Koichi Takeya, *Biorganic & Medicinal Chemistry Letters* 2008, 18, 808-811; Yukio Hitotsuyanagi, Tomoyo Hasuda, Takayuki Aihara, Hirishi Ishikawa, Kentaro Yamaguchi, Hideji Itikawa and Koichi Takeya, *Journal of Organic Chemistry* 2004, 69, 1481-1486; Dale L. Boger and Jiacheng Zhou, *J. Am. Chem. Soc.* 1995, 117, 7364-7368; Dale L. Boger and Jiacheng Zhou, *Bioorganic & Medicinal Chemistry* 1996, 4, 1597-1603, and are herein incorporated by reference in their entirety).

In one aspect of the present invention, there is provided a compound according to Formula I, wherein $R_1$, $R_2$, $R_3$, $R_{3a}$, $R_{3b}$, $R_4$, $R_5$, $R_6$, $R_7$, $R_8$, $R_9$, $R_{10}$, $R_{11}$, and $R_{12}$ are defined in the Summary of the Invention, with the proviso that the compound is not selected from natural products RA-I, RA-II, RA-III, RA-IV, deoxybouvardin(RA-V), RA-VII, RA-VIII, RA-X, RA-XI, RA-XII, RA-XIII and compounds listed in Scheme 1. In other embodiments provided below, substituents present in each embodiment which are not explicitly defined within the scope of the embodiment retain the broadest definition defined in the Summary of the Invention.

In one aspect of the present invention, there is provided a compound according to Formula II, Wherein $R_1$, $R_2$, $R_3$, $R_{3a}$ and $R_{3b}$ are independently selected from the group consisting of H, halogen, hydroxyl, $C_{1-8}$ alkyl, $C_{1-8}$ haloalkyl, heteroalkyl, $C_{3-8}$ cycloalkyl amino, cyano, nitro, aryl, heteroaryl, aminoacyl and acylamino; $R_4$ is selected from the group consisting of H, $C_{1-8}$ alkyl, $C_{1-8}$ haloalkyl, $C_{3-8}$ cycloalkyl, heteroalkyl, aryl and heteroaryl; $R_5$, $R_6$ and $R_7$ are independently selected from the group consisting of H, $C_{1-8}$ alkyl, $C_{1-8}$ haloalkyl, heteroalkyl, $C_{3-8}$ cycloalkyl, alkyl carboxylic acid, alkylaryl, alkylheteroaryl, aryl and heteroaryl; $R_8$ is selected from the group consisting of H, $C_{1-8}$ alkyl, heteroalkyl, aryl, heteroaryl, $C_{1-8}$-haloalkyl and $C_{3-8}$ cycloalkyl; or a pharmaceutically acceptable salt thereof, with the proviso that the compound is not selected from natural products RA-I, RA-II, RA-III, RA-IV, deoxybouvardin(RA-V), RA-VII, RA-VIII, RA-X, RA-XI, RA-XII, RA-XIII and compounds listed in Scheme 1.

In one aspect of the present invention, there is provided a compound according to Formula III, Wherein $R_1$, $R_2$, $R_3$, $R_{3a}$ and $R_{3b}$ are independently selected from the group consisting of H, halogen, hydroxyl, $C_{1-8}$ alkyl, $C_{1-8}$ haloalkyl, heteroalkyl, $C_{3-8}$ cycloalkyl, amino, cyano, nitro, aryl, heteroaryl, aminoacyl and acylamino; $R_4$ is selected from the group consisting of H, $C_{1-8}$ alkyl, $C_{1-8}$ haloalkyl, $C_{3-8}$ cycloalkyl, heteroalkyl, aryl and heteroaryl; $R_5$, $R_6$ and $R_7$ are independently selected from the group consisting of H, $C_{1-8}$ alkyl, $C_{1-8}$ haloalkyl, heteroalkyl, $C_{3-8}$ cycloalkyl, alkyl carboxylic acid, alkylaryl, alkylheteroaryl, aryl and heteroaryl; $R_8$ is selected from the group consisting of H, $C_{1-8}$ alkyl, heteroalkyl, aryl, heteroaryl, $C_{1-8}$ haloalkyl and $C_{3-8}$ cycloalkyl; or a pharmaceutically acceptable salt thereof, with the proviso that the compound is not selected from natural products RA-I, RA-II, RA-III, RA-IV, deoxybouvardin(RA-V), RA-VII, RA-VIII, RA-X, RA-XI, RA-XII, RA-XIII and compounds listed in Scheme 1.

In one aspect of the present invention, there is provided a compound according to Formula I-III, wherein $R_1$, $R_2$, $R_3$, $R_{3a}$, and $R_{3b}$ are independently selected from the group consisting of H, halogen, hydroxyl, $C_{1-8}$ alkyl, $C_{1-8}$ haloalkyl, $C_{3-8}$ cycloalkyl, heteroalkyl, amino, cyano; $R_5$, $R_6$ and $R_7$ are independently selected from the group consisting of hydrogen and methyl; or a pharmaceutically acceptable salt thereof, with the proviso that the compound is not selected from natural products RA-I, RA-II, RA-III, RA-IV, deoxybouvardin(RA-V), RA-VII, RA-VIII, RA-X, RA-XI, RA-XII, RA-XIII and compounds listed in Scheme 1.

In one aspect of the present invention, there is provided a compound according to Formula I-III, wherein $R_1$, $R_2$, $R_3$, $R_3$, and $R_{3b}$ are independently selected from the group consisting of H, halogen, hydroxyl, $C_{1-8}$ alkyl, $C_{1-8}$ haloalkyl, $C_{3-8}$ cycloalkyl, heteroalkyl, amino, cyano; $R_5$, $R_6$ and $R_7$ are methyl; or a pharmaceutically acceptable salt thereof, with the proviso that the compound is not selected from natural products RA-I, RA-II, RA-III, RA-IV, dcoxybouvardin(RA-V), RA-VII, RA-VII, RA-X, RA-XI, RA-XII, RA-XIII and compounds listed in Scheme 1.

In one aspect of the present invention, there is provided a compound according to Formula I-III, wherein $R_1$, $R_2$, $R_3$, $R_3$, and $R_{3b}$ are independently selected from the group consisting of H, halogen, hydroxyl, $C_{1-8}$ alkyl, $C_{1-8}$ haloalkyl, $C_{3-8}$ cycloalkyl, heteroalkyl, amino, cyano; $R_4$ is selected from the group consisting of hydrogen and methyl; $R_5$, $R_6$ and $R_7$ are methyl; or a pharmaceutically acceptable salt thereof, with the proviso that the compound is not selected from natural products RA-I, RA-II, RA-III, RA-IV, deoxybouvardin (RA-V), RA-VII, RA-VIII, RA-X, RA-XI, RA-XII, RA-XIII and compounds listed in Scheme 1.

In one aspect of the present invention, there is provides a compound according to Formula I-III, wherein $R_1$, $R_2$ and $R_3$ are independently selected from the group consisting of H, halogen, hydroxyl, $C_{1-8}$ alkyl, $C_{1-8}$ haloalkyl, $C_{3-8}$ cycloalkyl, heteroalkyl, amino, cyano; $R_{3a}$ is hydrogen; $R_{3b}$ is para-methoxyl; $R_4$ is selected from the group consisting of hydrogen and methyl; $R_5$, $R_6$ and $R_7$ are methyl; $R_8$ is selected from the group consisting of H, methyl and alkylamino; or a pharmaceutically acceptable salt thereof, with the proviso that the compound is not selected from natural products RA-I, RA-II, RA-III, RA-IV, deoxybouvardin (RA-V), RA-VII, RA-VIII, RA-X, RA-XI, RA-XII, RA-XIII and compounds listed in Scheme 1.

In one aspect of the present invention, there is provided a compound meta Br-N-29-H RA-VII with the following structure:

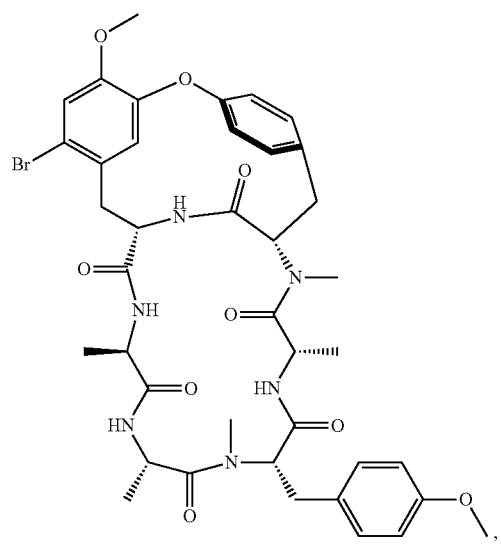

or a pharmaceutically acceptable salt thereof.

One embodiment of the present disclosure provides a compound meta CN-N-29-H RA-VII with the following structure:

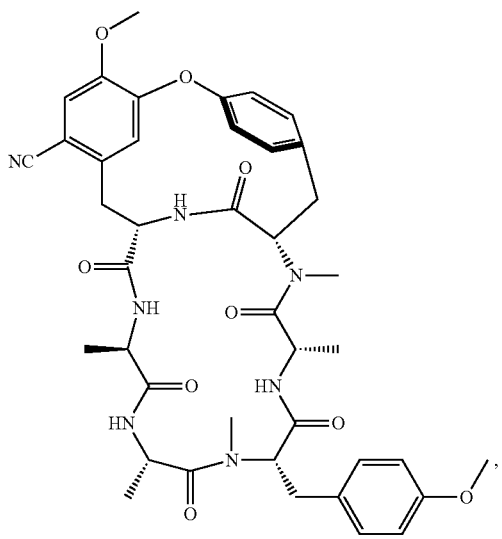

or a pharmaceutically acceptable salt thereof.

Another embodiment of the present disclosure provides a compound meta Cl-N-29-H RA-VII with the following structure:

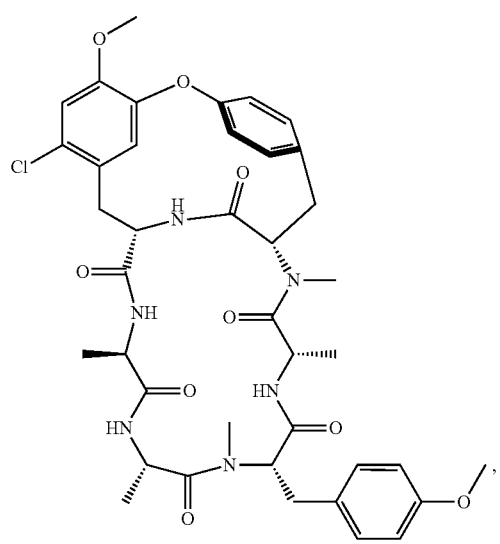

or a pharmaceutically acceptable salt thereof.

In yet another embodiment the present disclosure provides a N-29-H tyr-F-RA-VII compound with the following structure:

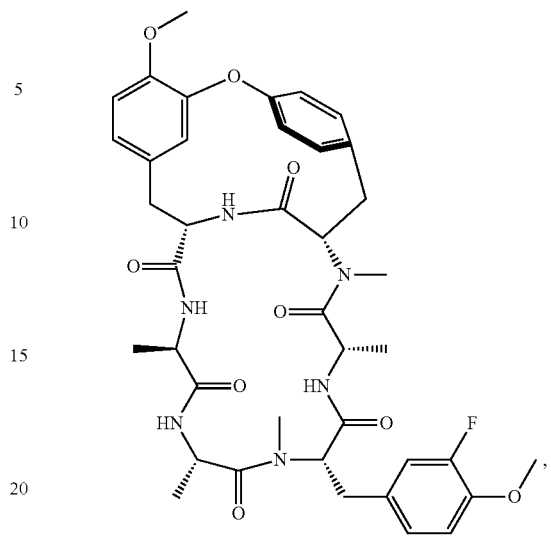

or a pharmaceutically acceptable salt thereof.

In one aspect of the present invention, there is provided a compound selected from the group consisting of:

1-7

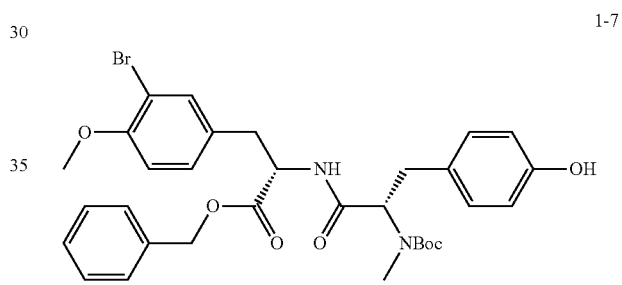

1-8

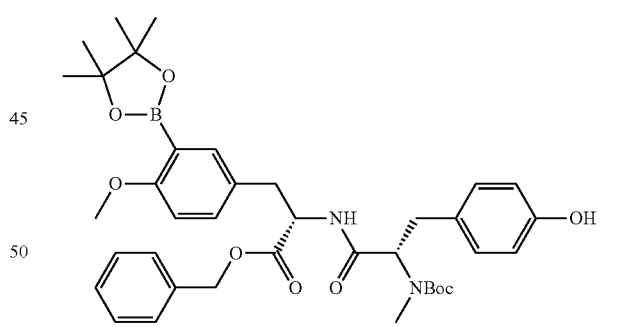

1-9

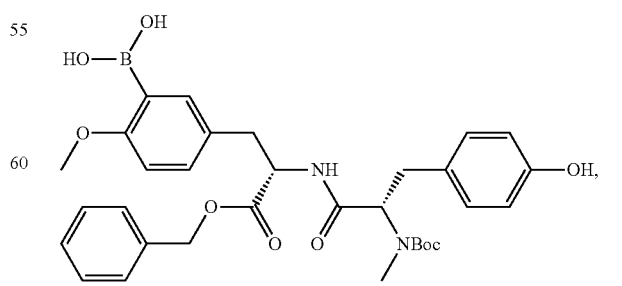

and pharmaceutically acceptable salts thereof.

The chemical entities described herein as "bouvardin derivatives" and related compounds can be synthesized utilizing techniques well known in the art. The reactions illustrated in FIGS. 3-9 are merely illustrative of some methods by which the compound of the present invention can be synthesized. Various modifications to these reactions including, but are not limited to, changing the reaction sequences, changing the reaction conditions (temperature, pressure, catalyst, and ligand) and using a different protecting group, are well within the knowledge of those skilled in the art.

Unlike the synthesis of bouvardin, which took about 30 steps to complete (see Dale L. Boger, Michael A. Patane, Jiacheng Zhou *J. Am. Chem. Soc.,* 1994, 116 (19), pp. 8544-8556), described herein are efficient syntheses of a variety of bouvardin analogs (see FIGS. 3-9 for an exemplary route). While FIGS. 3-9 often depict specific compounds or reaction conditions for their syntheses, the conditions and structure are exemplary and can readily be adapted to other reactants and analogs. Alternative conditions for achieving the same transformation are also well known. The conditions and reaction sequences listed in FIGS. 3-9 are not mean to limit the scope of the invention as set forth in the claims.

Unless specified to the contrary, the reactions described herein take place at atmospheric pressure, generally within a temperature range from −10° C. to 200° C. Further, except as otherwise specified, reaction times and conditions are intended to be approximate, e.g., taking place at about atmospheric pressure within a temperature range of about −10° C. to about 110° C. over a period of about 1 to about 24 hours. The terms "solvent," "organic solvent," and "inert solvent" each mean a solvent inert under the conditions of the reaction being described in conjunction therewith including, for example, benzene, toluene, acetonitrile, tetrahydrofuran ("THF"), dimethylformamide ("DMF"), chloroform, methylene chloride (or dichloromethane), diethyl ether, methanol, N-methylpyrrolidone ("NMP"), pyridine and the like. Unless specified to the contrary, the solvents used in the reactions described herein are inert organic solvents. Unless specified to the contrary, for each gram of the limiting reagent, one cc (or mL) of solvent constitutes a volume equivalent.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples herein below. However, other equivalent separation or isolation procedures can also be used.

When desired, the (R)- and (S)-isomers may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer may be synthesized by asymmetric synthesis using optically active reagents, substrates, catalysts or solvents, or by converting one enantiomer to the other by asymmetric transformation.

The chemical entities can be synthesized by an appropriate combination of generally well-known synthetic methods. Techniques useful in synthesizing the chemical entities are both readily apparent and accessible to those of skill in the relevant art. A racemic mixture can be optionally placed on a chromatography column and separated into (R)- and (S)-enantiomers. The compounds described herein can be optionally contacted with a pharmaceutically acceptable acid to form the corresponding acid addition salts.

Figure 3:
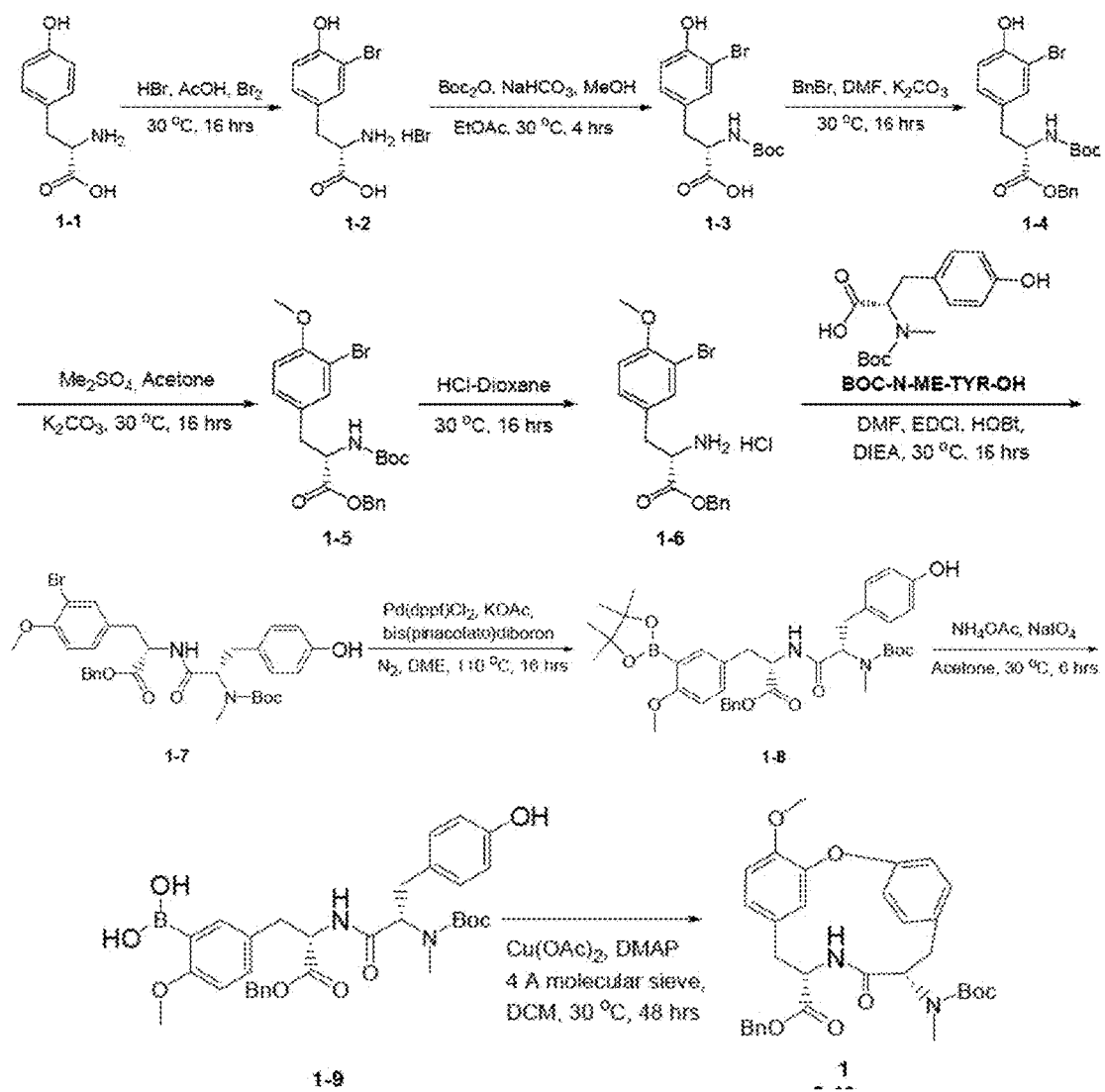
FIG. 3 depicts synthesis of compound 1.

FIG. 3 depicts the synthesis of compound 1. Starting from tyrosine, bromination provides the mono-bromide 1-2, which is further protected in two steps to give ester 1-4. The phenolic oxygen of compound 1-4 is methylated under basic conditions to provide methyl ether 1-5, which is then deprotected to give amine 1-6. Amine 1-6 is coupled with BOC-N-ME-TYR-OH in the presence of coupling reagents, for example, EDCI and HOBT, to give the dipeptide 1-7. Installation of boronic ester is accomplished via a Pd-catalyzed crossing coupling reaction to furnish compound 1-8. The horonic ester moiety is hydrolyzed, for example, using ammonium acetate and $NaIO_4$, to give boronic acid 1-9, which is then cyclized to give compound 1.

Figure 4:
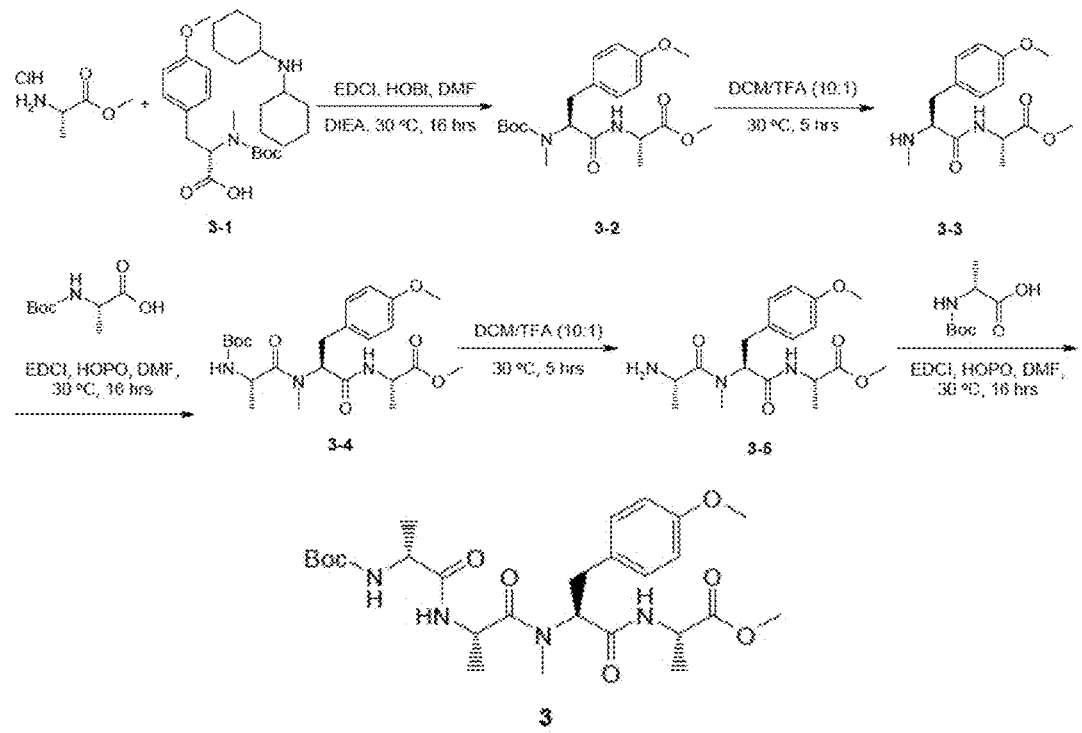
FIG. 4 depicts synthesis of compound 3.

FIG. 4 depicts the synthesis of compound 3, which is the lower segment of bouvardin analogs. Coupling of compound 3-1 and alanine yields dipeptide 3-2. After removing Boc from compound 3-2, the resulting amine 3-3 is coupled to Boc-protected alanine to give tripeptide 3-4. Deprotection of 3-4 followed by another coupling with Boc-protected analine yields tetrapeptide 3.

Figure 5:
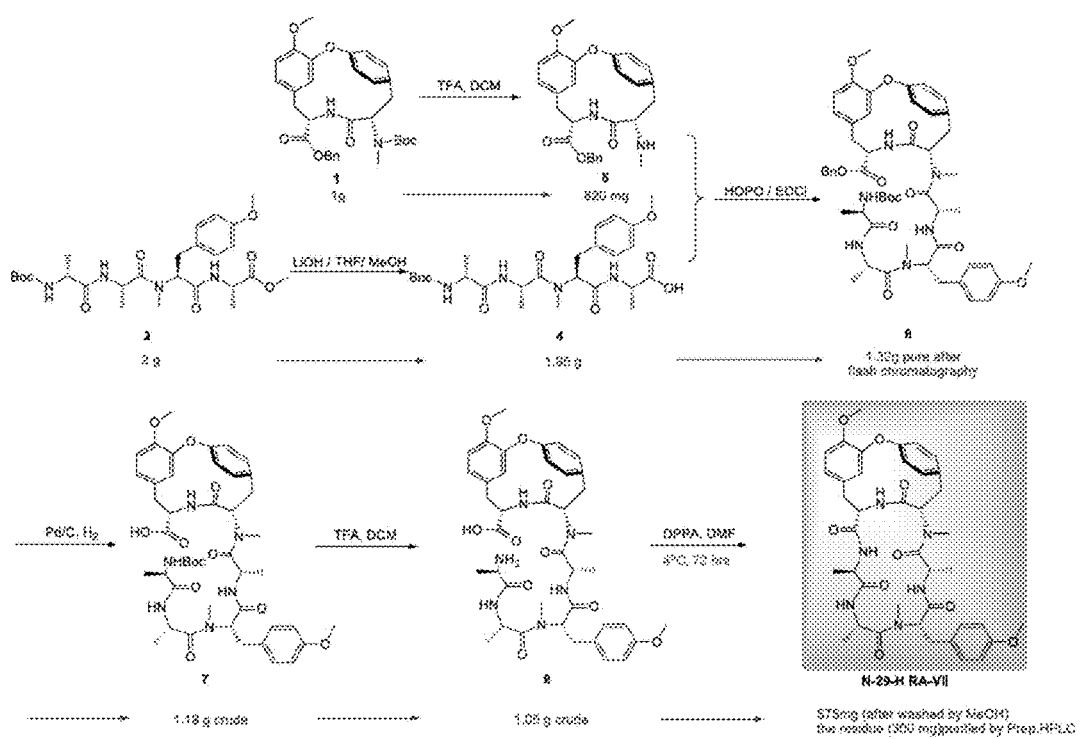
FIG. 5 depicts synthesis of compound N-29-H RA-VII.

FIG. 5 depicts the synthesis of one bouvardin analog, N-29-H RA-VII. Compounds 1 and 3 are deprotected separately to reveal an amino and a carboxy functionality to give compound 5 and 4 respectively, which are coupled with HOPO (2-Hydroxypyridine-N-oxide) and EDCI (1-Ethyl-3-(3-dimethylaminopropyl)carbodiimide) to give compound 6. Deprotection of the benzyl protecting group under hydrogenolysis followed by removing the Boc in compound 6 yields amino acid 8, the macrolactamization of which is achieved with DPPA (diphenyl phosphorazidate).

Figure 6:
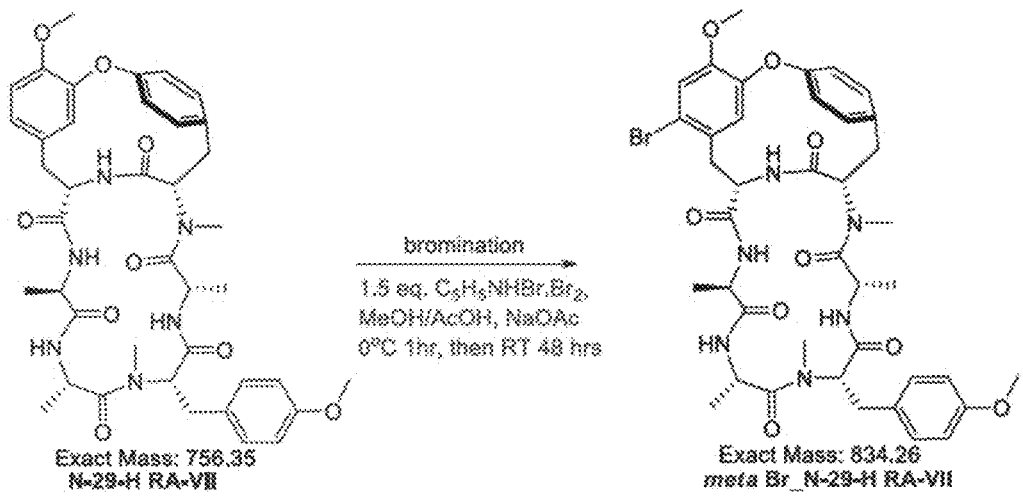
FIG. 6 depicts synthesis of compound meta Br-N-29-H RA-VII.

FIG. 6 depicts the synthesis of meta Br-N-29-H RA-VII. The more electron-rich aryl ring in N-29-H RA-VII is selectively brominated to give the mono-bromide meta Br-N-29-H RA-VII.

Figure 7:
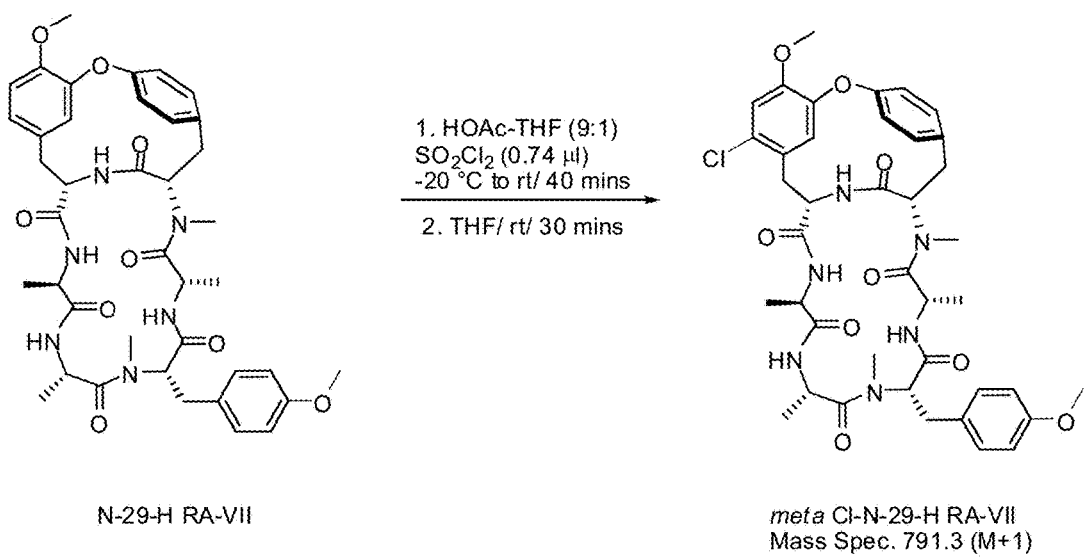
FIG. 7 depicts synthesis of compound meta Cl-N-29-H RA-VII.

FIG. 7 depicts the synthesis of meta Cl-N-29-H RA-VII. The more electron-rich aryl ring in N-29-H RA-VII is selectively chlorinated to give the mono-chloride meta Cl-N-29-H RA-VII.

Figure 8:
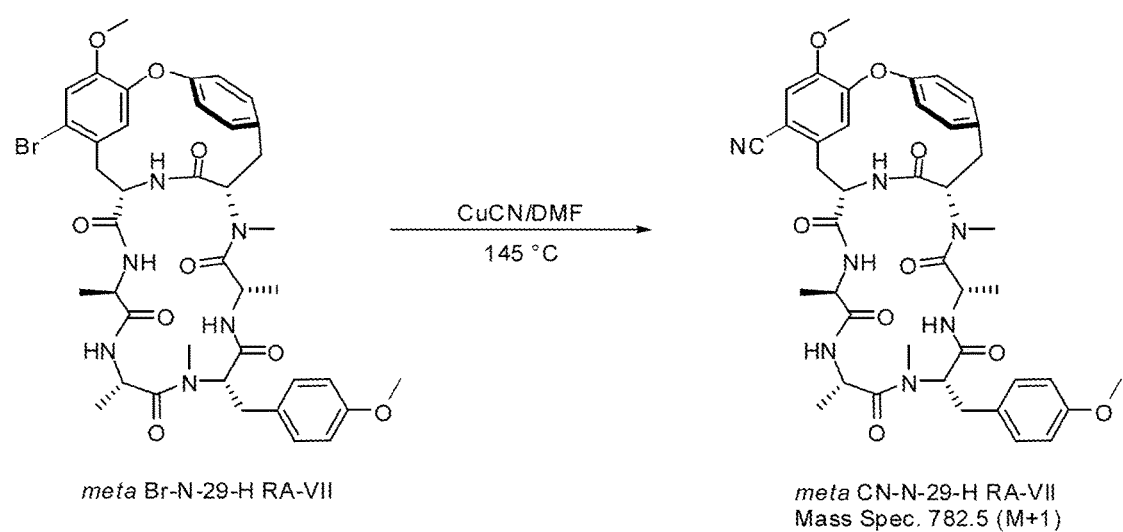
FIG. 8 depicts synthesis of compound meta CN-N-29-H RA-VII.

FIG. 8 depicts the synthesis of meta CN-N-29-H RA-VII. Bouvardin derivative meta Br-N-29-H RA-VII is reacted with cuprous cyanide to give meta CN-N-29-H RA-VII.

Figure 9:
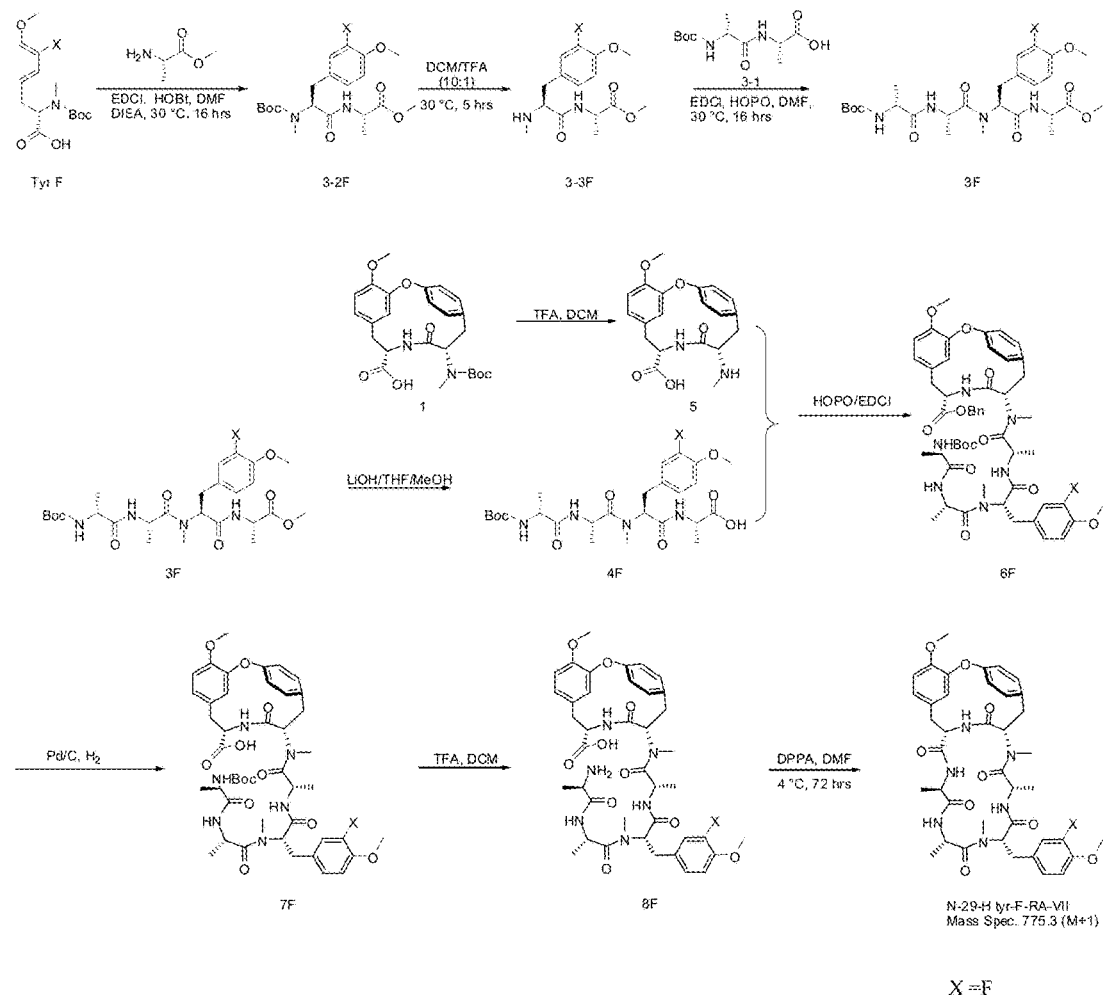
FIG. 9 depicts synthesis of compound N-29-H tyr-F-RA-VII.

FIG. 9 depicts the synthesis of N-29-H tyr-F-RA-VII. Amino acid Tyr X is coupled with (S)-methyl-2-aminopropanoate to give 3-2X. Acidic deprotection of 3-2X followed by coupling with carboxylic acid 3-1 affords the compound 3X. The ester group of the compound 3X is hydrolyzed with LiOH and the resulting acid is coupled with the amine 5 to give compound 6X. Hydrogenolysis of 6X to cleave the benzyl group followed by acidic deprotection of the amine group gives the compound 8X. Reaction of this compound with DPPA in DMF gives N-29-H tyr-F-RA-VII.

Pharmaceutical Compositions and Kits

The compounds of the present invention are usually administered in the form of pharmaceutical compositions. The other agents described herein are also administered in the form of pharmaceutical compositions. When the compounds of the present invention are used in combination with other agents, both components may be mixed into a preparation or both components may be formulated into separate preparations to use them in combination separately or at the same time.

In some aspects this invention therefore provides pharmaceutical compositions that contain, as the active ingredient, a compound of the present invention or a pharmaceutically acceptable salt and/or coordination complex thereof, a second agent or a pharmaceutically acceptable salt and/or coordination complex thereof, and one or more pharmaceutically acceptable, excipients, carriers, include including inert solid diluents and fillers, diluents, including sterile aqueous solution and various organic solvents, permeation enhancers, solubilizers, and adjuvants.

The compound of the present invention may be prepared into pharmaceutical compositions in dosages as described herein see (e.g., "Pharmaceutical compositions for oral administration"). Such compositions are prepared by methods that are well known in the pharmaceutical arts.

In some aspects, the invention provides a composition that contains a compound of the present invention, In some aspects, the concentration of one or more of the compounds is less than 100%, 90%, 80%, 70%, 60%, 50%, 40%, 30%, 20%, 19%, 18%, 17%, 160, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, 0.0001% w/w or v/v.

In some aspects, the concentration of one or more of the compounds of the present invention is greater than 90%, 80%, 70%, 60%, 50%, 40%, 30%, 20%, 19.75%, 19.50%, 19.25%, 19%, 18.75%, 18.50%, 18.25%, 18%, 17.75%, 17.50%, 17.25%, 17%, 16.75%, 16.50%, 16.25%, 16%, 15.75%, 15.50%, 15.25%, 15%, 14.75%, 14.50%, 14.25%, 14%, 13.75%, 13.50%, 13.25%, 13%, 12.75%, 12.50%, 12.25%, 12%, 11.75%, 11.50%, 11.25%, 11%, 10.75%, 10.50%, 10.25%, 10%, 9.75%, 9.50%, 9.25%, 9%, 8.75%, 8.50%, 8.25%, 8%, 7.75%, 7.50%, 7.25%, 7%, 6.75%, 6.50%, 6.25%, 6%, 5.75%, 5.50%, 5.25%, 5%, 4.75%, 4.50%, 4.25%, 4%, 3.75%, 3.50%, 3.25%, 3%, 2.75%, 2.50%, 2.25%, 2%, 1.75%, 1.50%, 1.25%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, 0.0001% w/w or v/v.

In some aspects, the concentration of one or more of the compounds of the present invention is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v, or v/v.

In some aspects, the concentration of one or more of the compounds of the present invention is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v, or v/v.

In some aspects, the amount of one or more of the compounds of the present invention administered to a subject is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some aspects, the amount of one or more of the compounds of the present invention administered to a subject is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 & 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5 g, 3 g, 3.5 g, 4 g, 4.5 g, 5 g, 5.5 g, 6 g, 6.5 g, 7 g, 7.5 g, 8 g, 8.5 g, 9 g, 9.5 g, or 10 g.

In some aspects the amount of one or more of the compounds of the present invention administered to a subject is in the range of 0.0001 g to 10 g, 0.0005 g to 9 g, 0.001 g to 8 g, 0.005 g to 7 g, 0.01 g to 6 g, 0.05 g to 5 g, 0.1 g to 4 g, 0.5 g to 4 g, or 1 g to 3 g.

In some embodiments the combination of radiation therapy will allow for a lower useful does of a compound of the invention. In some embodiments less bouvardin is used in combination with radiation therapy. For example, in some embodiments less than 0.01 mg/kg, less than 0.02 mg/kg, less than 0.05 mg/kg, less than 0.1 mg/kg, less than 0.5 mg/kg, less than 1.0 mg/kg, less than 1.5 mg/kg, or less than 2.0 mg/kg of bouvardin can be used. In some embodiments less than 0.01 mg/kg, less than 0.02 mg/kg, less than 0.05 mg/kg, less than 0.1 mg/kg, less than 0.5 mg/kg, less than 1.0 mg/kg, less than 1.5 mg/kg, or less than 2.0 mg/kg of a bouvardin derivative can be used.

In some embodiments more than one bouvardin derivative is used in combination or in a single composition.

The compounds according to the invention are effective over a wide dosage range. The exact dosage will depend upon the route of administration, the form in which the compound is administered, the subject to be treated, the body weight of the subject to be treated, and the preference and experience of the attending physician.

Pharmaceutical Compositions for Oral Administration.

In some aspects, the invention provides a pharmaceutical composition for oral administration containing a compound of the present invention, and a pharmaceutical excipient suitable for oral administration.

In some aspects, the invention provides a solid pharmaceutical composition for oral administration containing: (i) an effective amount of a compound of the present invention; (ii) an effective amount of a second agent; and (iii) a pharmaceutical excipient suitable for oral administration. In some embodiments, the composition further contains: (iv) an effective amount of a third agent.

In some aspects, the pharmaceutical composition may be a liquid pharmaceutical composition suitable for oral consumption. Pharmaceutical compositions of the invention suitable for oral administration can be presented as discrete dosage forms such as capsules, cachets, tablets, or liquids, or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more necessary ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

In some aspects, this invention further encompasses anhydrous pharmaceutical compositions and dosage forms comprising an active ingredient, since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the present invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs and strip packs.

In some aspects, an active ingredient is combined in an intimate admixture with a pharmaceutical carrier according to conventional pharmaceutical compounding techniques. In various aspects the carrier takes a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents, can be used in the case of oral solid preparations, in some embodiments without employing the use of lactose. For example, suitable carriers include powders, capsules and tablets, with the solid oral preparations. If desired, tablets can be coated by standard aqueous or non-aqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxylmethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder) microcrystalline cellulose, powdered cellulose, dextrates, kaolin, mannitol, silicic acid, sorbitol, starch, pre-gelatinized starch, and mixtures thereof.

Disintegrants may be used in the composition of the invention to provide tablets that disintegrated when exposed to an aqueous environment. Too much of a disintegrant may produce tables which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, crocarmellose sodium, crospovidone, polacrilin potassium, sodium starch glycolate, potato or tapioca starch, other starches, pre-gelatanized starch, other starches, clays, other algins, other cellulose, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel, a coagulated aerosol of synthetic silica, or mixtures thereof. A lubricant can be optionally added, in an amount of less than about 1 weight percent of the pharmaceutical composition.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example, peanut oil, liquid paraffin, or olive oil.

Surfactant which can be used to form pharmaceutical compositions and dosage forms of the invention include, but are not limited to, hydrophilic surfactants, lipophilic surfactants, and mixtures thereof. That is, a mixture of hydrophilic surfactants may be employed, or a mixture of at least one hydrophilic surfactant and at least one lipophilic surfactant may be employed.

A suitable hydrophilic surfactant may generally have an HLB value of at least 10, while lipophilic surfactants may generally have an HLB value of or less than about 10. An empirical parameter is used to characterize the relative hydrophilicity and hydrophobicity of non-ionic amphiphilic compounds is the hydrophilic-lipophilic balance ("HLB value"). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e. hydrophobic) surfactants are compounds having an HLB value equal to or less than about 10. However, HLB value of a surfactant is merely a rough guide generally used to enable formulation of industrial pharmaceutical and cosmetic emulsions.

Hydrophilic surfactants may be either ionic or non-ionic. Suitable ionic surfactants include, but are not limited to, alklylammonium salts; fusidic acid salts, fatty acid salts; fatty acid derivatives of amino acids, oligopeptides and polypeptides; glyceride derivatives of amino acids, oligopeptides and polypeptides; lecithins and hydrogenated lecithins; lysolecithins and hydrogenated lethicithins; phospholipids and derivatives thereof; lysophospholipids and derivatives thereof; carnitine fatty acid ester salts; salts of alkylsulfates; fatty acid salts; sodium docusate; acyltactylates; mono- and di-acetylated tartaric acid esters of mono- and di-glycerides; succinylated mono- and di-glycerides; citric acid esters of mono- and di-glycerides; and mixtures thereof.

Within the aforementioned group, preferred ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and diacetylated tartaric acid esters of mono- and di-glycerides; succinlylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phoshatidic acid, phosphatidylserine, lysophosphatidylcholine, lysophosphatidylethanolamine, lysophosphatidylglycerol, lysophosphatidic acid, lysophosphatidylerine, PEG-phosphatidylethanolamine, PVP-phosphatidylethanolamine, lactylic esters of fatty acids, stearoyl-2-lactylate, succinylated mono glycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carntines, palmitoyl carnitines, myristoyl carnitines, and salts and mixtures thereof.

Hydrophilic non-ionic surfactants may include, but not limited to, alkylglucosides; alkylmahltosides; alkylthioglucosides; lauryl macrogolglycerides: polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate. PEG-32 laurate, PEG-32 dilaurate, PEG-12 oleate, PEG-15 oleate, PEG-20 oleate, PEG-20 dioleate. PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl triolcate, PEG-32 diolcate. PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil. PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol. PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides. In one embodiment, the composition may include a solubilizer to ensure good solubilization and/or dissolution of the compound of the present invention and to minimize precipitation of the compound of the present invention. This can be especially important for compositions for non-oral use, e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water. Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less.

Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, hinders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Pharmaceutical Compositions for Injection.

In some embodiments, the invention provides a pharmaceutical composition for injection containing a compound of the present invention and a pharmaceutical excipient suitable for injection. Components and amounts of agents in the compositions are as described herein.

The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Pharmaceutical Compositions for Topical and/or Transdermal Delivery.

In some embodiments, the invention provides a pharmaceutical composition for topical and/or transdermal delivery containing a compound of the present invention and a pharmaceutical excipient suitable for topical and/or transdermal delivery.

Compositions of the present invention can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another preferred formulation for use in the methods of the present invention employs transdermal delivery devices ("patches"). Such transdermal patches may be used to provide continuous or discontinuous infusion of a compound of the present invention in controlled amounts, either with or without another agent.

The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

Other Pharmaceutical Compositions.

Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., Anderson, Philip O.; Knoben, James E.; Troutman. William G, eds., Handbook of Clinical Drug Data, Tenth Edition, McGraw-Hill, 2002; Pratt and Taylor, eds., Principles of Drug Action, Third Edition, Churchill Livingston, N.Y., 1990; Katzung, ed., Basic and Clinical Pharmacology. Ninth Edition, McGraw Hill, 2004: Goodman and Gilman, eds., The Pharmacological Basis of Therapeutics, Tenth Edition, McGraw Hill 2001; Remingtons Pharmaceutical Sciences, 20th Ed., Lippincott Williams & Wilkins., 2000; Martindale, The Extra Pharmacopoeia. Thirty-Second Edition (The Pharmaceutical Press, London, 1999); all of which are incorporated by reference herein in their entirety.

The invention also provides kits. The kits include a compound or compounds of the present invention as described herein, in suitable packaging, and written material that can include instructions for use, discussion of clinical studies, listing of side effects, and the like. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another agent. In some embodiments, the compound of the present invention and the agent are provided as separate compositions in separate containers within the kit. In some embodiments, the compound of the present invention and the agent are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in some embodiments, be marketed directly to the consumer.

Additional illustrative compounds of the invention include the following embodiments:

The invention provides a pharmaceutical composition comprising one or more compounds disclosed herein. In some embodiments the invention provides pharmaceutical compositions for the treatment of cancer and diseases associated with proliferation and protein synthesis activity in a mammal. In some embodiment, the treatment of said disorders comprises a therapeutically effective amount of a compound of the present invention, or a pharmaceutically acceptable salt, ester, prodrug, solvate, hydrate, or derivative thereof, and a pharmaceutically acceptable carrier.

In some aspects the compositions or compounds of the invention relate to the treatment of cancer, such as acute myeloid leukemia, thymus, brain, lung, squamous cell, skin, eye, retinoblastoma, intraocular melanoma, oral cavity and oropharyngeal, bladder, gastric, stomach, pancreatic, breast, cervical, head, neck, renal, kidney, liver, ovarian, prostate, colorectal, esophageal, testicular, gynecological, thyroid, CNS, PNS, AIDS-related (e.g. Lymphoma and Kaposi's Sarcoma), or Viral-Induced cancer. In some embodiments, the pharmaceutical composition is for the treatment of a non-cancerous hyper proliferative disorder such as benign hyperplasia of the skin (e.g., psoriasis), restinosis, or prostate (e.g., benign prostactic hypertrophy (BPH)).

In some aspects the compositions or compounds of the invention relate to the treatment of diabetes in a mammal.

In some embodiments the invention also relates to compositions for the treatment of pancreatitis or kidney disease (including proliferative glomerulonephritis and diabetes-induced renal disease) or pain in a mammal which comprises a therapeutically effective amount of a compound of the present invention, or a pharmaceutically acceptable salt, ester, prodrug, solvate, hydrate, or derivative thereof, and a pharmaceutically acceptable carrier.

In some embodiments the invention also relates to a composition for treating a disease related to vasculogenesis or angiogenesis in a mammal. In some embodiments, the invention relates to pharmaceutical compositions for treating a disease related to vasculogenesis or angiogenesis in a mammal which comprises a therapeutically effective amount of a compound of the present invention, or a pharmaceutically acceptable salt, ester, prodrug, solvate, hydrate, or derivative thereof, and a pharmaceutically acceptable carrier. In some embodiments, said pharmaceutical composition is for treating a disease selected from the group consisting of tumor angiogenesis, chronic inflammatory disease such as rheumatoid arthritis, inflammatory bowel disease, atherosclerosis, skin diseases such as psoriasis, eczema, and scleroderma, diabetes, diabetic retinopathy, sarcoma and ovarian, breast, lung, pancreatic, prostate, colon, and epidermoid cancer.

In some aspects the LD50 in mice of compounds disclosed herein are within the range shown by FDA-approved chemotherapy agents, such as 0.01 mg/kg to 10,000 mg/kg, or 0.1 mg/kg to 1,000 mg/kg, or 1 mg/kg to 100 mg/kg. In some embodiments, the LD50 of bouvardin is 12.4 mg/kg.

Methods and Uses

The present invention relates to discovery of compounds and their uses for the treatment of disorders including cancer. Without being bound by theory, some compounds of the present invention inhibit the elongation step of protein translation.

Without being limiting, one application of the present invention is for treating cancer. Among the current cancer therapies, chemotherapy and radiation have devastating side effects. Combination therapies using drugs that target different aspects of disease progression may be potentially more efficacious and safer allowing the use of less of each agent. It is anticipated that compounds of the present invention can be used in combination with radiation and chemotherapy for cancer including, for example, but is not limited to, Non-Small Cell Lung Cancer (NSCLC) and Head and Neck Cancers (HNC). There is an unmet medical need with products that can improve the five-year survival rate, reduce tumor size, and prevent tumor recurrence.

Figure 16:
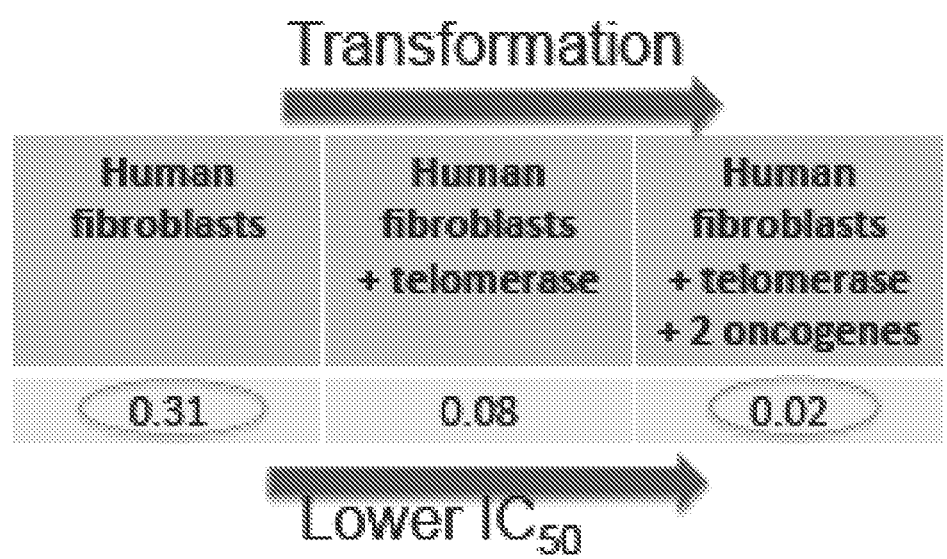
FIG. 16 shows that IC for bouvardin decreases as human primary fibroblasts are transformed with more and more oncogenes.

Currently, protein translation is under-utilized as a target area for anti-cancer drugs. This may be attributed to two strong biases in the field: (1) translation inhibitors are thought to be too toxic and (2) inhibition of translation is thought to lack specificity to target cancer cells. However, $LD_{50}$ in mice of translation inhibitors are within the range of FDA-approved chemotherapy agents. For example, $LD_{50}$ for Bouvardin is 12.4 mg/kg; $LD_{50}$ for cisplatin, and doxorubicin are 6.6 mg/kg and 12.5 mg/kg respectively. Further, multiple studies have now found that increased translation contributes to oncogenesis and that reducing translation can specifically inhibit the growth of cancer cells. IC, for bouvardin decreases as human primary fibroblasts are transformed with more and more oncogenes (FIG. 16); in other words, the more cancer-like cells are, the higher their sensitivity to inhibition of translation. The reason for specificity appears to be that cancer cells are "addicted" to increased protein synthesis such that even partial inhibition can severely disrupt the growth of the former.

Three anti-ribosomals have been described in U.S. Pat. No. 7,695,899, which is herein incorporated by reference in its entirety. The screen was carried out in a whole animal *Drosophila* model. *Drosophila* undergoes cell death followed by repopulation after radiation exposure, and does so using homologs of human genes, thus offering common potential drug targets. Screens through two NCI libraries yielded three classes of molecules: microtubule poisons (e.g vincristine), molecules that interfere with DNA metabolism and transcription (e.g. Topotecan), and anti-ribosomals. The first two classes are known to be effective in combination therapy with radiation in human cancer.

Single Agent

In some aspects, the present invention provides a method for treating disorders in a mammal that comprises administering to the mammal a therapeutically effective amount of a compound of the present invention, or a pharmaceutically acceptable salt, ester, prodrug, solvate, hydrate or derivative thereof. In some embodiments, the method relates to the treatment of cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS-related (e.g. Lymphoma and Kaposi's Sarcoma) or viral-induced cancer.

In some aspects, the invention provides a method of treating diseases related to vasculogenesis or angiogenesis in a mammal that comprises administering to said mammal a therapeutically effective amount of a compound of the present invention, or a pharmaceutically acceptable salt, ester, prodrug, solvate, hydrate or derivative thereof. In some embodiments, said method is for treating a disease selected from the group consisting of tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

In some aspects, patients that can be treated with compounds of the present invention, or pharmaceutically acceptable salt, ester, prodrug, solvate, hydrate or derivative of said compounds, according to the methods of this invention include, for example, patients that have been diagnosed as having psoriasis; restenosis; atherosclerosis; BPH; breast cancer such as a ductal carcinoma in duct tissue in a mammary gland, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; uterine cancer; cervical cancer such as adenocarcinoma in the cervix epithelial including squamous cell carcinoma and adenocarcinomas; prostate cancer, such as a prostate cancer selected from the following: an adenocarcinoma or an adenocarinoma that has migrated to the bone; pancreatic cancer such as epitheliod carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), and myelodysplastic syndrome (MDS); bone cancer; lung cancer such as non-small cell lung cancer (NSCLC), which is divided into squamous cell carcinomas, adenocarcinomas, and large cell undifferentiated carcinomas, and small cell lung cancer: skin cancer such as basal cell carcinoma, melanoma, squamous cell carcinoma and actinic keratosis, which is a skin condition that sometimes develops into squamous cell carcinoma; eye retinoblastoma; cutaneous or intraocular (cyc) melanoma; primary liver cancer (cancer that begins in the liver); kidney cancer; thyroid cancer such as papillary, follicular, medullary and anaplastic; AIDS-related lymphoma such as diffuse large B-cell lymphoma, B-cell immunoblastic lymphoma and small non-cleaved cell lymphoma; Kaposi's Sarcoma; viral-induced cancers including hepatitis B virus (HBV), hepatitis C virus (HCV), and hepatocellular carcinoma; human lymphotropic virus-type 1 (HTLV-I) and adult T-cell leukemia lymphoma; and human papilloma virus (HPV) and cervical cancer; central nervous system cancers (CNS) such as primary brain tumor, which includes gliomas (astrocytoma, anaplastic astrocytoma, or glioblastoma multiforme), Oligodendroglioma, Ependymoma. Meningioma, Lymphoma, Schwannoma, and Medulloblastoma; peripheral nervous system (PNS) cancers such as acoustic neuromas and malignant peripheral nerve sheath tumor (MPNST) including neurofibromas and schwannomas, malignant fibrous cytoma, malignant fibrous histiocytoma, malignant meningioma, malignant mesothelioma, and malignant mixed Mullerian tumor: oral cavity and oropharyngeal cancer such as, hypopharyngeal cancer, laryngeal cancer, nasopharyngeal cancer, and oropharyngeal cancer; stomach cancer such as lymphomas, gastric stromal tumors, and carcinoid tumors; testicular cancer such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin disease, non-Hodgkin lymphomas carcinoids or carcinoid tumors; rectal cancer; and colon cancer.

In some aspects, the invention provides a method of treating diabetes in a mammal that comprises administering to said mamnunal a therapeutically effective amount of a compound of the present invention, or a pharmaceutically acceptable salt, ester, prodrug, solvate, hydrate or derivative thereof.

In some aspects, the invention provides a method of treating an inflammation disorder, including autoimmune diseases, in a mammal that comprises administering to said mammal a therapeutically effective amount of a compound of the present invention, or a pharmaceutically acceptable salt, ester, prodrug, solvate, hydrate or derivative thereof.

Examples of autoimmune diseases includes but is not limited to acute disseminated encephalomyelitis (ADEM), Addison's disease, antiphospholipid antibody syndrome (APS), aplastic anemia, autoimmune hepatitis, coeliac disease, Crohn's disease, Diabetes mellitus (type 1), Goodpasture's syndrome, Graves' disease, Guillain-Barrt syndrome (GBS). Hashimoto's disease, lupus erythematosus, multiple sclerosis, myasthenia gravis, opsoclonus myoclonus syndrome (OMS), optic neuritis. Ord's thyroiditis, oemphigus, polyarthritis, primary biliary cirrhosis, psoriasis, rheumatoid arthritis, Reiter's syndrome, Takayasu's arteritis, temporal arteritis (also known as "giant cell arteritis"), warm autoimmune hemolytic anemia. Wegener's granulomatosis, alopecia universalis, Chagas' disease, chronic fatigue syndrome, dysautonomia, endometriosis, hydradenitis suppurativa, interstitial cystitis, neuromyotonia, sarcoidosis, scleroderma, ulcerative colitis, vitiligo, and vulvodynia. Other disorders include bonc-resorption disorders and thrombosis.

For instance, in some aspects the compounds described herein are used to treat encephalomyelitis. In other embodiments the compounds described herein are used for the treatment of obstructive pulmonary disease. Chronic obstructive pulmonary disease (COPD) is an umbrella term for a group of respiratory tract diseases that are characterized by airflow obstruction or limitation. Conditions included in this umbrella term are: chronic bronchitis, emphysema, and bronchiectasis.

In some aspects, the compounds described herein are used for the treatment of asthma. Also, the compounds described herein may be used for the treatment of endotoxemia and sepsis. In one embodiment, the compounds described herein are used to for the treatment of rheumatoid arthritis (RA). In yet another embodiment, the compounds described herein is used for the treatment of contact or atopic dermatitis. Contact dermatitis includes irritant dermatitis, phototoxic dermatitis, allergic dermatitis, photoallergic dermatitis, contact urticaria, systemic contact-type dermatitis and the like. Irritant dermatitis can occur when too much of a substance is used on the skin of when the skin is sensitive to certain substance. Atopic dermatitis, sometimes called eczema, is a kind of dermatitis, an atopic skin disease.

In another embodiment, compounds described herein may be used to treat acne.

In another embodiment, the compounds described herein may be used for the treatment of arteriosclerosis, including atherosclerosis. Arteriosclerosis is a general term describing any hardening of medium or large arteries. Arterosclerosis is a hardening of an artery specifically due to an atheromatous plaque.

In another embodiment, the compounds described herein may be used for the treatment of neurological disorders that accompany abnormal protein accumulation, including Alzheimer's disease.

In another embodiment, the compounds described herein may be used for the treatment of glomerulonephritis. Glomerulonephritis is a primary or secondary autoimmune renal disease characterized by inflammation of the glomeruli. It may be asymptomatic, or present with hematuria and/or proteinuria. There are many recognized types, divided in acute, subacute or chronic glomerulonephritis. Causes are infectious (bacterial, viral or parasitic pathogens), autoimmune or paraneoplastic.

In other embodiments, the compounds described herein may be used for the treatment of bursitis, lupus, acute disseminated encephalomyelitis (ADEM), Addison's disease, antiphospholipid antibody syndrome (APS), aplastic anemia, autoimmune hepatitis, coeliac disease, Crohn's disease, diabetes mellitus (type 1), goodpasture's syndrome, graves' disease, guillain-barre syndrome (GBS), hashimoto's disease, inflammatory bowel disease, lupus erythematosus, myasthenia gravis, opsoclonus myoclonus syndrome (OMS), optic neuritis, ord's thyroiditis, ostheoarthritis, uveoretinitis, pemphigus, polyarthritis, primary biliary cirrhosis, reiter's syndrome, takayasu's arteritis, temporal arteritis, warm autoimmune hemolytic anemia, Wegener's granulomatosis, alopecia universalis, chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, vulvodynia, appendicitis, arteritis, arthritis, blepharitis, bronchiolitis, bronchitis, cervicitis, cholangitis, cholecystitis, chorioamnionitis, colitis, conjunctivitis, cystitis, dacryoadenitis, dermatomyositis, endocarditis, endometritis, enteritis, enterocolitis, epicondylitis, epididymitis, fasciitis, fibrositis, gastritis, gastroenteritis, gingivitis, hepatitis, hidradenitis, ileitis, iritis, laryngitis, mastitis, meningitis, myelitis, myocarditis, myositis, nephritis, omphalitis, oophoritis, orchitis, osteitis, otitis, pancreatitis, parotitis, pericarditis, peritonitis, pharyngitis, pleuritis, phlebitis, pneumonitis, proctitis, prostatitis, pyelonephritis, rhinitis, salpingitis, sinusitis, stomatitis, synovitis, tendonitis, tonsillitis, uveitis, vaginitis, vasculitis, or vulvitis.

In another aspect, the present invention provides methods of disrupting the function of a ribosome through inhibition of elongation factors. The method includes contacting the ribosome with a function-disrupting amount of a compound of the invention. The invention further provides methods of modulating ribosome activity by contacting a ribosome with an amount of a compound of the invention sufficient to modulate the activity of the ribosome. "To modulate" can mean to inhibit or to activate ribosome activity. In some embodiments, the invention provides methods of inhibiting ribosome activity by contacting a ribosome with an amount of a compound of the invention sufficient to inhibit the activity of the ribosome. In some embodiments, the invention provides methods of inhibiting ribosome activity in a solution by contacting said solution with an amount of a compound of the invention sufficient to inhibit the activity of the ribosome in said solution. In some embodiments, the invention provides methods of inhibiting ribosome activity in a cell by contacting said cell with an amount of a compound of the invention sufficient to inhibit the activity of the ribosome in said cell. In some embodiments, the invention provides methods of inhibiting ribosome activity in a tissue by contacting said tissue with an amount of a compound of the invention sufficient to inhibit the activity of the ribosome in said tissue. In some embodiments, the invention provides methods of inhibiting ribosome activity in an organism by contacting said organism with an amount of a compound of the invention sufficient to inhibit the activity of the ribosome in said organism. In some embodiments, the invention provides methods of inhibiting ribosome activity in an animal by contacting said animal with an amount of a compound of the invention sufficient to inhibit the activity of the ribosome in said animal. In some embodiments, the invention provides methods of inhibiting ribosome activity in a mammal by contacting said mammal with an amount of a compound of the invention sufficient to inhibit the activity of the ribosome in said mammal. In some embodiments, the invention provides methods of inhibiting ribosome activity in a human by contacting said human with an amount of a compound of the invention sufficient to inhibit the activity of the ribosome in said human. In some embodiments, the % of ribosome activity after contacting a ribosome with a compound of the invention is less than 10, 20, 30, 40, 50, 60, 70, 80 or 90% of the ribosome activity in the absence of said contacting step.

The present invention provides methods of treating a disease mediated by ribosome activity (e.g. Elongation Factor 1(EF1) or Elongation Factor 2 (EF2)) in a subject in need of such treatment. The method includes administering to the subject a therapeutically effective amount of a compound of the invention.

The present chemical entities, pharmaceutical compositions and methods provide manners of modulating the catalytic activity of a ribosome. The method includes the step of contacting the ribosome with an activity modulating amount an affinity pocket binding chemical entity antagonist. Also provided are methods of treating a condition or disorder mediated by ribosome activity in a subject in need of such treatment. The method includes administering to the subject a therapeutically effective amount of a chemical entity antagonist.

Combination Treatment

In some aspects, the present invention also provides methods for combination therapies in which an agent known to modulate other pathways, or other components of the same pathway, or even overlapping sets of target enzymes are used in combination with a compound of the present invention, or a pharmaceutically acceptable salt, ester, prodrug, solvate, hydrate or derivative thereof. In one aspect, such therapy includes but is not limited to the combination of compounds of this invention with chemotherapeutic agents, therapeutic antibodies, and radiation treatment, to provide a synergistic therapeutic effect.

Specifically, in one aspect, this invention also relates to a pharmaceutical composition for inhibiting abnormal cell growth or protein accumulation in a mammal which comprises an amount of a compound of the present invention, or a pharmaceutically acceptable salt, ester, prodrug, solvate, hydrate or derivative thereof, in combination with an amount of an anti-cancer agent (e.g. a chemotherapeutic agent), wherein the amounts of the compound, salt, ester, prodrug, solvate, hydrate or derivative, and of the chemotherapeutic are together effective in inhibiting abnormal cell growth. Many chemotherapeutics are presently known in the art and can be used in combination with the compounds of the invention.

In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

A wide variety of anti-cancer agents can be employed in combination. Non-limiting examples are chemotherapeutic agents, cytotoxic agents, and non-peptide small molecules such as Gleevec (imatinib mesylate), Velcade (bortezomib), Casodex (bicalutamide), Iressa (gefitinib), and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinopbilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan: lonidamine; mitoguazone; mitoxantrone; mopidamol; nitracrine; pentostatin; phenamet; pirarubicin; podophyllinic acid; 2-ethylhydrazide; procarbazine; PSK.R™; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipohroman; gacytosine; arabinoside ("Ara-C"); cyclophosphamide; thiotepa; taxanes, e.g. paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; and pharmaceutically acceptable salts, acids or derivatives of any of the above. Also included as suitable chemotherapeutic cell conditioners are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (Fareston): and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylornithine (DMFO). This invention further relates to a method for inhibiting abnormal cell growth in a mammal or treating a hyperproliferative disorder which method comprises administering to the mammal an amount of a compound of the present invention, or a pharmaceutically acceptable salt, ester, prodrug, solvate, hydrate or derivative thereof, in combination with radiation therapy, wherein the amounts of the compound, salt, ester, prodrug, solvate, hydrate or derivative, is in combination with the radiation therapy effective in inhibiting abnormal cell growth or treating the hyperproliferative disorder in the mammal. Techniques for administering radiation therapy are known in the an, and these techniques can be used in the combination therapy described herein. The administration of one or more of the compounds of the invention in this combination therapy can be determined as described herein.

In some embodiments, a compound of present invention is used in combination with taxanes, e.g. paclitaxel (TAXOL™, Bristol-Myers Squibb Oncology, Princeton, N.J.) and docetaxel (TAXOTERE™, Rhone-Poulenc Rorer, Antony, France). In some embodiments a compound of present invention is used in combination with paclitaxel. In some embodiments a composition comprising paclitaxel and a compound of the present invention is administered. In some embodiments a compound of the present invention is used in combination with DHA-paclitaxel. In some embodiments a composition comprising DHA-paclitaxel and a compound of the present invention is administered. In some embodiments a compound of the present invention is used in combination with tumor-activated Taxol prodrugs or paclitaxel bonded to a polyglutamate polymer.

In some embodiments, use of compounds of the present invention may allow for the reduction of the dosage of Taxol in the treatment of cancers. In some embodiments, the amount of Taxol administered intravenously to treat breast carcinoma, when combined with one or more compounds of the present invention, is about 175 mg/m$^2$ over 3 hours, or about 165 mg/m$^2$ over 3 hours, or about 155 mg/m$^2$ over 3 hours, or about 145 mg/m$^2$ over 3 hours, or about 135 mg/m$^2$ over 3 hours, or about 125 mg/m$^2$ over 3 hours, or about 115 mg/m$^2$ over 3 hours, or about 105 mg/m$^2$ over 3 hours, or about 95 mg/m$^2$ over 3 hours, or about 85 mg/m$^2$ over 3 hours, or about 75 mg/m$^2$ over 3 hours, or about 65 mg/m$^2$ over 3 hours, or about 55 mg/m$^2$ over 3 hours, or about 45 mg/m$^2$ over 3 hours, or about 35 mg/m$^2$ over 3 hours, or about 25 mg/m$^2$ over 3 hours, or about 15 mg/m$^2$ over 3 hours, or about 5 mg/m$^2$ over 3 hours, or about 1 mg/m$^2$ over 3 hours.

In some embodiments, the amount of Taxol administered intravenously to treat non-small cell lung carcinoma, when combined with one or more compounds of the present invention, is about 135 mg/m2 over 24 hours, or about 125 mg/m2 over 3 hours, or about 115 mg/m2 over 24 hours, or about 105 mg/m2 over 24 hours, or about 95 mg/m2 over 3 hours, or about 85 mg/m2 over 24 hours, or about 75 mg/m2 over 24 hours, or about 65 mg/m2 over 24 hours, or about 55 mg/m2 over 24 hours, or about 45 mg/m2 over 24 hours, or about 35 mg/m2 over 24 hours, or about 25 mg/m2 over 24 hours, or about 15 mg/m2 over 24 hours, or about 5 mg/m2 over 24 hours, or about 1 mg/m2 over 24 hours.

In further embodiments, treatment with Taxol and one or more compounds of this invention can be followed by intravenous administration of cis-platin. In some embodiments, the amount of cis-platin administered is about 75 mg/m2, or about 65 mg/m2, or about 55 mg/m2, or about 45 mg/m2, or about 35 mg/m2, or about 25 mg/m2, or about 15 mg/m2, or about 5 mg/m2, or about 1 mg/m2.

In some embodiments other taxanes are administered as described for Taxol.

In some aspects, the anti-cancer agents and one or more of the compounds of the invention are administered simultaneously. In some embodiments the anti-cancer agents and one or more of the compounds of the invention are administered in the same formulation. In some embodiments the anti-cancer agents and one or more of the compounds of the invention are administered in a staggered fashion, for instance every other day or at different meal times. In some embodiments the anti-cancer agents and one or more of the compounds of the invention are administered as two separate formulations administered at different times. In some embodiments the anti-cancer agents and one or more of the compounds of the invention are administered as two separate formulations administered at similar times.

In some aspects, the invention provides for method for instructing a patient or medical professional regarding the proper dosage of a compound of the invention to be used in combination with one or more additional anti-cancer agents. In some embodiments the invention provides for method for instructing a patient regarding the proper compound of the invention to be used in combination with a particular anti-cancer agent.

In some aspects, there is provided a method for treating a disorder in a subject comprising: (a) administering an effective amount of an inhibitor of protein translation to a subject in need of treatment; and (b) administering to the subject an effective amount of radiation therapy. In various aspects radiation therapy is administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. In some embodiments, the radiation therapy is given at a dosage of 20 Gy to 80 Gy total, fractionated into smaller doses over a course of treatment that may last several weeks. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g. At-211, I-131, I-125, Y-90, Re-186, Re-188, Sm-153, Bi-212, P-32, and radioactive isotopes of Lu). Suitable radiation sources for use as a cell conditioner of the present invention include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g. a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Without being limited by any theory, the compounds of the present invention render abnormal cells more sensitive to treatment with radiation for purposes of killing and/or inhibiting the growth of such cells.

Accordingly, aspects of this invention further relates to a method for sensitizing abnormal cells in a mammal to treatment with radiation which comprises administering to the mammal an amount of a compound of the present invention or pharmaceutically acceptable salt, ester, prodrug, solvate, hydrate or derivative thereof, which amount is effective is sensitizing abnormal cells to treatment with radiation. The amount of the compound, salt, or solvate in this method can be determined according to the means for ascertaining effective amounts of such compounds described herein.

The invention also relates to a method of and to a pharmaceutical composition of inhibiting abnormal cell growth in a mammal which comprises an amount of a compound of the present invention, or a pharmaceutically acceptable salt, ester, prodrug, solvate, hydrate or derivative thereof, or an isotopically-labeled derivative thereof, and an amount of one or more substances selected from anti-angiogenesis agents, signal transduction inhibitors, and anti-proliferative agents.

Anti-angiogenesis agents, such as MMP-2 (matrix-metalloprotienase 2) inhibitors, MMP-9 (matrix-metalloprotienase 9) inhibitors, and COX-11 (cyclooxygenase 11) inhibitors, can be used in conjunction with a compound of the present invention and pharmaceutical compositions described herein. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999). U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-I. Alsoagents are those that selectively inhibit MMP-2 and/or AMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13). Some specific examples of MMP inhibitors useful in the present invention are AG-3340, RO 32-3555, and RS 13-0830.

The compounds of the invention may be formulated or administered in conjunction with other agents that act to relieve the symptoms of inflammatory conditions such as encephalomyelitis, asthma, and the other diseases described herein. These agents include non-steroidal anti-inflammatory drugs (NSAIDs), e.g. acetylsalicylic acid; ibuprofen; naproxen; indomethacin; nabumetone; tolmetin; etc. Corticosteroids are used to reduce inflammation and suppress activity of the immune system. The most commonly prescribed drug of this type is Prednisone. Chloroquine (Aralen) or hydroxychloroquine (Plaquenil) may also be very useful in some individuals with lupus. They are most often prescribed for skin and joint symptoms of lupus. Azathioprine (Imuran) and cyclophosphamide (Cytoxan) suppress inflammation and tend to suppress the immune system. Other agents, e.g. methotrexate and cyclosporin are used to control the symptoms of lupus. Anticoagulants are employed to prevent blood from clotting rapidly. They range from aspirin at very low dose which prevents platelets from sticking, to heparin/coumadin.

The compounds describe herein may be formulated or administered in conjunction with liquid or solid tissue barriers also known as lubricants. Examples of tissue barriers include, but are not limited to, polysaccharides, polyglycans, seprafilm, interceed and hyaluronic acid.

In some aspects medicaments are administered in conjunction with the compounds described herein. Such medicaments include any suitable drugs usefully delivered by inhalation for example, analgesics, e.g. codeine, dihydromorphine, ergotamine, fentanyl or morphine; anginal preparations, e.g. diltiazem; antiallergics, e.g. cromoglycate, ketotifen or nedocromil; anti-infectives, e.g. cephalosporins, penicillins, streptomycin, sulphonamides, tetracyclines or pentamidine; antihistamines. e.g. methapyrilene; antiinflammatories, e.g. beclomethasone, flunisolide, budesonide, tipredane, triamcinolone acetonide or fluticasone; antitussives, e.g. noscapine; bronchodilators, e.g. ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (−)-4-amino-3,5-dichloro-α-[[[6-[2-(2-pyridinyl)ethoxy]hexyl]-amino]methyl] benzenemethanol; diuretics, e.g. amiloride; anticholinergics e.g. ipratropium, atropine or oxitropium; hormones, e.g. cortisone, hydrocortisone or prednisolone; xanthines e.g. aminophylline, choline theophyllinate, lysine theophyllinate or theophylline; and therapeutic proteins and peptides, e.g. insulin or glucagon. It will be clear to a person skilled in the art that, where appropriate, the medicaments may be used in the form of salts (e.g. as alkali metal or amine salts or as acid addition salts) or as esters (e.g. lower alkyl esters) or as solvates (e.g. hydrates) to optimize the activity and/or stability of the medicament.

Other exemplary therapeutic agents useful for a combination therapy include but are not limited to agents as described above, radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and E, growth factors, cytokines, chemokines, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

Therapeutic agents can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, β-adrenergic agonists, ipratropium, glucocorticoids, methylxanthines, sodium channel blockers, opioid receptor agonists, calcium channel blockers, membrane stabilizers and leukotriene inhibitors.

Additional therapeutic agents contemplated herein include diuretics, vasopressin, agents affecting the renal conservation of water, rennin, angiotensin, agents useful in the treatment of myocardial ischemia, anti-hypertensive agents, angiotensin converting enzyme inhibitors, β-adrenergic receptor antagonists, agents for the treatment of hypercholesterolemia, and agents for the treatment of dyslipidemia.

Examples of therapeutic antibodies that can be combined with compounds of this invention include but are not limited to anti-receptor tyrosine kinase antibodies (cetuximab, panitumumab, trastuzumab), anti CD20 antibodies (rituximab, tositumomab), and other antibodies such as alemtuzumab, bevacizumab, and gemtuzumab. Moreover, therapeutic agents used for immunomodulation, such as immunomodulators, immunosuppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and antiplatelet drugs.

Further therapeutic agents that can be combined with one or more compounds of this invention may be found in Goodman and Gilman's "The Pharmacological Basis of Therapeutics," Tenth Edition, edited by Hardman, Limbird and Gilman or the "Physician's Desk Reference", Thomson Reuters; 63rd edition, both of which are incorporated herein by reference in their entirety.

The compounds described herein can be used in combination with the agents disclosed herein or other suitable agents, depending on the condition being treated. Hence, in some embodiments the compounds of the invention will be co-administered with other agents as described above. When used in combination therapy, the compounds described herein may be administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the present invention and any of the agents described above can be simultaneously administered, wherein both the agents are present in separate formulations. In another alternative, a compound of the present invention can be administered just followed by and any of the agents described above, or vice versa. In the separate administration protocol, a compound of the present invention and any of the agents described above may be administered a few minutes apart, or a few hours apart, or a few days apart.

The compounds described herein can be used in combination with BRAF inhibitors. In some embodiments the compounds described herein can be used in combination with one or more BRAF inhibitors selected from the group comprising: Vemurafenib, GDC-0879, PLX-4720, PLX4032, dabrafenib, LGX818, and Sorafenib Tosylate. In some embodiments the compounds described herein can synergize with one or more BRAF inhibitors. In some embodiments one or more of the compounds described herein can synergize with all BRAF inhibitors. For example meta Br-N-29-H RA-VII can synergize with a BRAF inhibitor, for example PLX4032. In some examples meta Cl-N-29-H RA-VII can synergize with one or more BRAF inhibitors including PLX4032. In further examples meta CN-N-29-H RA-VII or N-29-H-Tyr-F-RA-VII can synergize with one or more BRAF inhibitors.

The compounds described herein can be used in combination with P13K inhibitors. In some embodiments the compounds described herein can be used in combination with one or more P13K inhibitors selected from the group comprising: wortmannin, demethoxyviridin. LY294002, perifosine, dabrafenib, CAL101, PX-866, IPI-145, BEZ235, SF1126, INK1117, GDC-0941, BKM120, XL147, XL765, palomid 529, GSK 1059615, ZSTK474, PWT33597, IC87114, TG100-115, CAL 263, PI-103, GNE-477, CUDC-907 and AEZS-136. In some embodiments the compounds described herein can synergize with one or more P13K inhibitors. In some embodiments one or more of the compounds described herein can synergize with all P13K inhibitors. For example meta Br-N-29-H RA-VII can synergize with a P13K inhibitor. In some examples mela Cl-N-29-H RA-VII can synergize with one or more P13K inhibitor. In further examples meta CN-N-29-H RA-VII or N-29-H-Tyr-F-RA-VII can synergize with one or more P13K inhibitor.

In some embodiments the compounds described herein can synergize with PF-04691502, P13K/mTOR dual inhibitor. For example meta Br-N-29-H RA-VII can synergize with PF-04691502. In some examples meta Cl-N-29-H RA-VII can synergize with PF-04691502. In further examples meta CN-N-29-H RA-VII or N-29-H-Tyr-F-RA-VII can synergize with PF-04691502.

The compounds described herein can be used in combination with MEK inhibitors. In some embodiments the compounds described herein can be used in combination with one or more MEK inhibitors selected from the group comprising: trametinib, selumetinib, MEK 162. PD-35901, XL518, CL-1040, PD035901 and TAK-333. In some embodiments the compounds described herein can synergize with one or more MEK inhibitors. In some embodiments one or more of the compounds described herein can synergize with all MEK inhibitors. For example meta Br-N-29-H RA-VII can synergize with a MEK inhibitor, for example TAK-333. In some examples meta Cl-N-29-H RA-VII can synergize with one or more MEK inhibitor including TAK-333. In further examples meta CN-N-29-H RA-VII or N-29-H-Tyr-F-RA-VII can synergize with one or more MEK inhibitor.

The compounds described herein can be used in combination with an agent that inhibits a pathway that B-Raf acts on, e.g. the MAPK pathway. In some embodiments the compounds described herein can be used in combination with RAS, MEK and ERK inhibitors. In some embodiments one or more of the compounds described herein is used in combination with an inhibitor of one or more of the following HRAS, KRAS, NRAS, DIRAS1, DIRAS2, DIRAS3, ERAS, GEM, MRAS, NKIRAS1, NKIRAS2, NRAS, RALA, RALB, RAP1A, RAP1B, RAP2A, RAP2B, RAP2C, RASD1, RASD2, RASL10A, RASL10B, RASL11A, RASL11B, RASL12, REM1, REM2, RERG, RERGL, RRAD, RRAS, and RRAS2. In some embodiments one or more of the compounds described herein is used in combination a drug selected from the group comprising: XL518, CI-1040, PD035901, selumetinib, and GSKI120212. In some embodiments one or more compounds of the invention are use in combination with ERK Inhibitor II, FR180204. In some embodiments these combinations result in a synergistic effect. As used herein, BRAF or B-Raf means gene or protein whenever it is appropriate.

In the embodiments where the compounds described herein are used in combination with BRAF, P13K or MEK inhibitors the concentration of the BRAF, P13K or MEK inhibitors can be in the range of 10 nM-100 nM, 10 nM-200 nM, 10 nM-300 nM, 10 nM-400 nM, 10 nM-500 nM, 10 nM-600 nM, 10 nM-700 nM, 10 nM-800 nM, 10 nM-900 nM, 10 nM-1,000 nM, 10 nM-1,100 nM, 10 nM-1,200 nM, 10 nM-1,300 nM, 10 nM-1,400 nM, 10 nM-1,500 nM, 10 nM-1,600 nM, 10 nM-1,700 nM, 10 nM-1,800 nM, 10 nM-1,900 nM, 10 nM-2,000 nM, 10 nM-3,000 nM, 10 nM-4,000 nM, 10 nM-5,000 nM, 10 nM-4,000 nM, 10 nM-5,000 nM, 10 nM-6,000 nM, 10 nM-7,000 nM, 10 nM-8,000 nM, 10 nM-9,000 nM, 10 nM-10,000 nM, 10 nM-11,000, 10 nM-12,000, 10 nM-13,000, 10 nM-14,000, 10 nM-15,000, 10 nM-16,000, 10 nM-17,000, 10 nM-18,000, 10 nM-19,000, 10 nM-20,000, 100 nM-100 nM, 100 nM-200 nM, 100 nM-300 nM, 100 nM-400 nM, 100 nM-500 nM, 100 nM-600 nM, 100 nM-700 nM, 100 nM-800 nM, 100 nM-900 nM, 100 nM-1,000 nM, 100 nM-1,100 nM, 100 nM-1,200 nM, 100 nM-1,300 nM, 100 nM-1,400 nM, 100 nM-1,500 nM, 100 nM-1,600 nM, 100 nM-1,700 nM, 100 nM-1,800 nM, 100 nM-1,900 nM, 100 nM-2,000 nM, 100 nM-3,000 nM, 100 nM-4,000 nM, 100 nM-5,000 nM, 100 nM-4,000 nM, 100 nM-5,000 nM, 100 nM-6,000 nM, 100 nM-7,000 nM, 100 nM-8,000 nM, 100 nM-9,000 nM, 100 nM-10,000 nM, 100 nM-11,000 nM, 100 nM-12,000 nM, 100 nM-13,000 nM, 100 nM-14,000 nM, 100 nM-15,000 nM, 100 nM-16,000 nM, 100 nM-17,000 nM, 100 nM-18,000 nM, 100 nM-19,000 nM, 100 nM-20,000 nM, 1,000 nM-1,100 nM, 1,000 nM-1,200 nM, 1,000 nM-1,300 nM, 1,000 nM-1,400 nM, 1,000 nM-1,500 nM, 1,000 nM-1,600 nM, 1,000 nM-1,700 nM, 1,000 nM-1,800 nM, 1,000 nM-1,900 nM, 1,000 nM-2,000 nM, 1,000 nM-3,000 nM, 1,000 nM-4,000 nM, 1,000 nM-5,000 nM, 1,000 nM-4,000 nM, 1.000 nM-5,000 nM, 1,000 nM-6,000 nM, 1,000 nM-7,000 nM, 1,000 nM-8,000 nM, 1,000 nM-9,000 nM, 1,000 nM-10,000 nM, 1,000 nM-11,000 nM, 1,000 nM-12,000 nM, 1,000 nM-13,000 nM, 1,000 nM-14,000 nM, 1,000 nM-15,000 nM, 1,000 nM-16,000 nM, 1,000 nM-17,000 nM, 1,000 nM-18,000 nM, 1,000 nM-19,000 nM, 1,000 nM-20,000 nM, 10,000 nM-11,000 nM, 10,000 nM-12,000 nM, 10,000 nM-13,000 nM, 10,000 nM-14,000 nM, 10,000 nM-15,000 nM, 10,000 nM-16,000 nM, 10,000 nM-17,000 nM, 10,000 nM-18,000 nM, 10,000 nM-19,000 nM, or 10,000 nM-20,000 nM.

In some embodiments the concentration of BRAF, PK13 or MEK inhibitors used in combination with the compounds of the current disclosure is 100 nM, 200 nM, 300 nM, 400 nM, 500 nM, 600 nM, 700 nM, 800 nM, 900 nM, 1 µM, 2 µM, 3 µM, 4 µM, 5 µM, 6 µM, 7 µM, 8 µM, 9 µM, or 10 µM. In some embodiments the concentration of BRAF, PK13 or MEK inhibitors used in combination with the compounds of the current disclosure is 200 nM. In some embodiments the concentration of BRAF, PK13 or MEK inhibitors used in combination with the compounds of the current disclosure is 500 nM. In some embodiments the concentration of BRAF, PK13 or MEK inhibitors used in combination with the compounds of the current disclosure is 3 µM. In some embodiments the concentration of BRAF, PK13 or MEK inhibitors used in combination with the compounds of the current disclosure is 6 µM. In some embodiments the concentration of BRAF, PK13 or MEK inhibitors used in combination with the compounds of the current disclosure is 10 µM.

In the embodiments where the compounds described herein are used in combination with BRAF, P13K or MEK inhibitors the concentration of the compounds described herein can be in the range of 0.001 µM-0.01 µM, 0.001 µM-0.02 µM, 0.001 µM-0.03 µM, 0.001 µM-0.04 µM, 0.001 µM-0.05 µM, 0.001 µM-0.06 µM, 0.001 µM-0.07 µM, 0.001 µM-0.08 µM, 0.001 µM-0.09 µM, 0.001 µM-0.1 µM, 0.001 µM-0.2 µM, 0.001 µM-0.3 µM, 0.001 µM-0.4 µM, 0.001 µM-0.5 µM, 0.001 µM-0.6 µM, 0.001 µM-0.7 µM, 0.001 µM-0.8 µM, 0.001 µM-0.9 µM, 0.001 µM-1 µM, 0.001 µM-2 µM, 0.001 µM-3 M, 0.001 µM-4 µM, 0.001 µM-5 µM, 0.001 µM-6 µM, 0.001 µM-7 µM, 0.001 µM-8, 0.001 µM-9 µM, 0.001 µM-10 µM, 0.001 µM-20 µM, 0.001 µM-30 µM, 0.001

μM-40 μM, 0.001 μM-50 μM, 0.001 μM-60 μM, 0.001 μM-70 μM, 0.001 μM-80, 0.001 μM-90 μM, or 0.001 μM-100 μM. In some embodiments the concentration of the compounds disclosed herein when used in combination with BRAF, P13K or MEK inhibitors is 0.01 μM, 0.02 μM, 0.03 μM, 0.04 μM, 0.05 μM, 0.06 μM, 0.07 μM, 0.08 μM, 0.09 μM, 0.1 μM, 0.2 μM, 0.3 μM, 0.4 μM, 0.5 μM, 0.6 μM, 0.7 μM, 0.8 μM, 0.9 μM, 1 μM, 2 μM, 3 μM, 4 μM, 5 μM, 6 μM, 7 μM, 8 μM, 9 μM, 10 μM, 20 μM, 30 μM, 40 μM, 50 μM, 60 μM, 70 μM, 80 μM, 90 μM, or 100 μM.

Administration

In some aspects of the invention the administration of the compounds of the present invention is effected by any method that enables delivery of the compounds to the site of action. These methods include oral routes, intraduodenal routes, parenteral injection (including intravenous, intraarterial subcutaneous, intramuscular, intravascular, intraperitoneal or infusion), topical (e.g. transdermal application), rectal administration, via local delivery by catheter or stent. Compounds can also be administered intraadiposally or intrathecally.

In some aspects of the invention the amount of the compound administered is dependent on the mammal being treated, the severity of the disorder or condition, the rate of administration, the disposition of the compound and the discretion of the prescribing physician.

In some aspects of the invention, the compounds are applied as a sole therapy or may involve one or more other anti-tumor substances, for example those selected from, mitotic inhibitors, for example vinblastine or a taxane; alkylating agents, for example cis-platin, carboplatin and cyclophosphamide; anti-metabolites, for example 5-fluorouracil, cytosine arabinside and hydroxyurea; growth factor inhibitors; cell cycle inhibitors; intercalating antibiotics, for example adriamycin and bleomycin; enzymes, for example, interferon; and anti-hormones, for example anti-estrogens such as Nolvadex™ (tamoxifen) or, for example anti-androgens such as Casodex™ (4'-cyano-3-(4-fluorophenylsulphonyl)-2-hydroxy-2-methyl-3'-(trifluoromethyl) propionanilide). Such conjoint treatment may be achieved by way of the simultaneous, sequential or separate dosing of the individual components of treatment. In some embodiments, the one or more other anti-tumor substances are administered prior to the administration of the compounds described herein. In a further embodiments, the one or more other anti-tumor substances are administered about 1 h, 2 h, 3 h, 4 h 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h, 1.5 d, 2 d 2.5 d, 3 d, 4 d, 5 d, 6 d, 7 d or evern more prior to the administration of the compounds described herein. In some other embodiments, the one or more other anti-tumor substances are administered after the administration of the compounds described herein. In a further embodiments, the one or more other anti-tumor substances are administered about 1 h, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h, 1.5 d, 2 d, 2.5 d, 3 d, 4 d, 5 d, 6 d, 7 d or evern more after the administration of the compounds described herein.

In some embodiments, a compound of the invention is administered in a single dose. Typically, such administration will be by injection, e.g., intravenous injection, in order to introduce the agent quickly. However, other routes may be used as appropriate. A single dose of a compound of the invention may also be used for treatment of an acute condition.

In some embodiments, a compound of the invention is administered in multiple doses. Dosing may be about once, twice, three times, four times, five times, six times, or more than six times per day. Dosing may be about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the agents of the invention may continue as long as necessary. In some embodiments, an agent of the invention is administered for more than 1, 2, 3, 4, 5, 6, 7, 14, or 28 days. In some embodiments, an agent of the invention is administered for less than 28, 14, 7, 6, 5, 4, 3, 2, or 1 day. In some embodiments, an agent of the invention is administered chronically on an ongoing basis. e.g., for the treatment of chronic effects.

An effective amount of a compound of the invention may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

The compositions of the invention may also be delivered via an impregnated or coated device such as a stent, for example, or an artery-inserted cylindrical polymer. Such a method of administration may, for example, aid in the prevention or amelioration of restenosis following procedures such as balloon angioplasty. Without being bound by theory, compounds of the invention may slow or inhibit the migration and proliferation of smooth muscle cells in the arterial wall which contribute to restenosis. A compound of the invention may be administered, for example, by local delivery from the struts of a stent, from a stent graft, from grafts, or from the cover or sheath of a stent. In some embodiments, a compound of the invention is admixed with a matrix. Such a matrix may be a polymeric matrix, and may serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly (ether-ester) copolymers (e.g. PEO-PLLA); polydimethylsiloxane, poly(ethylene-vinylacetate), acrylate-based polymers or copolymers (e.g. polyhydroxyethyl methylmethacrylate, polyvinyl pyrrolidinone), fluorinated polymers such as polytetrafluoroethylene and cellulose esters. Suitable matrices may be nondegrading or may degrade with time, releasing the compound or compounds. Compounds of the invention may be applied to the surface of the stent by various methods such as dipispin coating, spray coating, dip-coating, and/or brush-coating. The compounds may be applied in a solvent and the solvent may be allowed to evaporate, thus forming a layer of compound onto the stent. Alternatively, the compound may be located in the body of the stent or graft, for example in microchannels or micropores. When implanted, the compound diffuses out of the body of the stent to contact the arterial wall. Such stents may be prepared by dipping a stent manufactured to contain such micropores or microchannels into a solution of one or more of the compounds of the invention in a suitable solvent, followed by evaporation of the solvent. Excess drug on the surface of the stent may be removed via an additional brief solvent wash. In yet other embodiments, compounds of the invention may be covalently linked to a stent or graft. A covalent linker may be used which degrades in vivu, leading to the release of one or more of the compounds of the invention. Any bio-labile linkage may be used for such a purpose, such as ester, amide or anhydride linkages. Compounds of the invention may additionally be administered intravascularly from a balloon used during angioplasty. Extravascular administration of the compounds via the pericard or via advential application of formulations of the invention may also be performed to decrease restenosis. The compounds of the invention may be administered in dosages as described herein (see, e.g., Compositions). It is known in the art that due to intersubject variability in compound pharmacokinetics, individualization of dosing regimen is necessary for optimal therapy. Dosing for a compound of the invention may be found by routine experimentation.

When a compound of the invention, is administered in a composition that comprises one or more agents, and the agent has a shorter half-life than one or more of the compounds of the invention unit dose forms of the agent and one or more of the compounds of the invention may be adjusted accordingly. See e.g. "Pharmaceutical compositions for oral administration." The subject pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc. Exemplary parenteral administration forms include solutions or suspensions of active compound in sterile aqueous solutions, for example, aqueous propylene glycol or dextrose solutions. Such dosage forms can be suitably buffered, if desired.

The synthesis and biologic activity of compounds of the present invention may be determined by the procedures described in the examples below.

EXAMPLES

Example 1

Compound 1-8

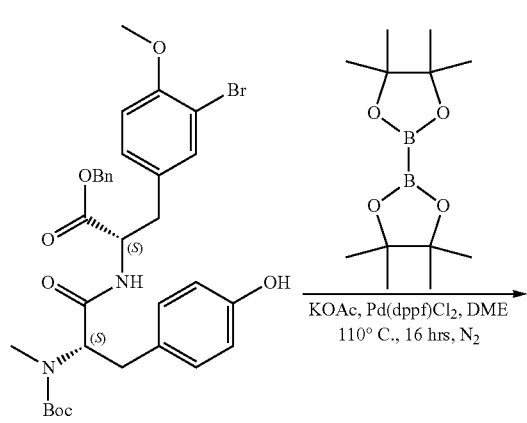

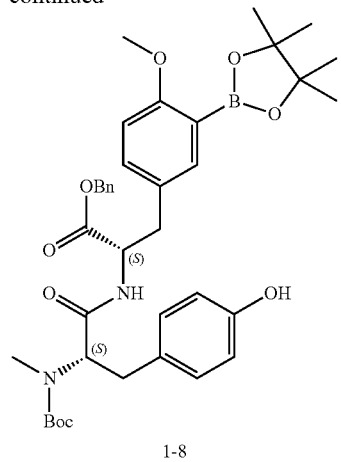

1-8

Compound 1-7 (40 g, 62.5 mmol, 1.0 eq), Bis(pinacolato)diboron (20.56 g, 81.25 mmol, 1.3 eq), KOAc (18.38 g, 187.5 mmol, 3.0 eq) and Pd(dppf)Cl$_2$ (2.28 g, 3.125 mmol, 0.05 eq) were suspended in DME (750 ml) and heated to 110° C. for 16 hrs under the protection of N$_2$. Water (500 ml) and EtOAc (500 ml) were added. The layers were separated, and the aqueous layer was extracted with EtOAc (2×500 ml). The combined organic layer was dried over anhydrous MgSO$_4$, filtered and concentrated. The residue was purified by column chromatography on silica gel using petro ether:EtOAc=2:1 to give compound 1-8 (31 g, 72% yield) as a white solid.

Example 2

Compound 1-9

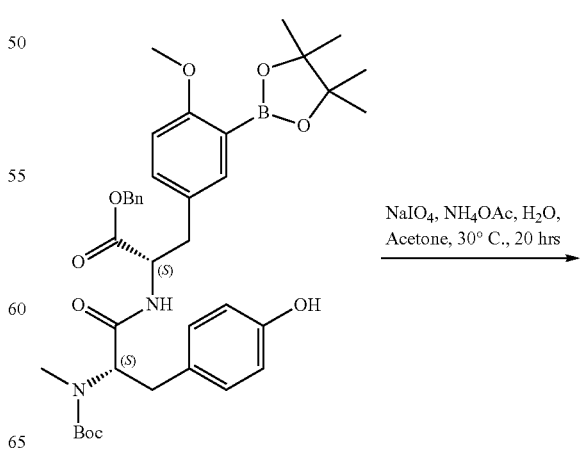

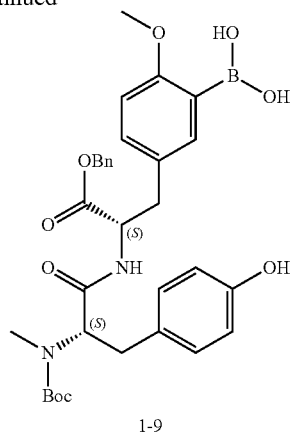

1-9

NH₄OAc (aqueous solution, 450 ml, 0.1 N) and NaIO₄ (28.93 g, 135 mmol, 3.0 eq) were added to a stirred solution of compound 1-8 (31 g, 45 mmol, 1.0 eq) in acetone (540 ml). The mixture was stirred at 30° C. for 20 hrs. The solvent was evaporated and the residue was dissolved in 500 ml of EtOAc, washed with 500 ml of 20% aqueous DL-Tartaric acid. The aqueous layer was extracted with EtOAc (2×500 ml). The combined organic layer was dried over anhydrous MgSO₄, filtered and concentrated. The residue was purified by column chromatography on silica gel using petro ether:EtOAc=2:1 to give compound 1-9 (16 g, 58.6% yield) as a white solid.

Example 3

Compound 1

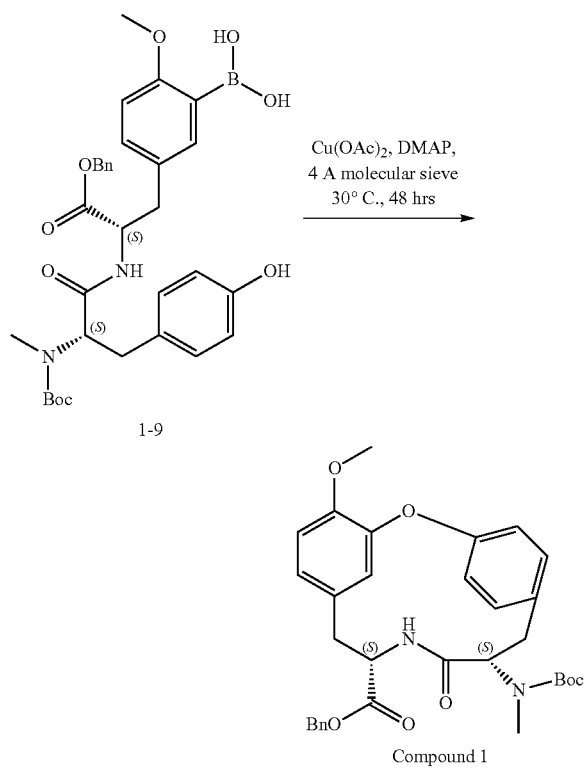

DMAP (2.135 g, 17.5 mmol, 5.0 eq) and powdered 4 Å molecular sieves (3.584 g) were added to a solution of compound 1-9 (2.121 g, 3.5 mmol, 1.0 eq) in anhydrous dichloromethane (200 ml). Then the reaction mixture was stirred at 30° C. for 30 min. Cu(OAc)₂ (0.8239 g, 4.55 mmol, 1.3 eq) was added to the mixture and the mixture was stirred at 30° C. for 48 hrs. The mixture was filtered and washed successively with 5% KHSO₄ (50 ml) and brine (50 ml), dried over anhydrous MgSO₄, filtered and concentrated. The residue was purified by column chromatography on silica gel using petro ether:EtOAc=2:1 to give compound 1 (0.49 g, 25% yield) as a white solid.

Example 4

Compound N-29-H RA-VII

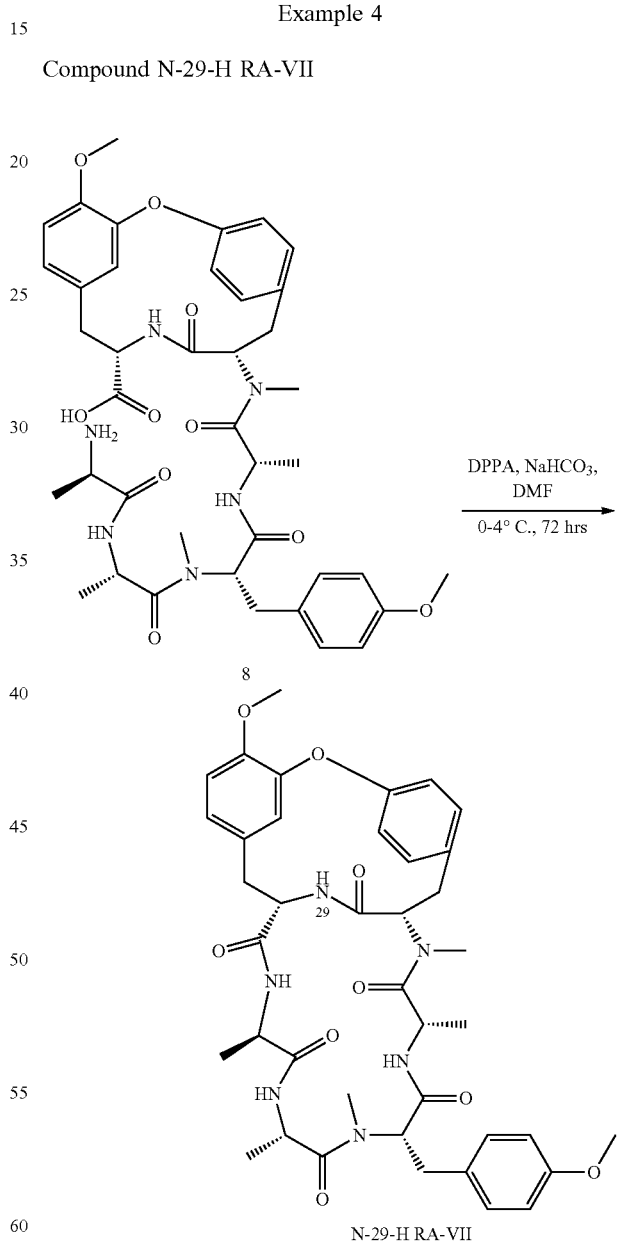

To a solution of compound 8 (29 mg, 37.5 umole, 1.0 eq.) in DMF (4.6 ml) was added DPPA (diphenyl phosphorazidate, 15.5 mg, 56.3 umole, 1.5 eq.) and NaHCO₃ (15.8 mg, 187.5 umol, 5.0 eq.) at 0° C., then the reaction mixture was stirred at 4° C. for 72 hrs. The reaction mixture was poured over cold water (9 ml), and extracted with EtOAc (3×9 ml). The organic phase were washed with water (9 ml), dried over anhydrous MgSO₄, and concentrated under reduced pressure. The residue was purified by preparative HPLC to give compound N-29-H RA-VII. Mass Spec.; 757.4 (M+1).

Example 5

Compound Meta Br-N-29-H RA-VII

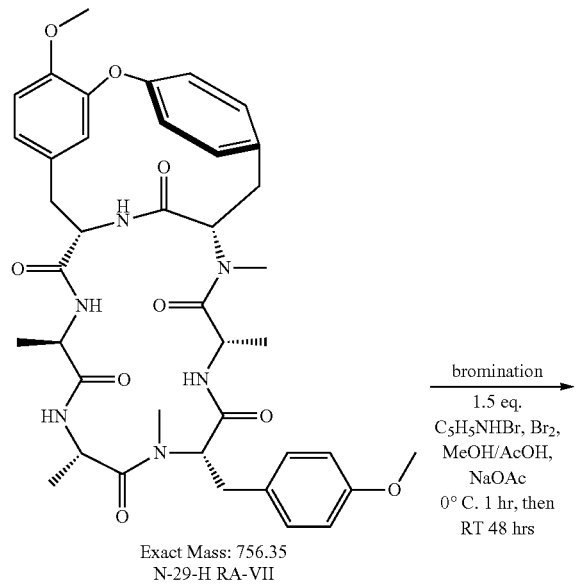

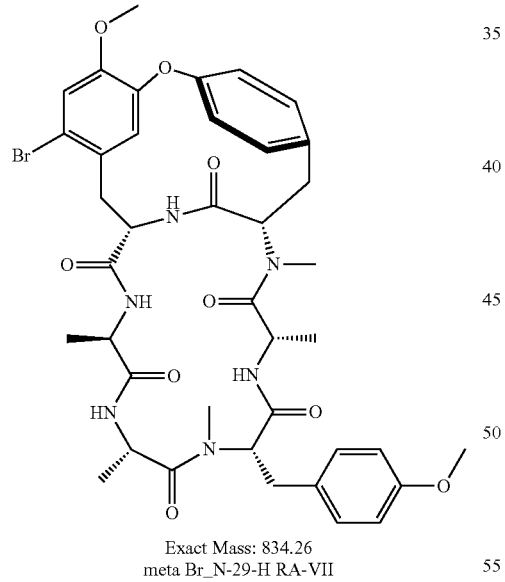

Sodium acetate (4.3 mg, 54.7 umol) and pyridinium hydrobromide perbromide (17.2 mg, 54.7 umol) were added to an ice-cooled solution of N-29-H RA-VII (23 mg, 30.4 umol) in 1.6 ml of mixed solvent MeOH/AcOH (V/V=1:1). The reaction mixture was stirred at 0° C. for 1 hr and then at room temperature for 48 hrs. The reaction mixture was then diluted with CHCl₃ (25 ml), washed sequentially with aqueous NaHSO₃ (5%, 6.4 ml) and brine (12.8 ml), and dried over Na₂SO₄. After filtration, the solvent was concentrated by reduced pressure. The residue was purified by Prep. HPLC to give pure meta Br-N-29-H RA-VII (16 mg, 62.9% yield). Mass Spec.; 835.3 (M+1).

Example 6

Compound Meta Cl-N-29-H RA-VII

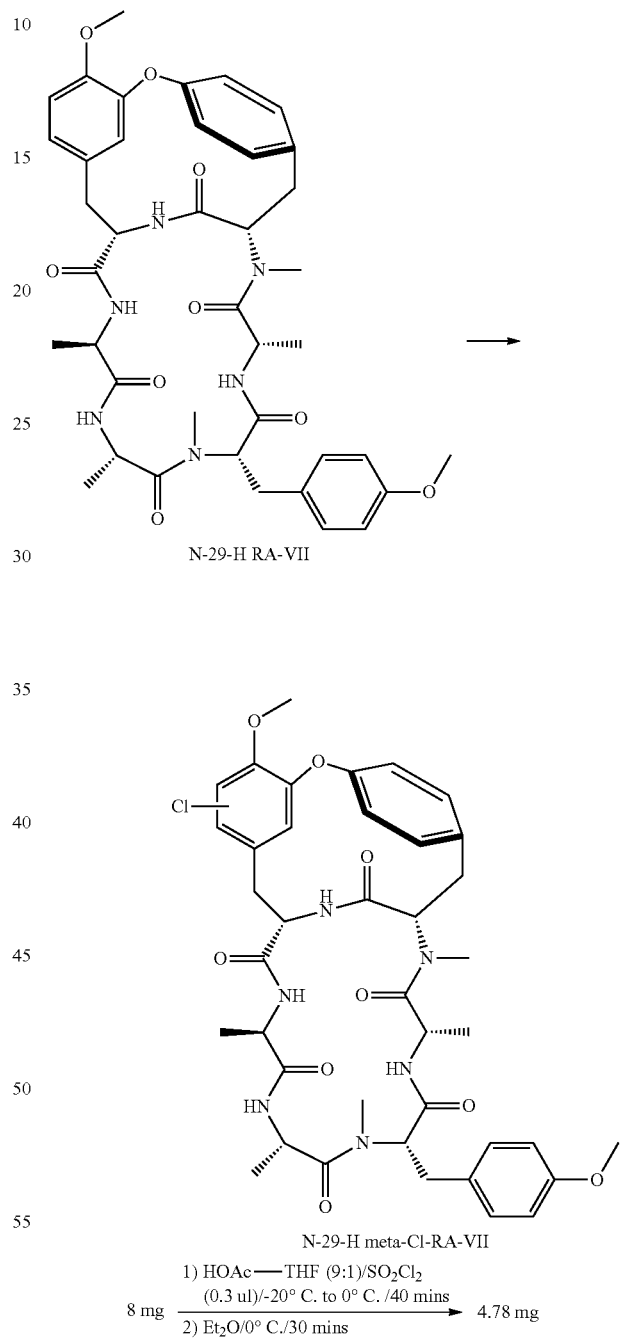

To a solution of N-29-H RA-VII (8 mg, 12 umol) in 600 ul HOAc/THF=9:1 was added SO₂Cl₂ (0.3 ul, 36 umol) in ice-bath, then stirred at −20° C. for 40 min, then 400 ul Et₂O was added into the mixture, and shaken at ice-bath for 30 min, the solvent was removed and the residue was purified by Prep HPLC to give pure Meta Cl-N-29-H RA-VII.

Example 7

Compound Meta CN-N-29-H RA-VII

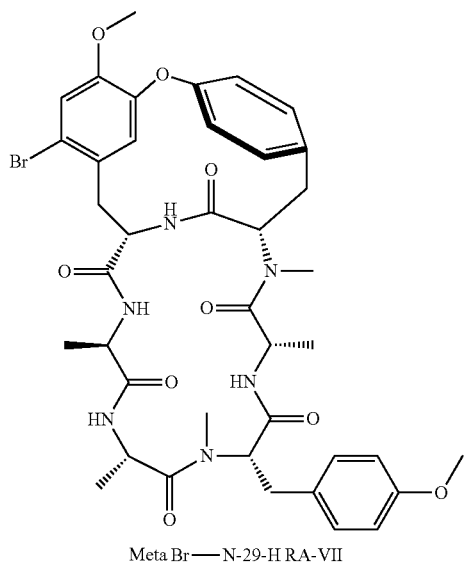

Meta Br—N-29-H RA-VII

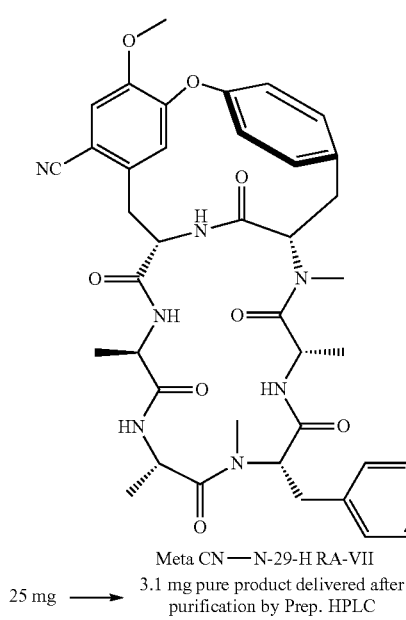

Meta CN—N-29-H RA-VII 25 mg → 3.1 mg pure product delivered after purification by Prep. HPLC To a solution of Meta-Br-N-29-H RA-VII (25 mg, 30 umol) in dry DMF (1 ml) was added CuCN (15 mg, 167 umol). The reaction mixture was stirred at 145° C. for 16 hrs. LC-MS showed the reaction was completed, the reaction mixture was filtered and concentrated to give crude product, which was purified by Prep HPLC to give the compound Meta-CN-N-29-H RA-VII (3.1 mg, 13.2% yield).

Example 8

Compound 3-2F

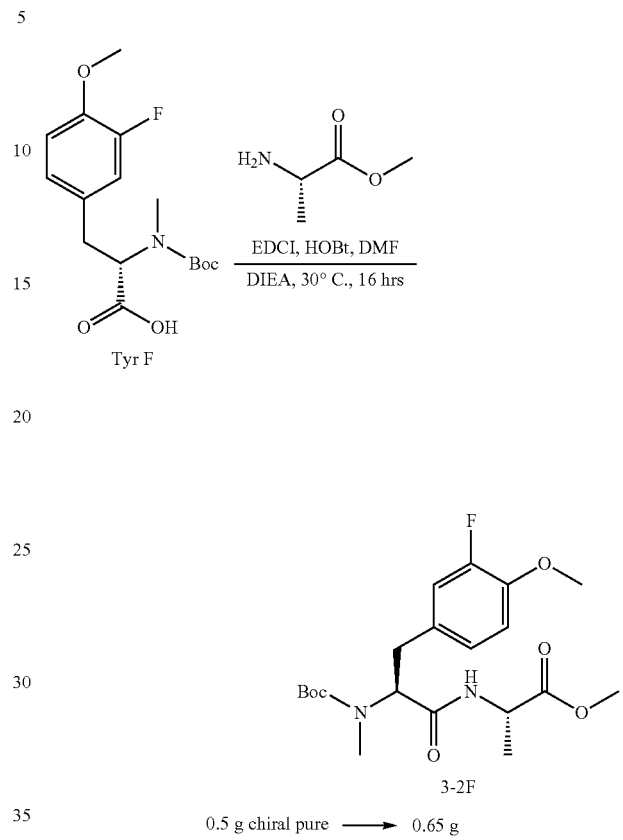

0.5 g chiral pure → 0.65 g

To a solution of Tyr-F (0.5 g, 1.53 mmol) in dry DMF (20 ml) was added (S)-methyl 2-aminopropanoate (154.5 mg, 1.53 mmol), HOPO (198 mg, 1.8 mmol), EDCI (429.8 mg, 2.25 mmol) and DIEA (290.2 mg, 2.25 mmol). The reaction mixture was stirred at room temperature for 20 hrs. LC-MS showed the reaction was completed. To the reaction mixture was added saturated aq. Na$_2$CO$_3$ and extracted with EtOAc, dried over MgSO$_4$, filtered and concentrated to give crude product 3-2F, which was used for nest step without purification. (0.65 g, 100% yield).

Example 9

Compound 3-3F

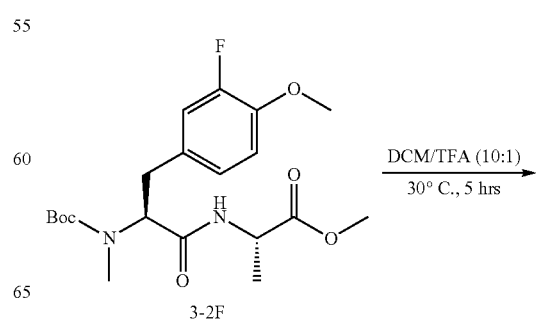

-continued

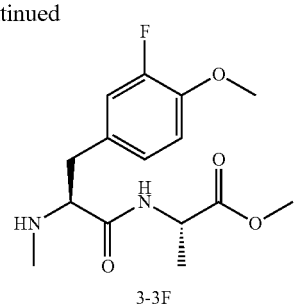

3-3F 0.65 g ⟶ 0.5 g

To a solution of compound 3-2F (0.65 g, 1.57 mmol) in DCM (20 ml) was added TFA (3 ml) and stirred at room temperature for 2 hrs. LC-MS showed the reaction completed. The solvent was removed under vacuum and the residue was added EtOAc, the mixture was washed with saturated aq. NaHCO₃, dried over MgSO₄, filtered and concentrated to give compound 3-3F (0.5 g, 74.6% yield) which was used for the next step without further purification.

Example 10

Compound 3F

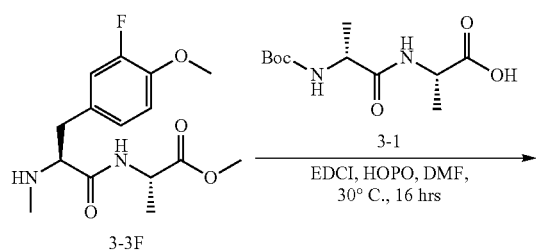

3-3F $\xrightarrow{\text{3-1}}_{\text{EDCI, HOPO, DMF,}}^{\text{30° C., 16 hrs}}$

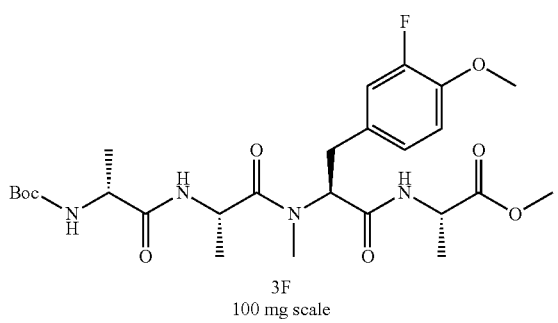

3F
100 mg scale 0.5 g ⟶ 0.475 g

To a solution of 3-3F (0.5 g, 1.1 mmol) in dry DMF (15 ml) was added compound 3-1 (286 mg, 1.1 mmol), HOPO (181.5 mg, 1.65 mmol), EDCI (315.2 mg, 1.65 mmol) and DIEA (212.8 mg, 1.65 mmol). The reaction mixture was stirred at room temperature for 20 hrs. LC-MS showed the reaction was completed. To the reaction mixture was added saturated aq. Na₂CO₃ and extracted with EtOAc, dried over MgSO₄, filtered and concentrated to give crude product compound 3F, which was purified by SFC to give chiral pure compound 3F (0.475 g, 78% yield).

Example 11

Compound 4F

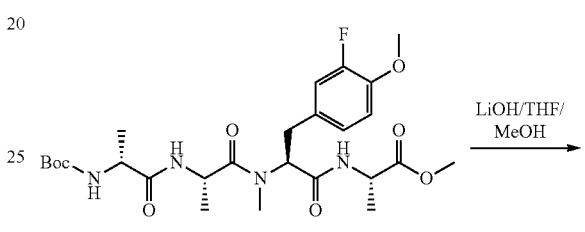

3F $\xrightarrow{\text{LiOH/THF/}}_{\text{MeOH}}$

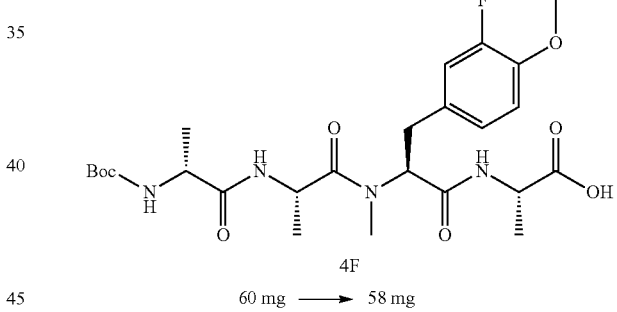

4F 60 mg ⟶ 58 mg

To a solution of compound 3F (60 mg, 0.11 mmol) in THF (3 ml) was added MeOH (1 ml), LiOH.H₂O (22 mg, 0.55 mmol) and water (1 ml). The reaction mixture was stirred at room temperature for 2 hrs. LC-MS showed the reaction completed. The solvent was removed under vacuum and the residue was added EtOAc and 10% aq. critic acid to pH=3-4, then extracted with EtOAc, dried over MgSO₄, filtered and concentrated to give compound 4F as white solid (58 mg, 98% yield) which was used for the next step without further purification.

Example 12

Compound 6F

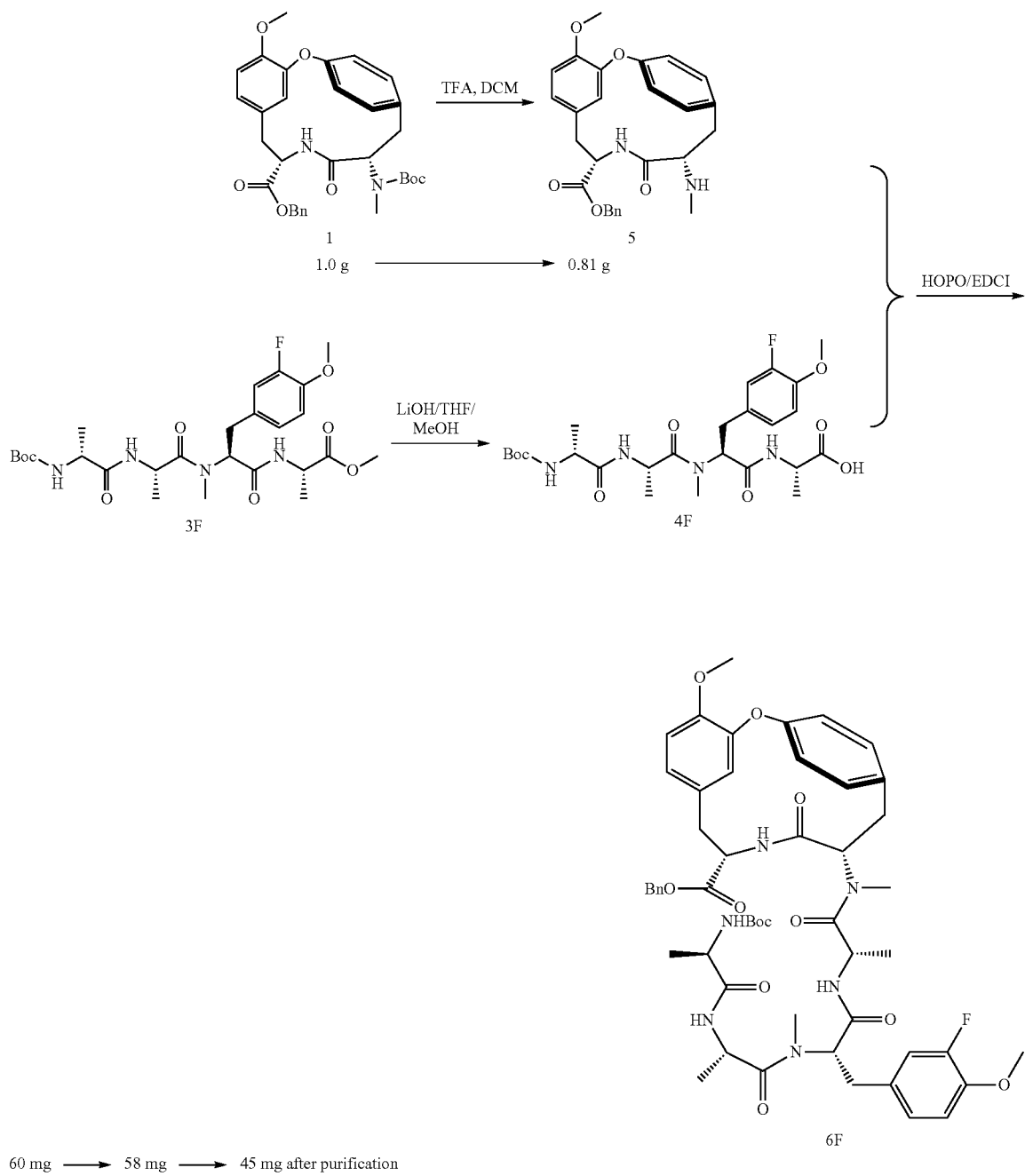

60 mg ⟶ 58 mg ⟶ 45 mg after purification

To a solution of compound 4F (58 g, 0.11 mmol) in dry DMF (5 ml) was added compound 5 (67.1 mg, 0.11 mmol), HOPO (18.5 mg, 0.165 mmol) and EDCI (31.5 mg, 0.165 mmol). The reaction mixture was stirred at room temperature for 20 hrs. LC-MS showed the reaction completed. To the reaction mixture was added saturated aq. $Na_2CO_3$ and extracted with EtOAc, dried over $MgSO_4$, filtered and concentrated to give crude product. The crude product was purified by Prep HPLC to give pure compound 6F (45 mg, 41.7% yield).

Example 13

Compound 7F

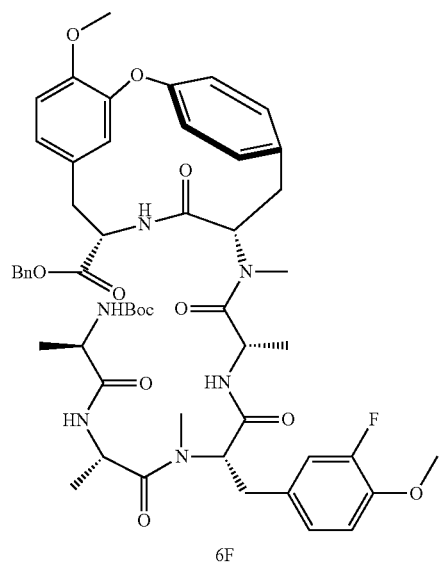

6F

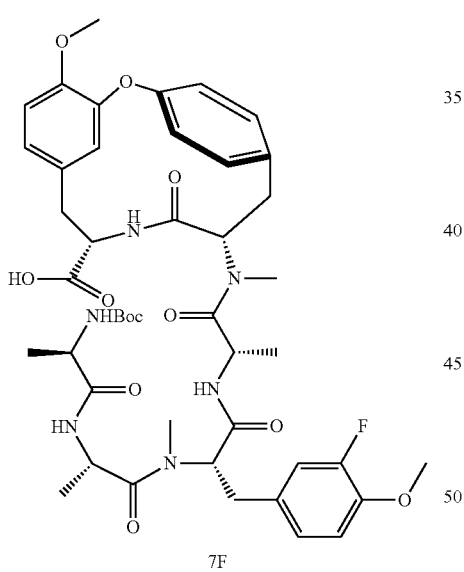

7F

To a solution of compound 6F (45 mg, 0.045 mmol) in MeOH (10 ml) was added Pd/C (10 mg, 10 wt %) under N₂ and stirred at room temperature for 10 hrs under H₂ (45 psi). LC-MS showed the reaction completed. The reaction mixture was filtered and concentrated to give compound 7F (40 mg, 97% yield) as white solid which was used for the next step without further purification.

Example 14

Compound 8F

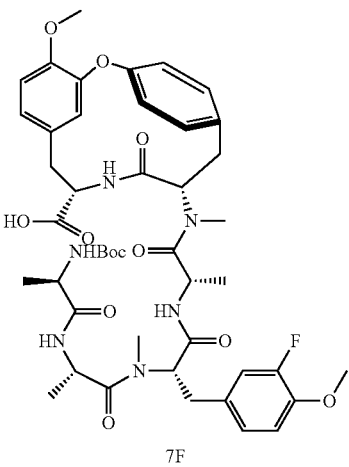

7F

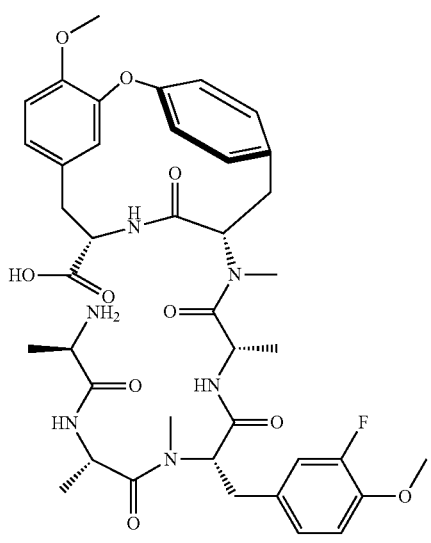

8F

To a solution of compound 7F (40 mg, 0.045 mmol) in DCM (6 ml) was added TFA (1 ml) and stirred at room temperature for 3 hrs. LC-MS showed the reaction completed. The solvent was removed to give compound 8F (45 mg, as TFA salt) which was used for the next step without further purification.

Example 15
Compound N-29-H-Tyr-F RA-VII
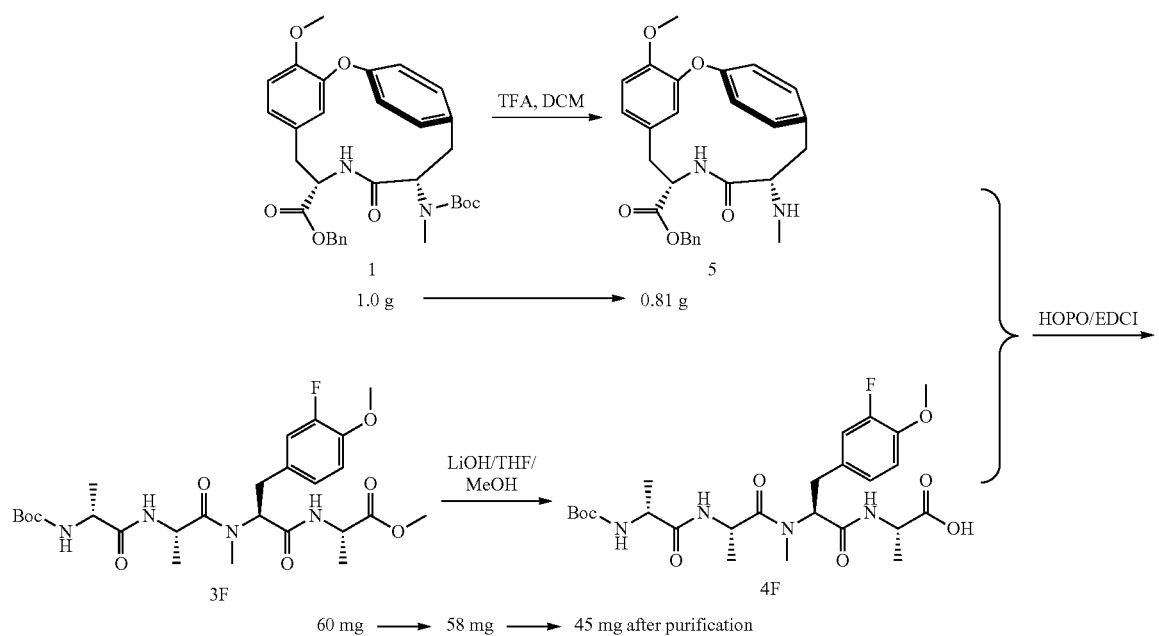
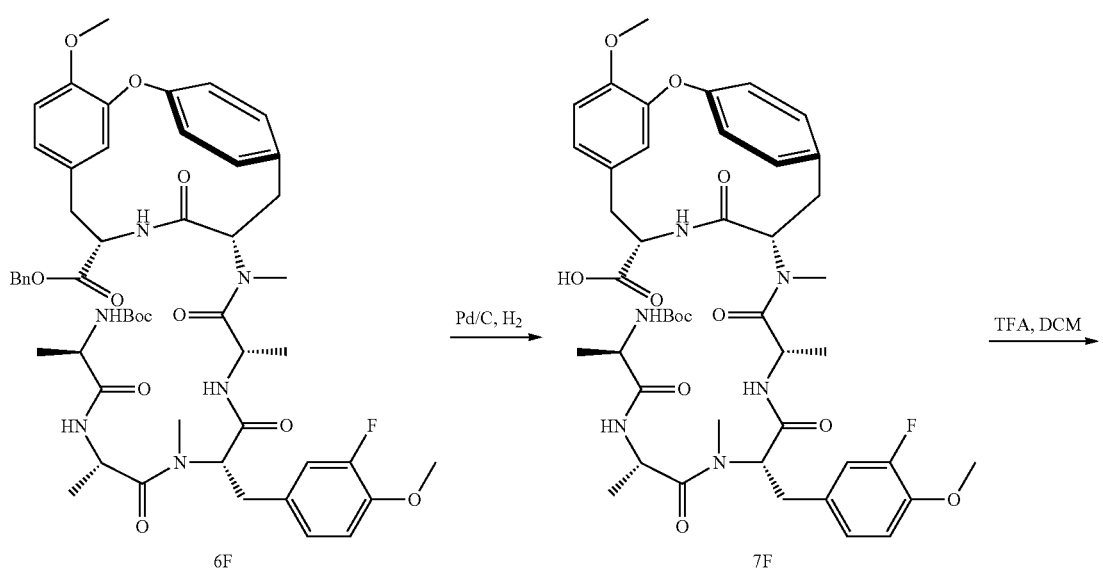

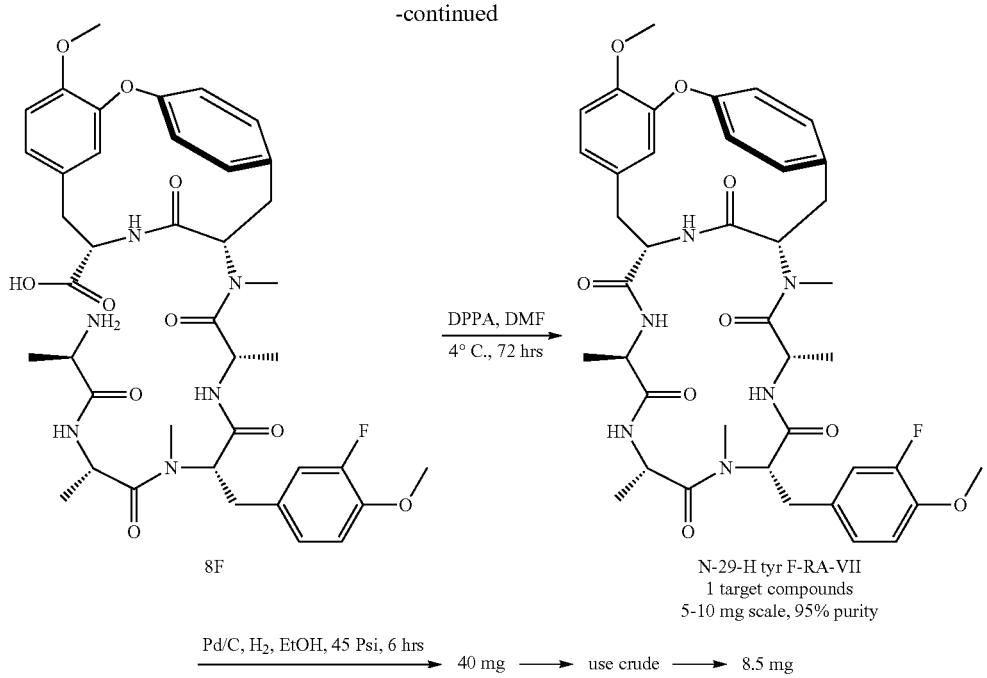

To a solution of compound 8F (45 mg TFA salt) in DMF (10 ml) was added DPPA (30 mg, 0.11 mmol) and NaHCO$_3$ (42 mg, 0.5 mmol) at 0° C., then the reaction mixture was stirred at 4° C. for 72 hrs. LC-MS showed the reaction completed. The reaction mixture was poured over cold water (10 ml), and extracted with EtOAc (3*20 ml), dried over MgSO$_4$, and concentrated under reduced pressure. The residue was purified by Prep. HPLC to give pure compound N-29-H-Tyr-F-RA-VII (8.5 mg, 25% yield).

Example 16

Figure 10:
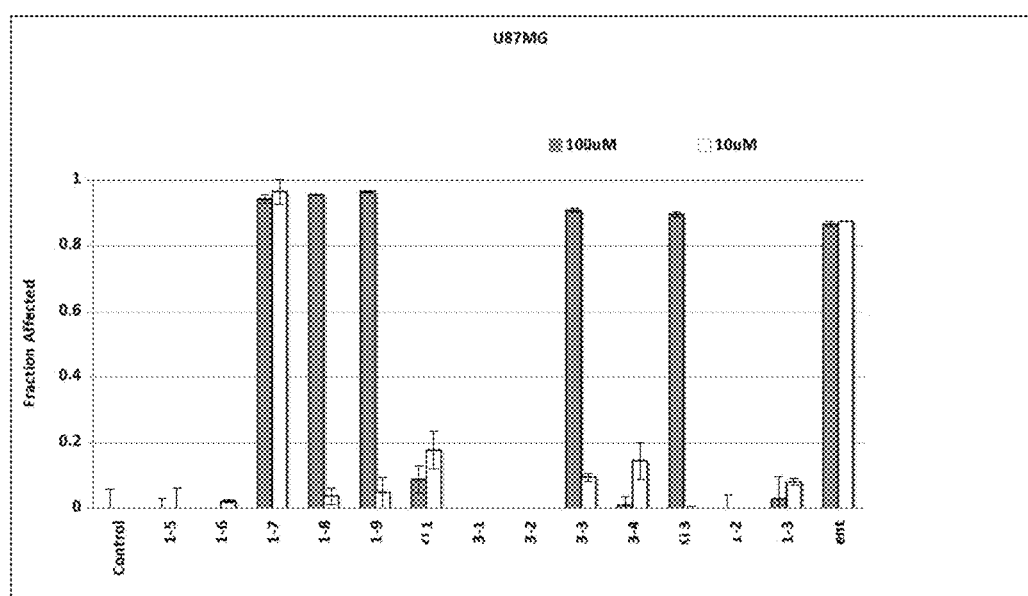
FIG. 10 depicts cell growth assay result of some compounds in FIGS. 4-6 as a single agent on U87MG glioma cells at 10 μM and 100 μM concentrations. The parent is bouvardin.
Figure 11:
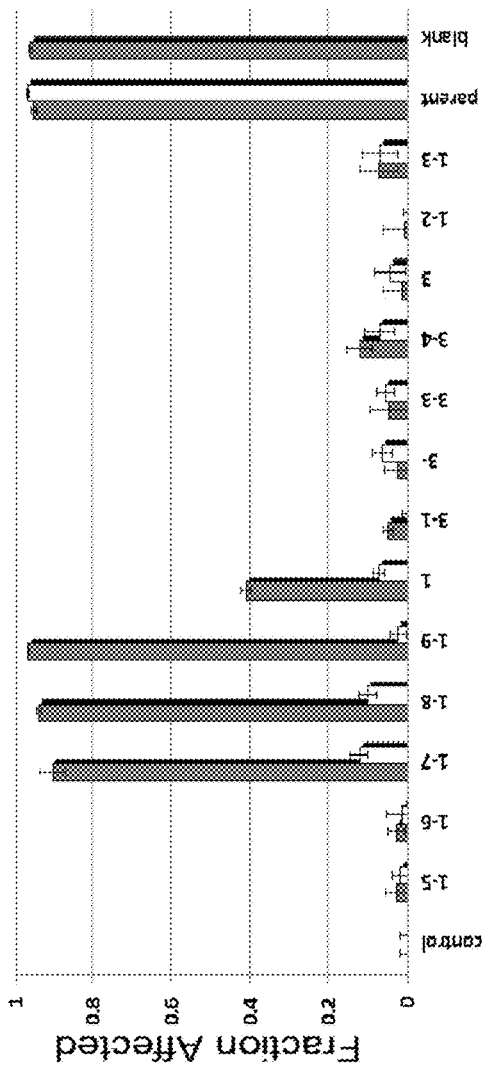
FIG. 11 depicts cell growth assay result of some compounds in FIGS. 4-6 as a single agent on T98G glioma cells at 10 μM and 100 μM concentrations. The parent is bouvardin.

Experimental Details for FIGS. 10 and 11 (Cell Growth Assay)

Two glioma cell lines were used (U87MG and T98G). The growth inhibitory effects of chemical compounds were evaluated using CellTiter-Glo® Luminescent Cell Viability Assay (Promega G7570). The CellTiter-Glo® Reagent lyses cells and generates a luminescent signal proportional to the amount of ATP present. In this assay, 4,000 viable cells were plated in 100 μL of growth medium in 96-well plates (Corning). Following an overnight incubation, drugs were added in varying concentrations and incubated for 6 days. 100 μL of CellTiter-Glo® Reagent was added to each well. Plates were incubated with mixing at room temperature for 30 minutes. Luminescence of each well was measured using an automated plate reader.

Compound 1-7, 1-8, and 1-9 showed potent inhibitory effects against both U87MG and T980 glioma cell lines as a single agent (data shown in FIGS. 10 and 11). However, these compounds do not appear to inhibit protein translation in our in vitro translation assay (data not shown).

Example 17

Figures 12, 13:
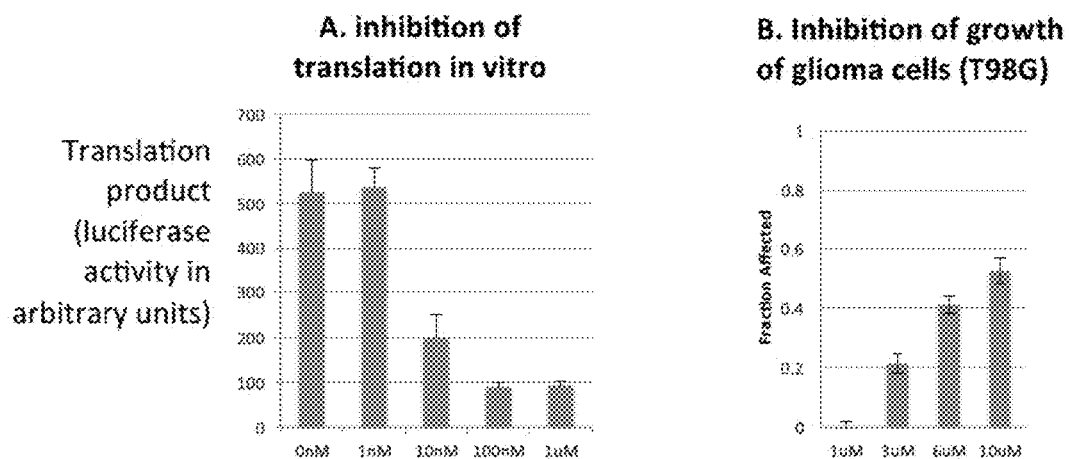
FIG. 12 depicts that meta Br-N-29-H RA-VII inhibits translation and growth of T98G glioma cells in vitro.
FIG. 13 depicts the IC50 values for Bouvardin derivatives N-29-H RA-VII, meta Br-N-29-H RA-VII, meta CN-N-29-H RA-VII, meta Cl-N-29-H RA-VII, and N-29-H tyr-F-RA-VII on human cancer cell lines.
Figure 14A:
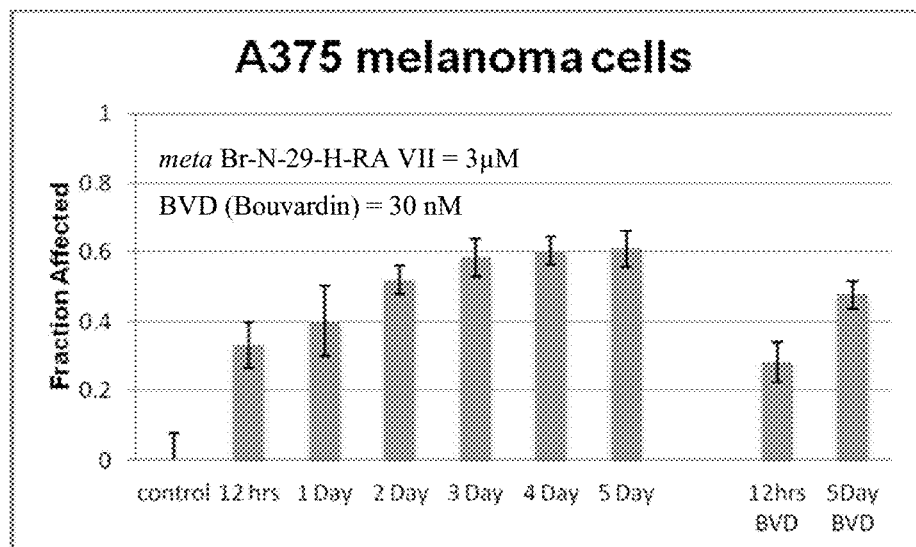
FIG. 14A-14G depict that meta Br-N-29-H RA-VII and meta Cl-N-29-H RA-VII show efficacy after being exposed to cells for various lengths of time.
Figure 14B:
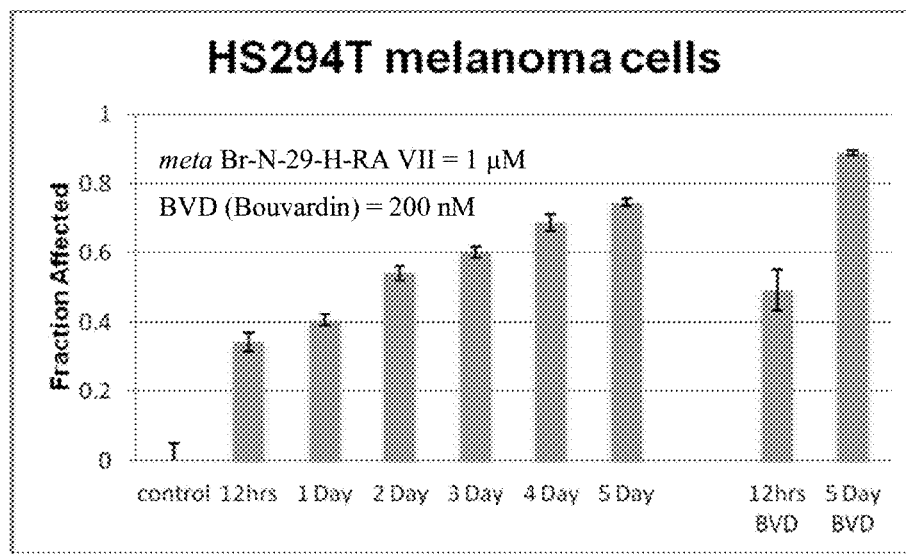
Figure 14C:
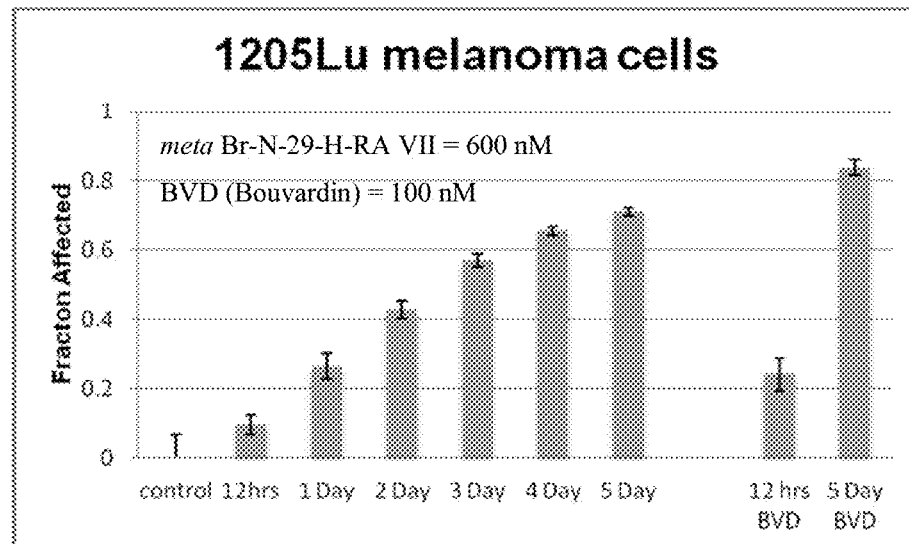
Figure 14D:
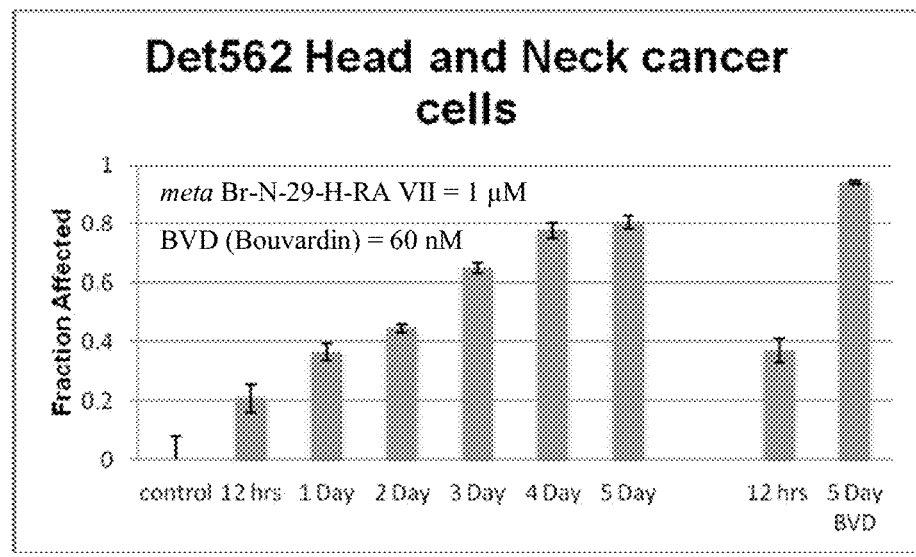
Figure 14E:
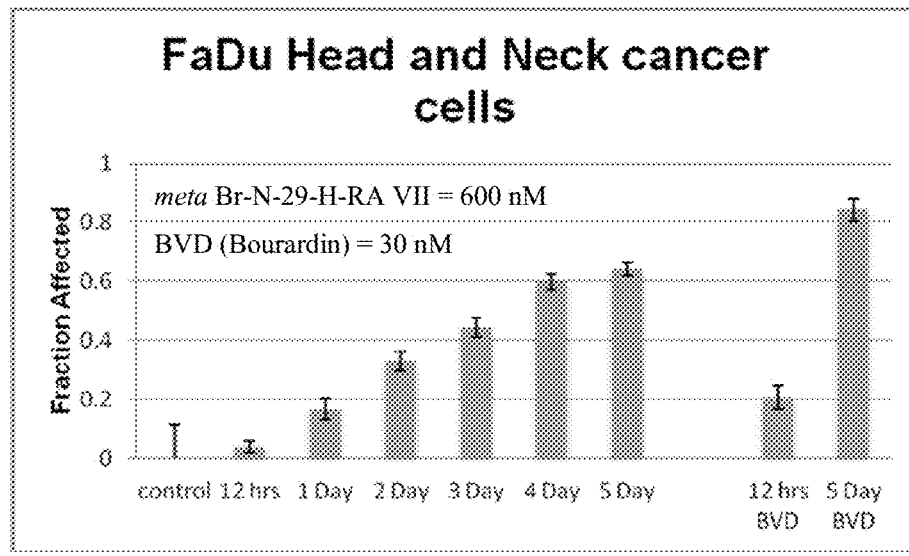
Figure 14F:
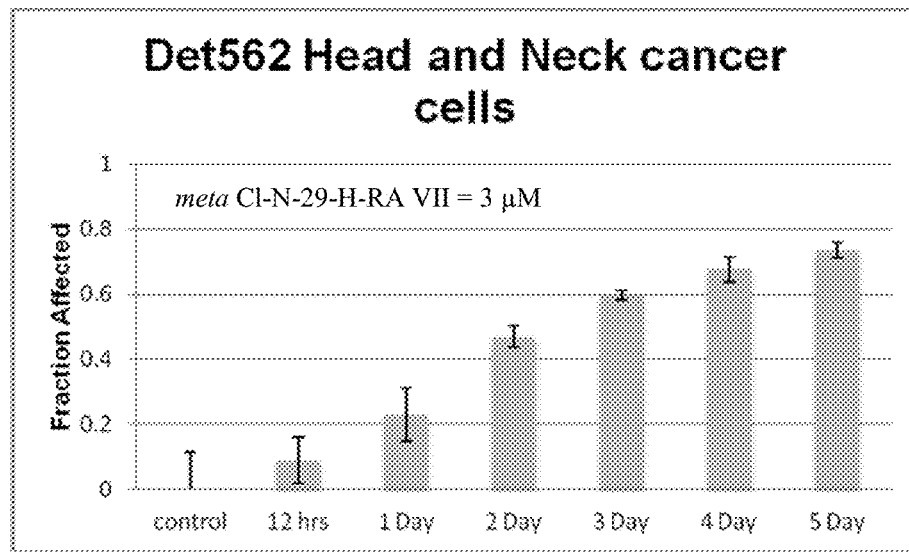
Figure 14G:
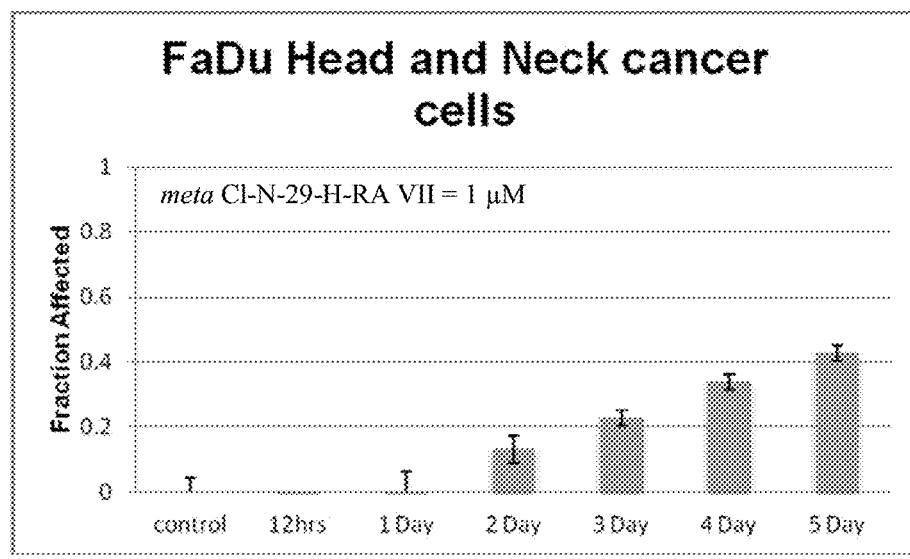
Figure 15:
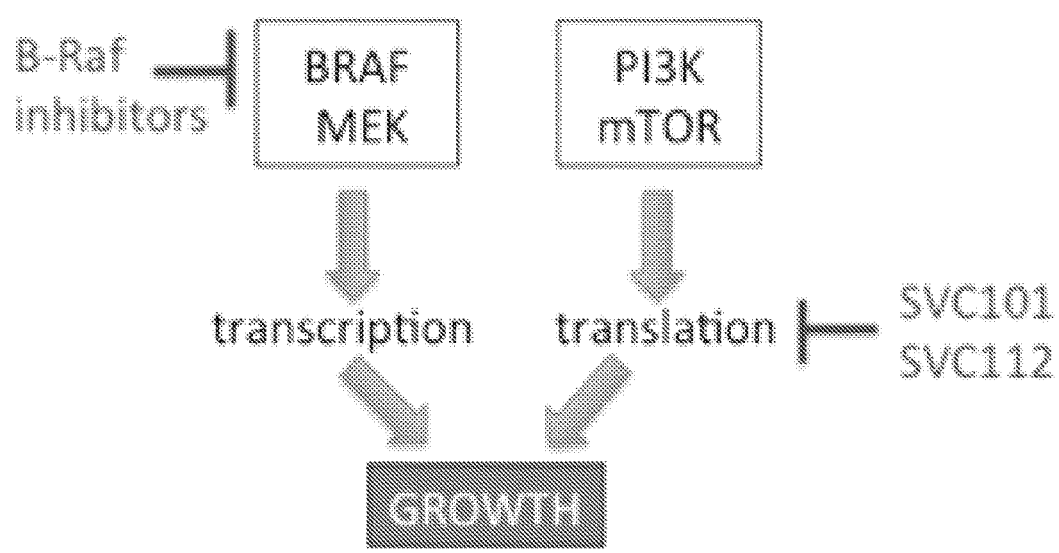
FIG. 15 depicts the rationale for synergy between Bouvardin analogs (and related compounds) and targeted agents. Inhibition of pathways that make independent contribution to growth may be expected to provide synergy. Because P13K/TOR makes contribution to growth besides through translation, inhibitors of P13K/TOR may also be expected to synergize with Bouvardin analogs (and related compounds).

Experimental Details for FIG. 12 (In Vitro Translation Assay)

In vitro translation assays were performed in rabbit reticulocytes (Promega) according to manufacturer's instruction, in the presence or absence of drug at final concentrations shown. Luciferase mRNA provided in the kit was used at a final concentration of 1 μg/μl. The reaction samples were incubated for 15 minutes at 37° C. and quenched by dilution with water. Luciferase activity was measured using a plate reader Multi-Mode Microplate Reader (Synergy 2 by BioTek) immediately after luciferase substrate addition.

As shown in FIG. 12, meta Br-N-29-H RA-VII displayed dose-dependent response in both translation assay and cell growth assay with T98G glioma cells.

Example 18

Experimental Details for FIG. 13 (IC50 Values for Bouvardin Derivatives on Human Cancer Cell Lines)

Seven cell lines, lung cancer cell line H157, HNC cell lines Det562 and FaDu, and melanoma cell lines WM35, A375, 1205Lu and HS294T were studied. The growth inhibitory effects of chemical compounds were evaluated using CellTiter-Glo® Luminescent Cell Viability Assay (Promega G7570). The CellTiter-Glo® Reagent lyses cells and generates a luminescent signal proportional to the amount of ATP present. In this assay, ~4,000 viable cells were plated in 100 μL of growth medium in 96-well plates (Corning). Following an overnight incubation, drugs were added in varying concentrations and incubated for 6 days. 100 μL of CellTiter-Glo® Reagent was added to each well. Plates were incubated with mixing at room temperature for 30 minutes. Luminescence of each well was measured using an automated plate reader. Survival was plotted against drug concentration to compute IC50.

Example 19

Experimental Details for FIG. 14A-14F (Meta Br-N-29-H RA-VII and Meta Cl-N-29-H RA-VII Show Efficacy after being Exposed to Cells for Various Lengths of Time.)

The cell growth assays used to measure IC50 and synergy involve leaving the drug on the cells for 5 days. However, this length of time may or may not be necessary to see efficacy. To address this, two Bouvardin derivatives (meta Br-N-29-H RA-VII and mera Cl-N-29-H RA-VII) were exposed to different melanoma and head and neck cells for various amounts of time. Cells were plated at 4,000 cells per well in 96 well plates and allowed to adhere for 24 hrs before adding meta Br-N-29-H RA-VII or meta Cl-N-29-H RA-VII at an IC70 concentration for each cell line. The drug was removed after various times (12 hr, 1 day, 2 days, 3 days, 4 days) by replacement with fresh media. After 5 days, cell viability was determined using CellTiter-Glo® Luminescent Cell Viability Assay (Promega G7570), which measures ATP levels. Bouvardin or BVD at 12 hr exposure was used as a control. Each melanoma line showed partial response at 12 hr exposure and reached maximal response (same as 5 day) at various days: A375 2-3 days, HS294T 3-4 days, and 1205Lu at 4 days. Of the Head and Neck cancer cell lines, Det562 cells show partial response at 12 hr and maximal response at 4 days while FaDu cells show no response at 12 hr and maximal response at 4 days. While the maximal effect of meta Br-N-29-H RA-VII was not reached at the same time for all of the lines, the drug is affecting each cell line to some degree by 24 hrs.

These same timing experiments were also performed using meta Cl-N-29-H RA-VII on the Head and Neck cancer cell lines, the cell type they were the most effective on. It was found that meta Cl-N-29-H RA-VII showed similar timing for effectiveness as meta Br-N-29-H RA-VII. These data are encouraging for the eventual use of meta Br-N-29-H RA-VII (and possibly meta Cl-N-29-H RA-VII) in a clinical setting.

Example 20

Bouvardin and Meta Br-N-29-H RA-VII

The ability of bouvardin and meta Br-N-29-H RA-VII to inhibit the growth of Melanoma cells in culture was studied. Similar to the other cell types, meta Br-N-29-H RA-VII is 5 to 10 times less effective (greater IC50) than bouvardin on Melanoma cells. Both compounds show greater efficacy in higher grade, metastatic melanoma cell lines than in a lower grade melanoma line. For example, the IC50 of bouvardin on A375 (higher grade) and WM35 (lower grade, radial phase) cell lines are 12 nM and 124 nM respectively. meta Br-N-29-H RA-VII shows a similar pattern with IC50 of 100 nM and 1.17 uM for A375 and WM35 cell lines, respectively. These data are in agreement with a published report that bouvardin has a higher IC50 (lower efficacy) in primary human cells than in transformed cells (Dolma et al., 2003). These data suggest that our drug candidates show specificity for more aggressive cell lines.

Figure 17:
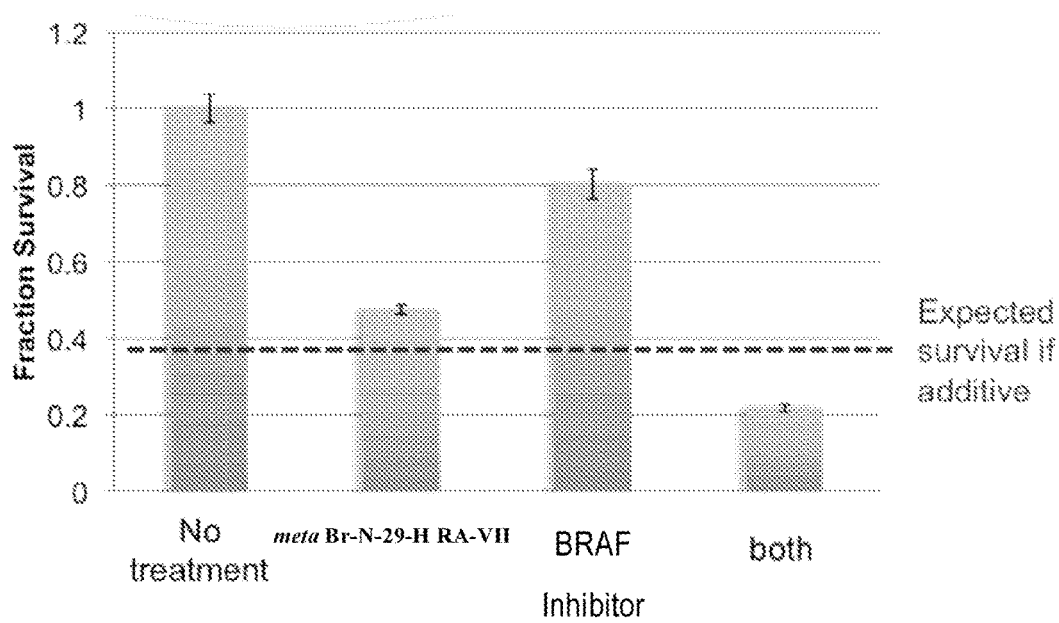
FIG. 17 shows meta Br-N-29-H RA-VII and PLX4032, a BRAF inhibitor, synergize on HS294T metastatic melanoma cells. The dotted line indicates fraction survival expected if meta Br-N-29-H RA-VII and PLX4032 are act in an additive manner. The observed effect of the combination is lower, indicating synergy. This represents a subset of a larger data set that includes the result of a wide range of drug doses. The complete dataset is in FIGS. 18 and 19.
Figure 18:
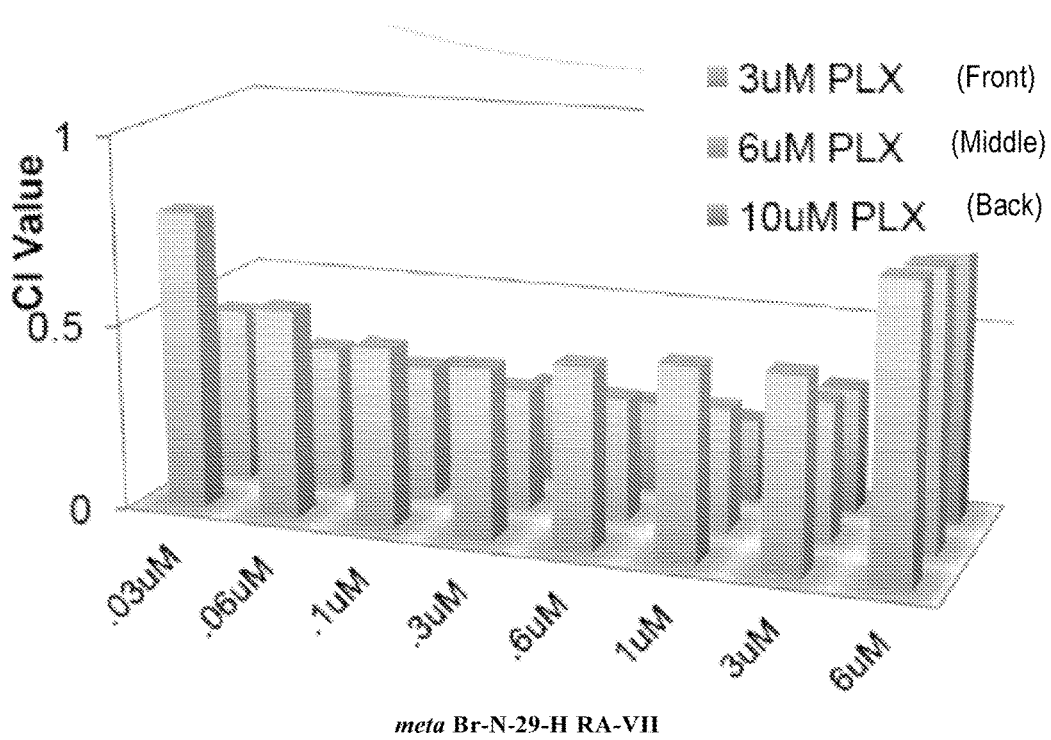
FIG. 18 shows meta Br-N-29-H RA-VII and PLX4032, a BRAF inhibitor, synergize on HS294T metastatic melanoma cells. The graph shows combination index (CI), which is a measure of how two agents interact. CI of less than 1 indicates synergy, which is seen for a wide range of drug concentrations.
Figure 19:
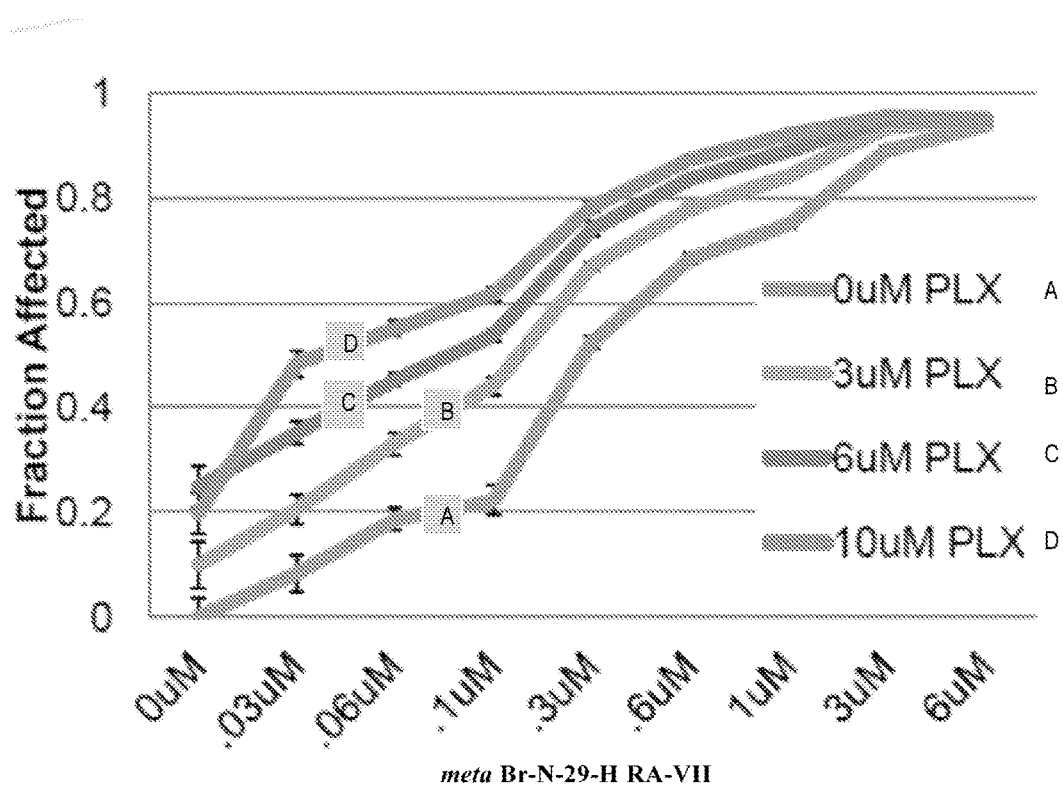
FIG. 19 shows the fraction of cells killed or inhibited from growth at the same concentrations of drug used in the CI graph (FIG. 18). This illustrates that at doses that show synergy, significant fractions of cells are killed or inhibited from growing.

Drug candidates in combination with standard agents were also studied. meta Br-N-29-H RA-VII shows synergy with inhibitors of oncogenic mutant BRAF ('BRAF inhibitors'), which are of increasing importance in treatment for melanoma (FIG. 17). meta Br-N-29-H RA-VII synergizes best and over a wide range of meta Br-N-29-H RA-VII doses with Vemurafenib (PLX4032. FIGS. 17, 18 and 19). Synergy is seen in cell lines with a wide range of sensitivity to PLX4032, i.e. both PLX4032-sensitive and PLX4032-resistant lines. These data suggest that bouvardin, meta Br-N-29-H RA-VII, and related compounds will be useful in combination with BRAF inhibitors in a clinical setting.

FIG. 17 shows that meta Br-N-29-H RA-VII and PLX4032, a BRAF inhibitor, synergize on HS294T metastatic melanoma cells. The dotted line indicates fraction survival expected if meta Br-N-29-H RA-VII and PLX4032 are act in an additive manner. The observed effect of the combination is lower, indicating synergy. This represents a subset of a larger data set that includes the result of a wide range of drug doses. The complete dataset is in FIGS. 16 and 17.

FIGS. 18 and 19 show that meta Br-N-29-H RA-VII and PLX4032, a BRAF inhibitor, synergize on HS294T metastatic melanoma cells. The graph on the left shows combination index (CI), which is a measure of how two agents interact. CI of less than 1 indicates synergy, which is seen for a wide range of drug concentrations. For comparison, a targeted therapy approved for use with radiation, Cetuximab, shows CI values of ~0.5 with radiation (Raben et al., Clinical Cancer Research, 2005, which is incorporated herein by reference). The graph on the right shows the fraction of cells killed or inhibited from growth at the same concentrations of drug used in the CI graph. This illustrates that at doses that show synergy, significant fractions of cells are killed or inhibited from growing.

Figure 20:
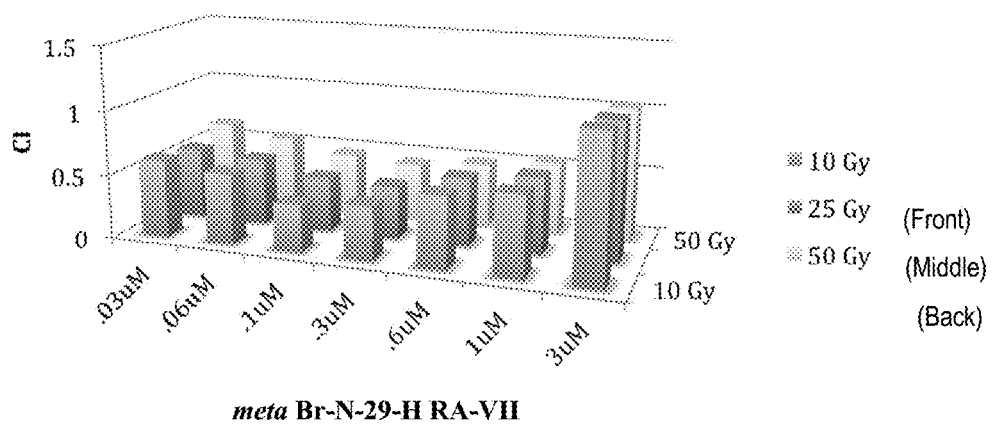
FIG. 20 depicts that meta Br-N-29-H RA-VII and ionizing radiation synergizes on HS294T melanoma cells. CI values are shown for a range of drug doses and radiation. CI<1 indicates synergy.

Compound meta Br-N-29-H RA-VII also shows synergy with ionizing radiation, another agent commonly used in treatment of melanoma (FIG. 20). FIG. 20 shows that meta Br-N-29-H RA-VII and ionizing radiation synergizes on HS294T melanoma cells. CI values are shown for a range of drug doses and radiation. CI<1 indicates synergy.

Figure 21:
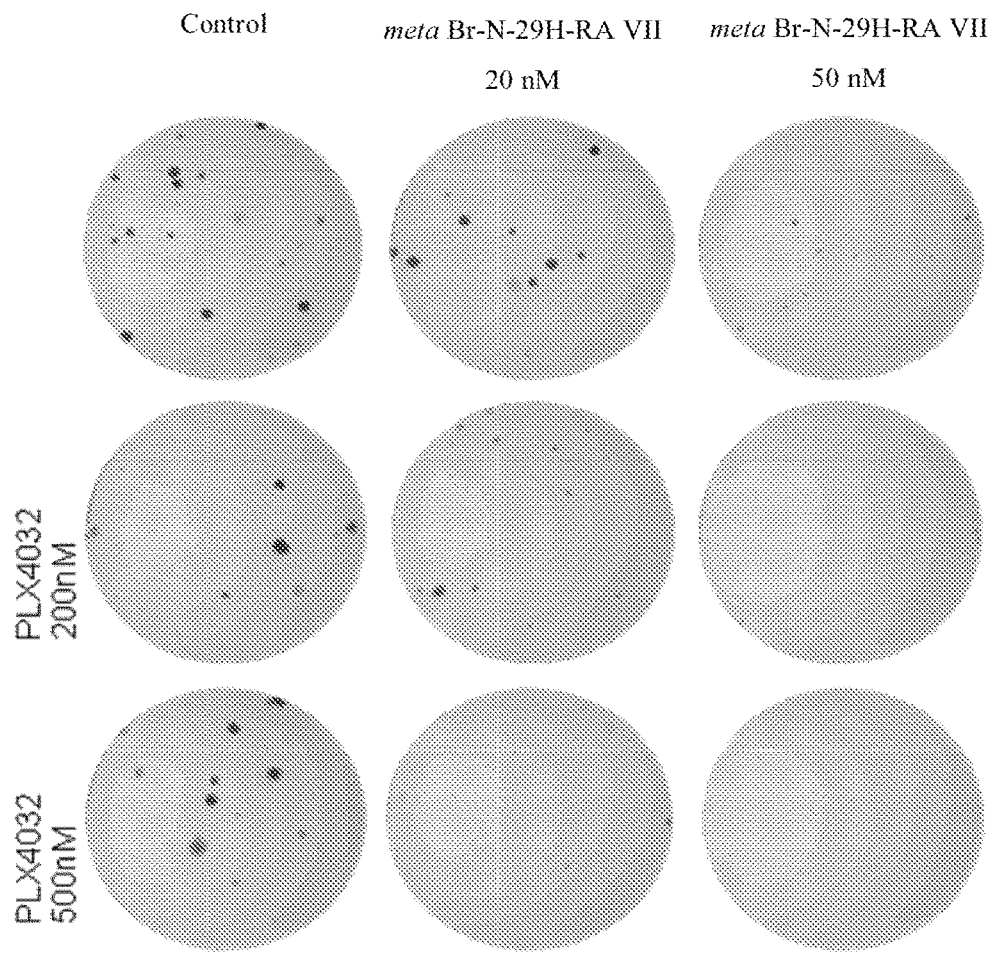
FIG. 21 depicts that meta Br-N-29-H RA-VII synergizes with the BRAF inhibitor PLX4032 in clonogenic assays.
Figure 23:
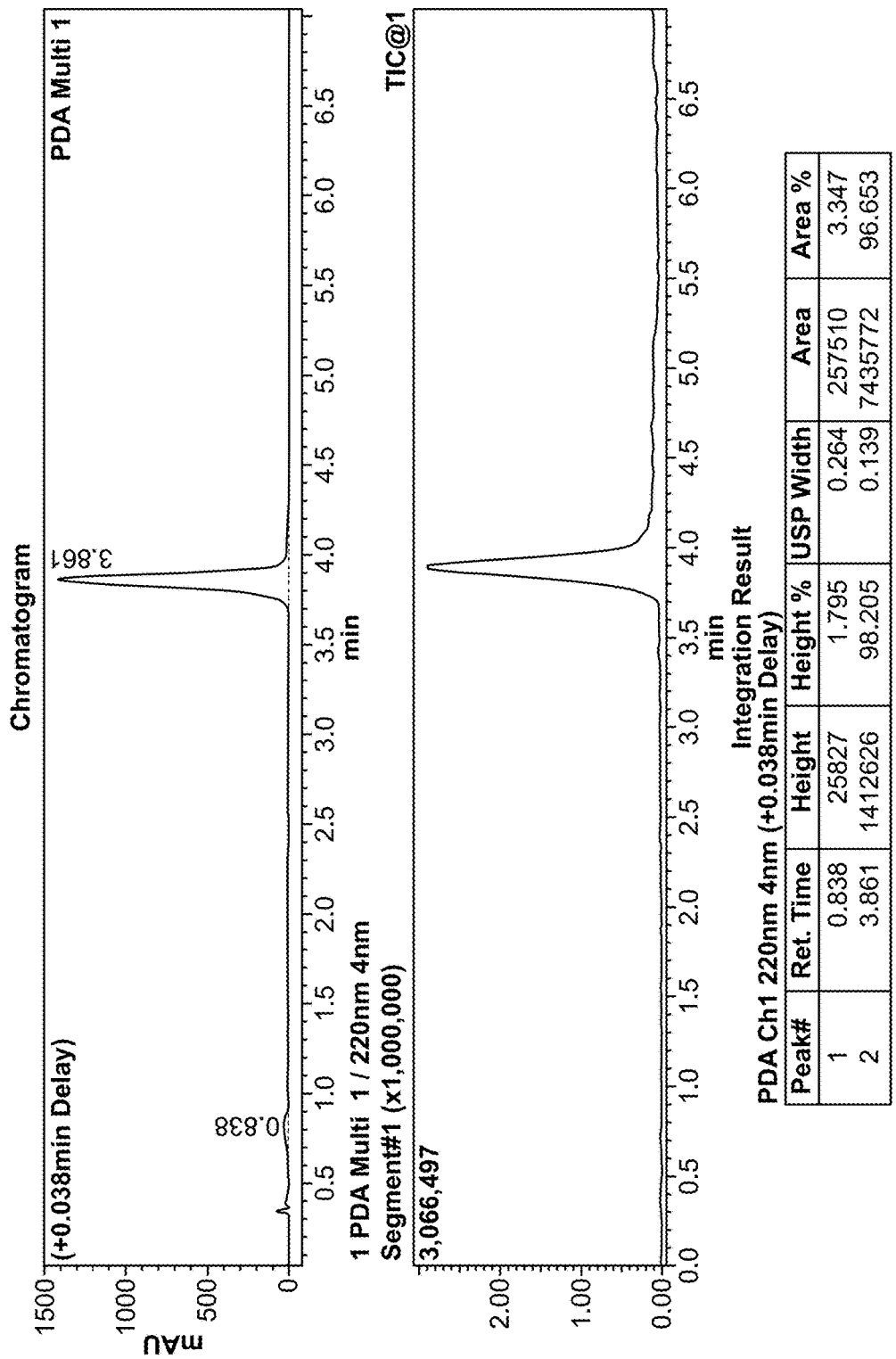
FIG. 23-24 show the LCMS report of meta Cl-N-29-H RA-VII.
Figure 24:
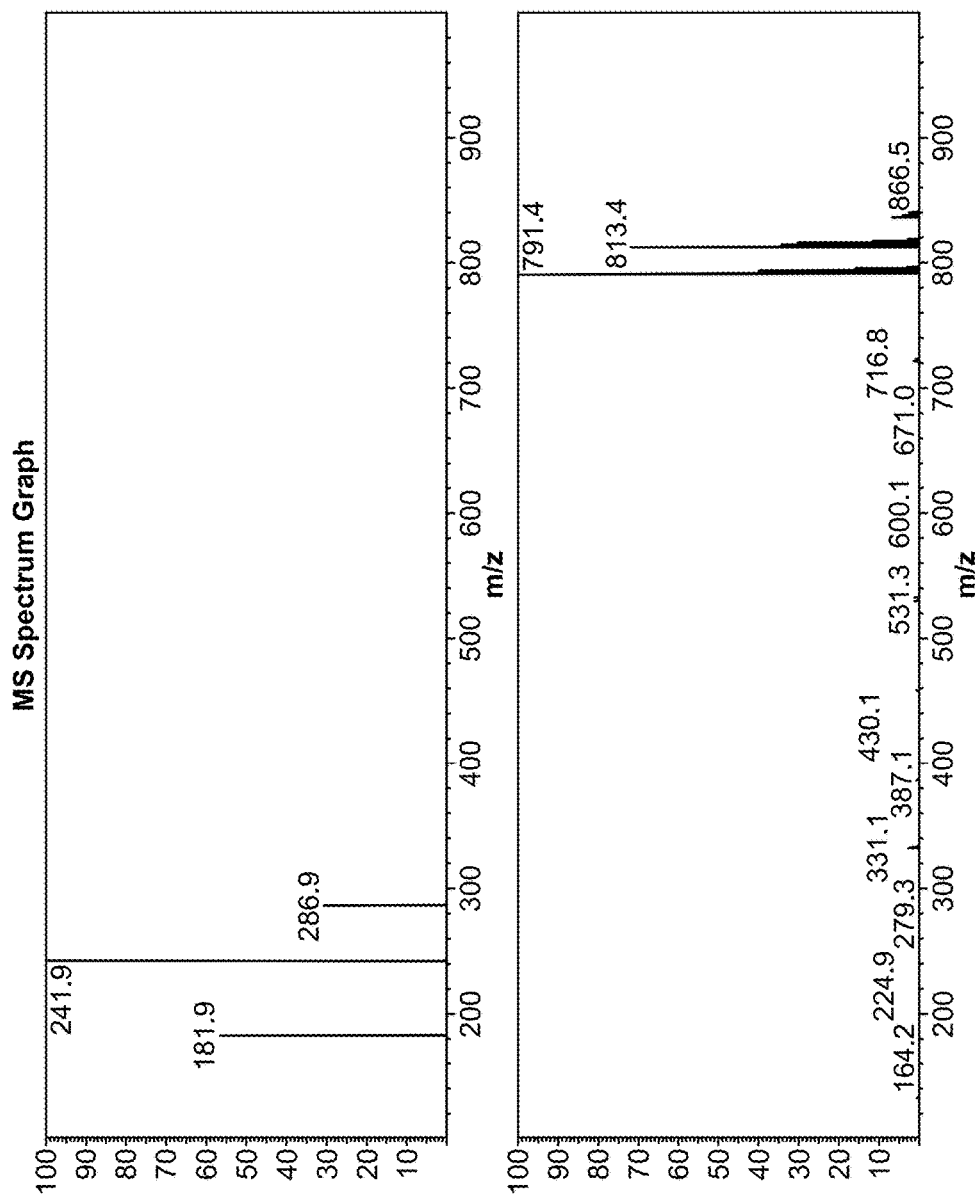
Figure 25:
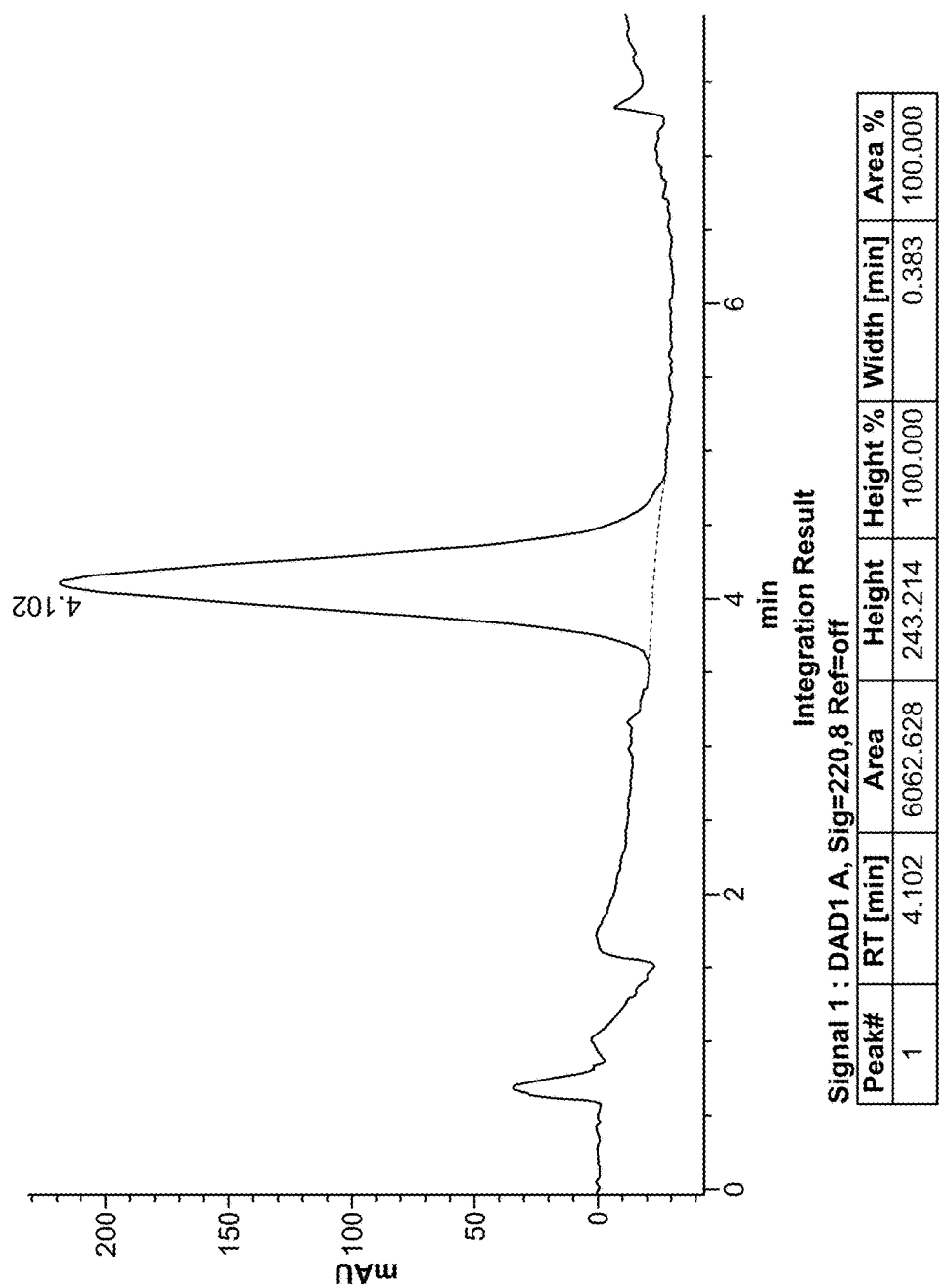
FIG. 25 shows the SFC(supercritical fluid chromatography)-MS report of meta Cl-N-29-H RA-VII.
Figure 26:
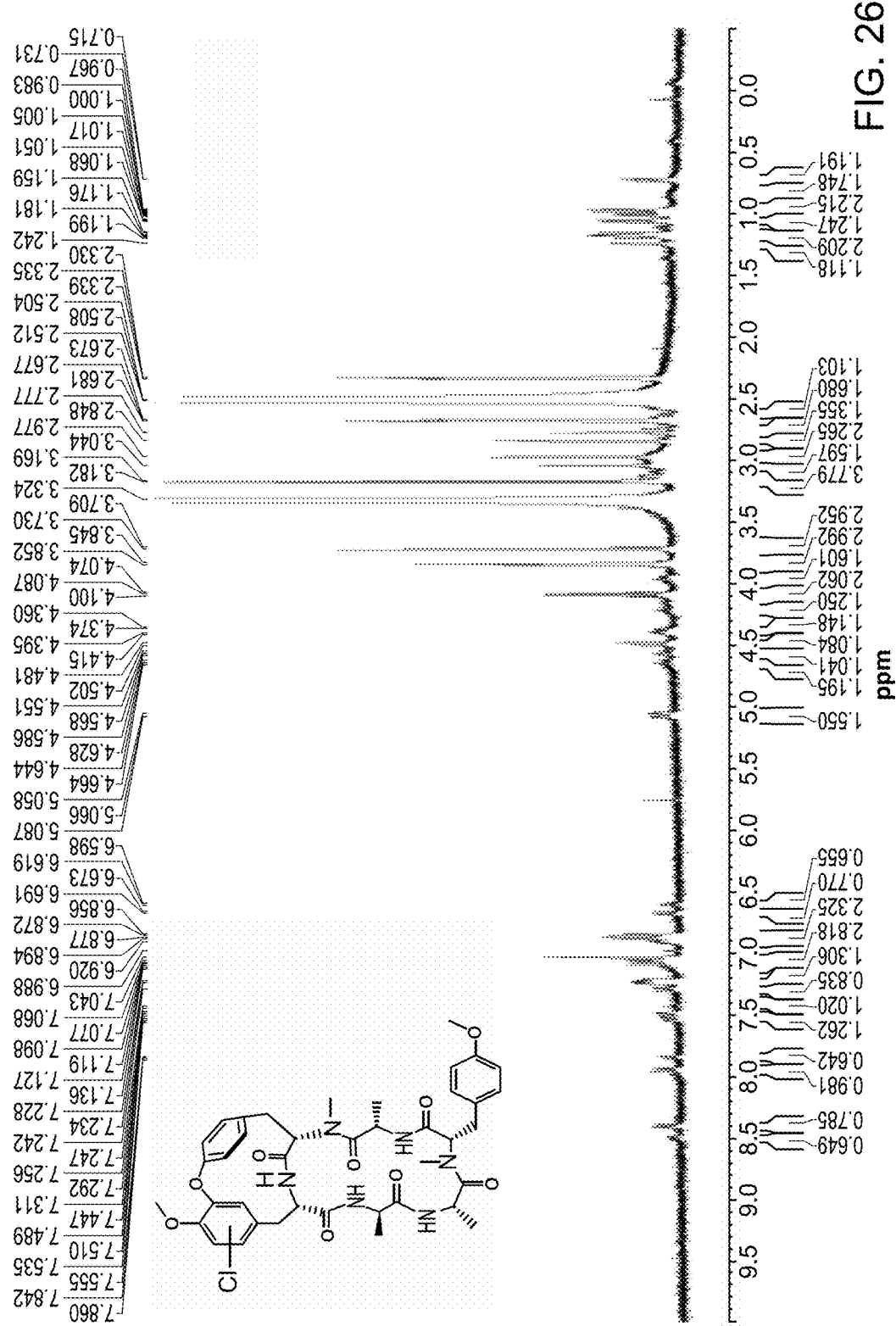
FIG. 26 shows the $^1$H NMR spectrum of meta Cl-N-29-H RA-VII.
Figure 27:
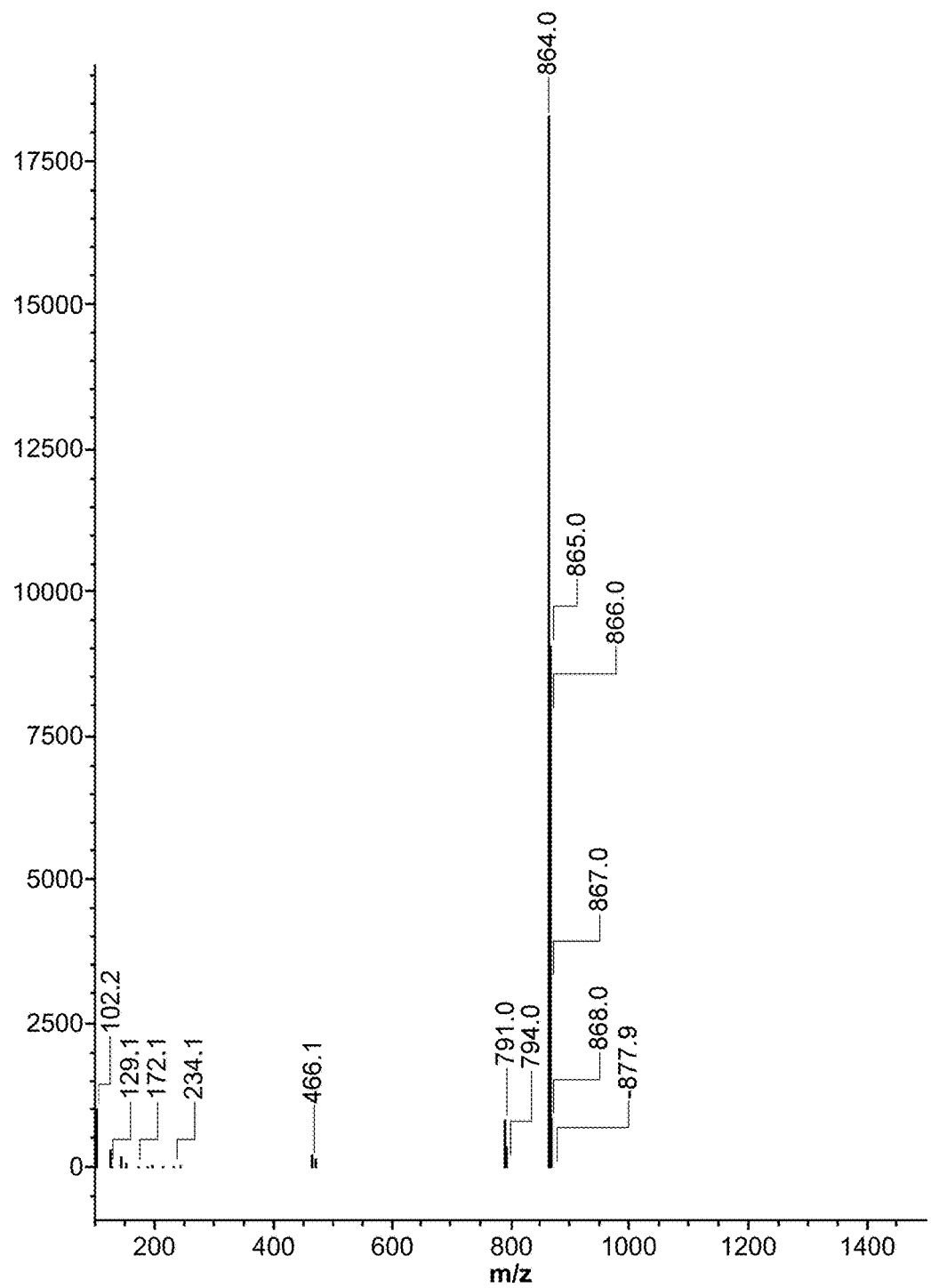
FIG. 27 shows the mass spectrum of meta Cl-N-29-H RA-VII.
Figure 28:
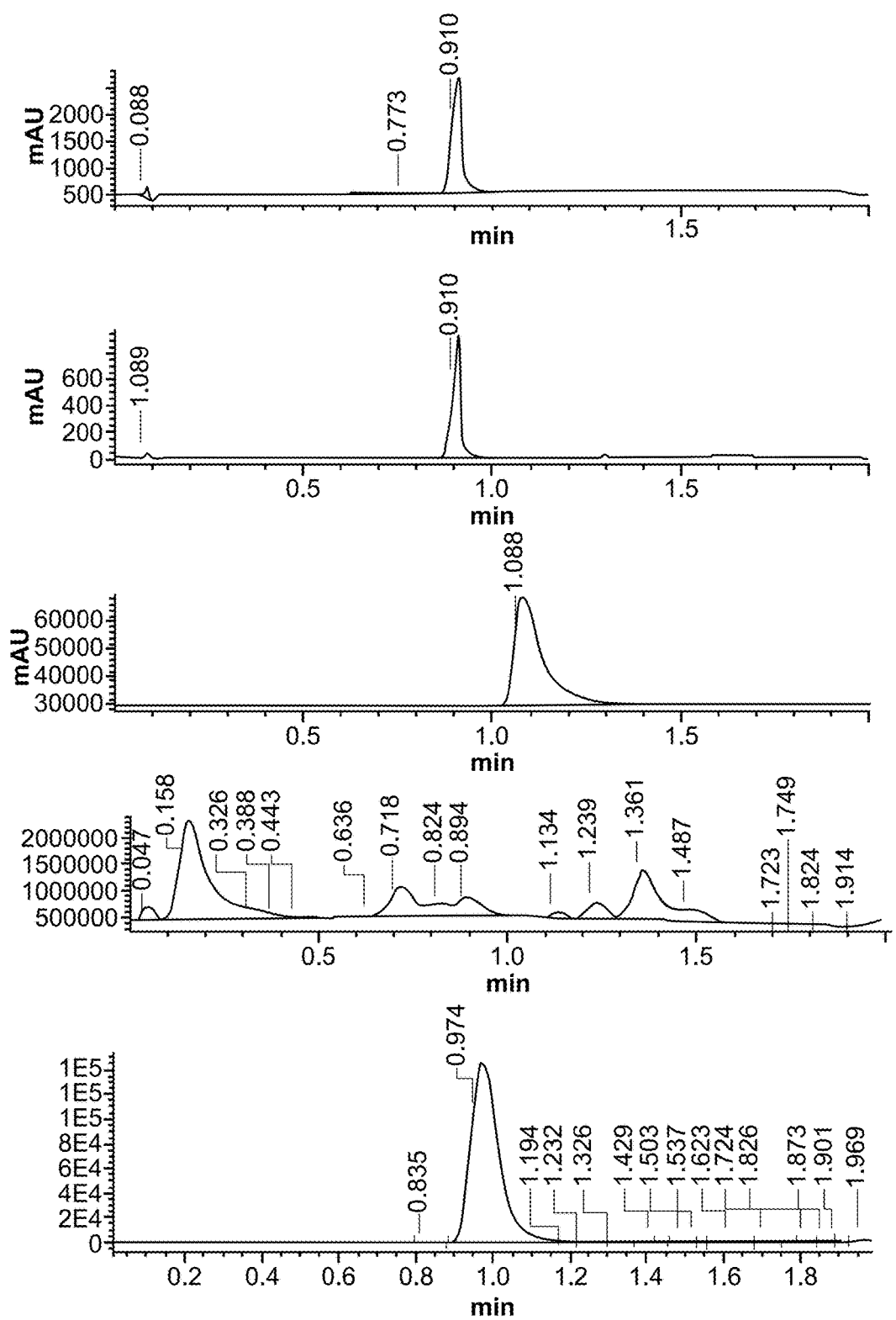
FIG. 28-30 show the LCMS report of meta CN-N-29-H RA-VII.
Figure 29:
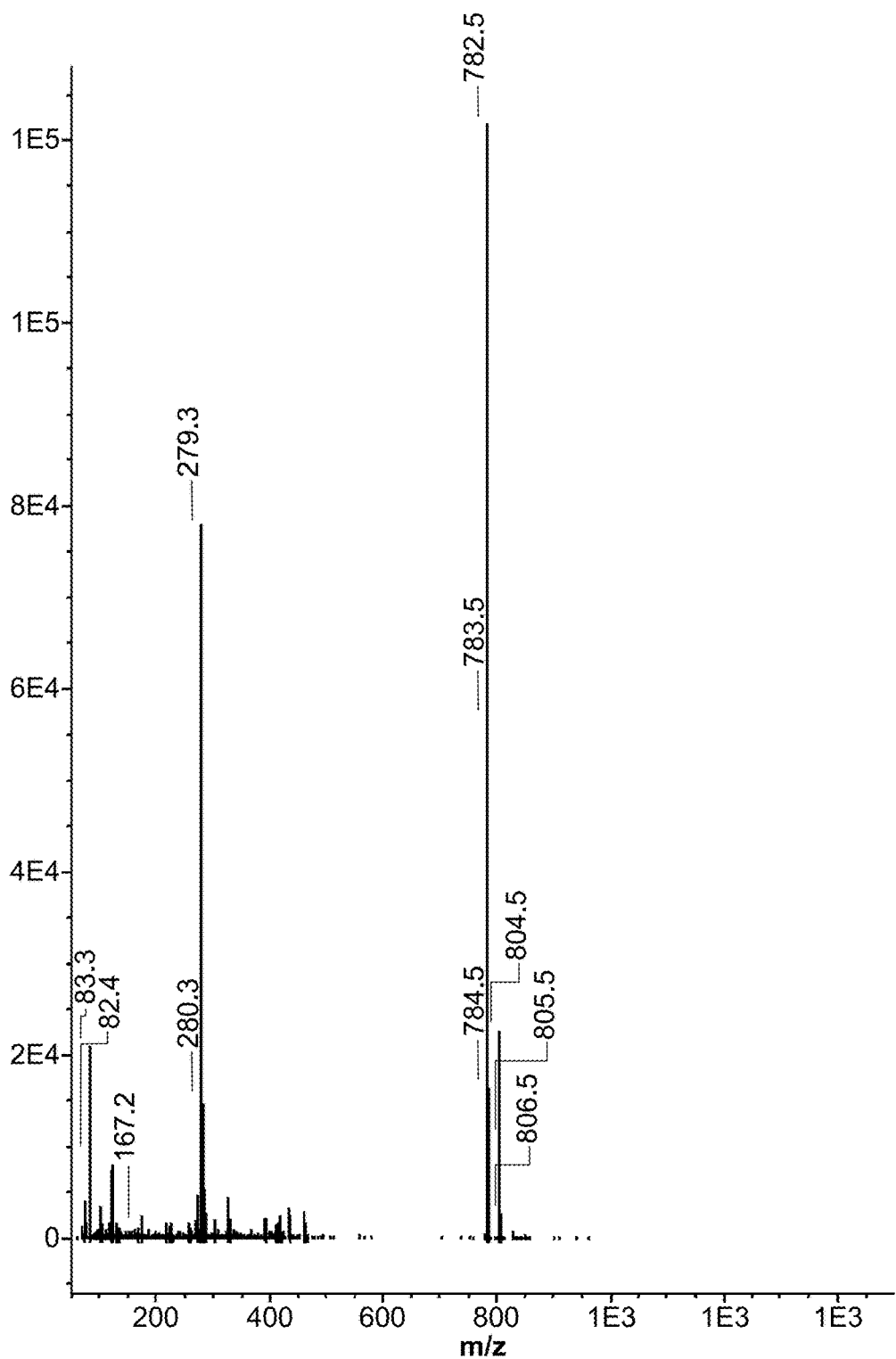
Figure 30:
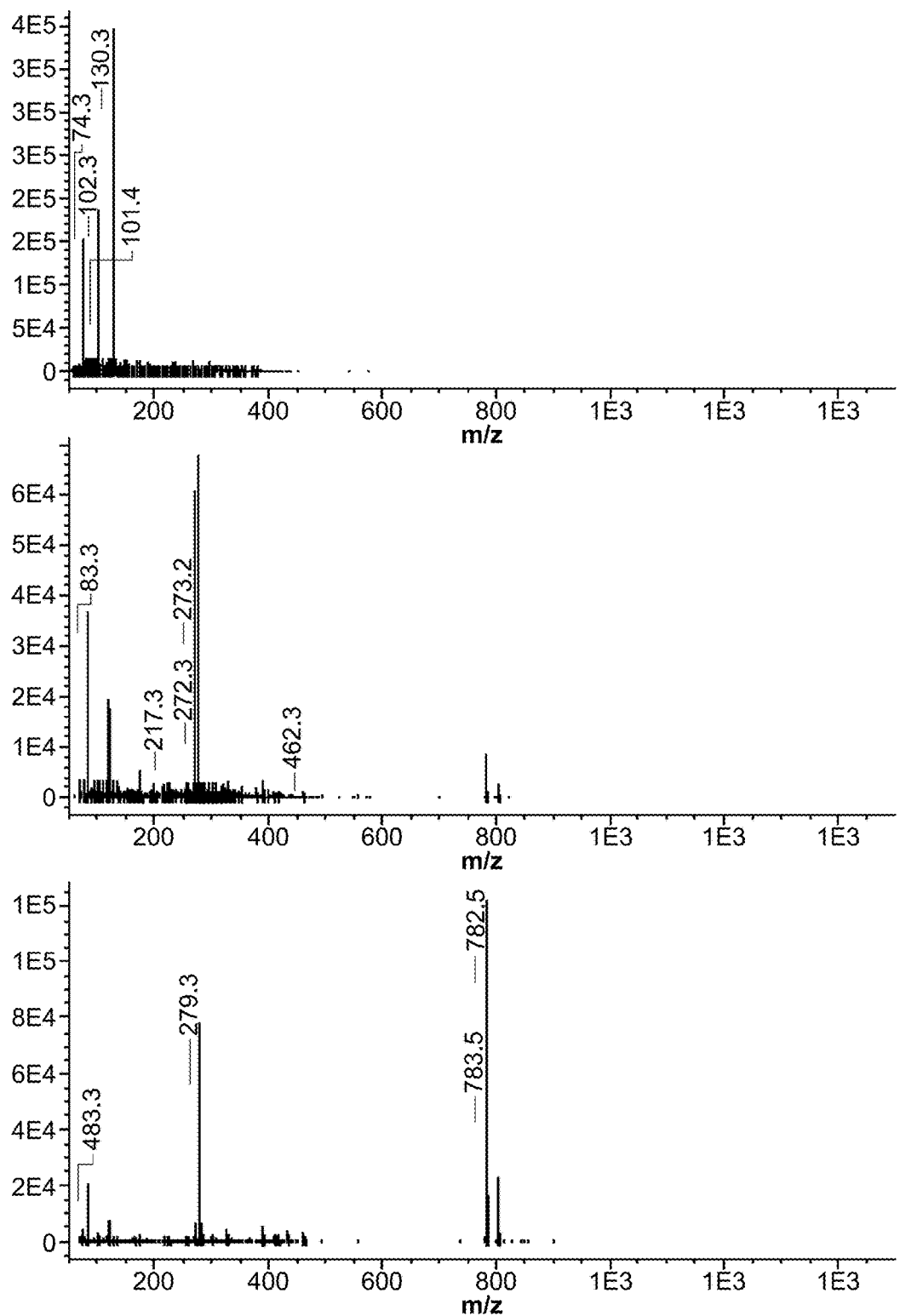
Figure 31:
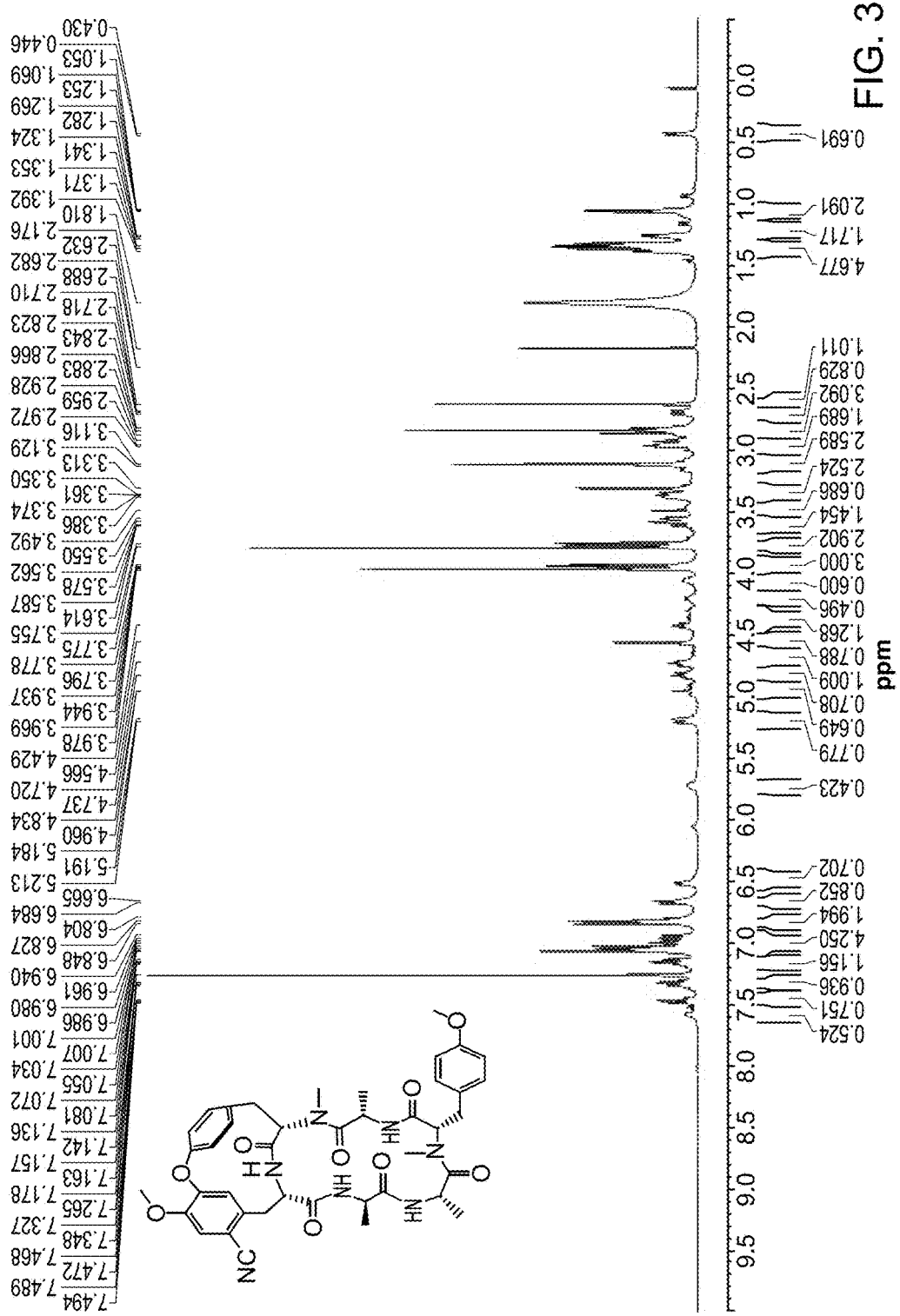
FIG. 31 shows the $^1$H NMR spectrum of meta CN-N-29-H RA-VII.
Figure 32:
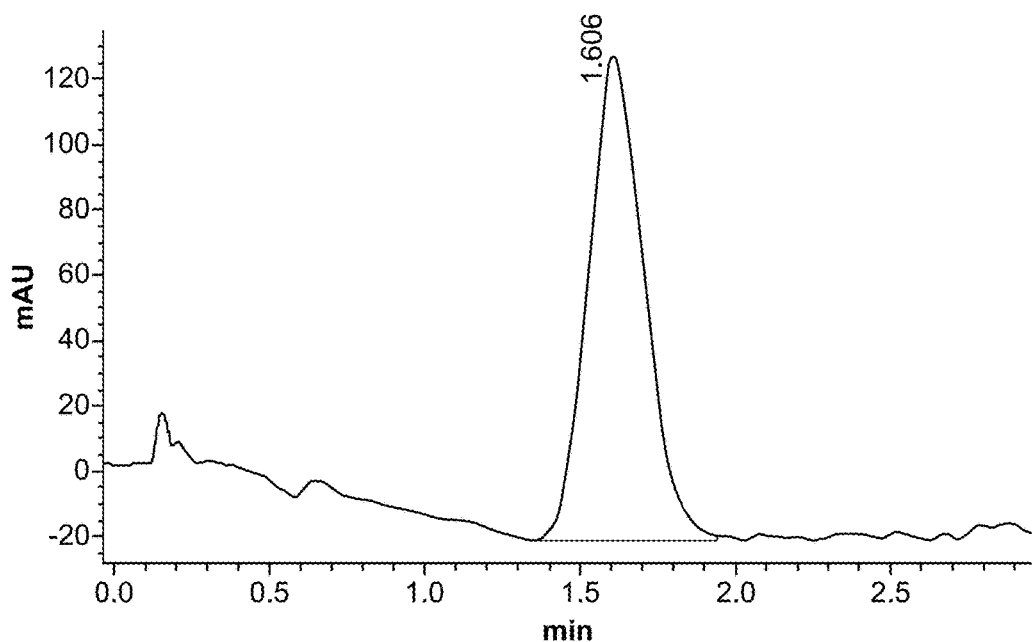
FIG. 32 shows the SFC-MS report of meta CN-N-29-H RA-VII.
Figure 33:
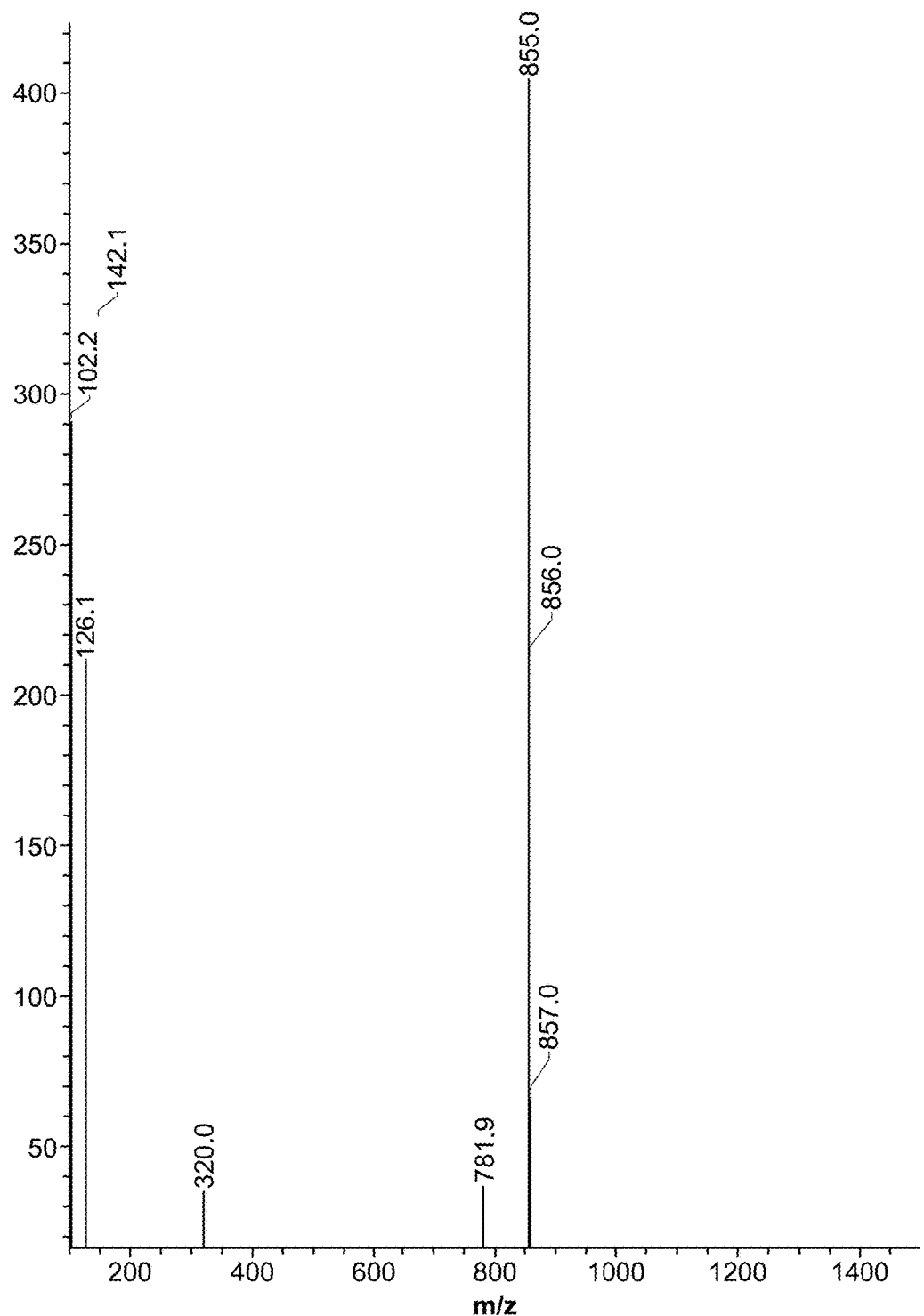
FIG. 33 shows the mass spectrum of meta CN-N-29-H RA-VII.
Figure 34:
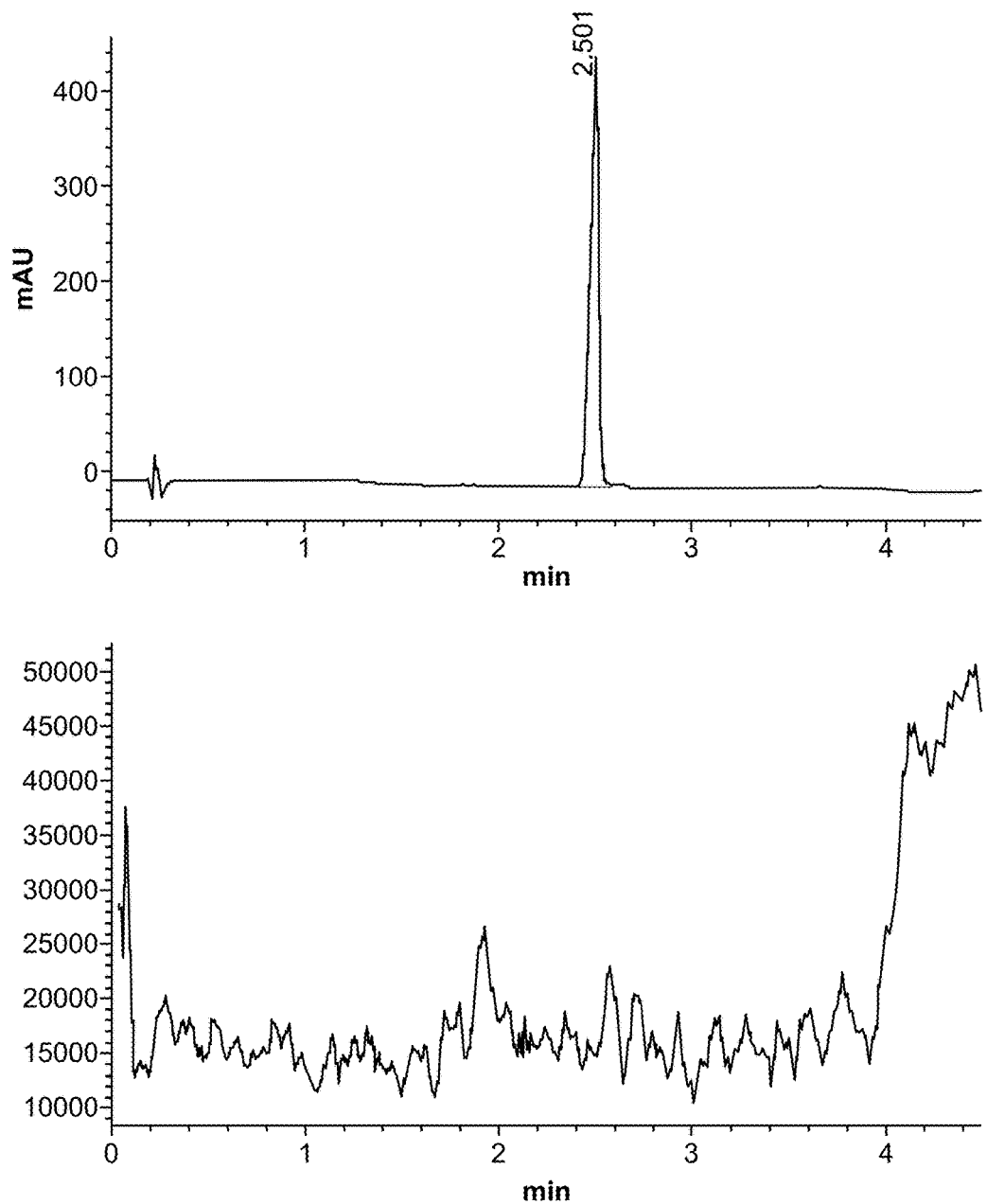
FIG. 34-36 show the LCMS report of N-29-H tyr-F-RA-VII.
Figure 35:
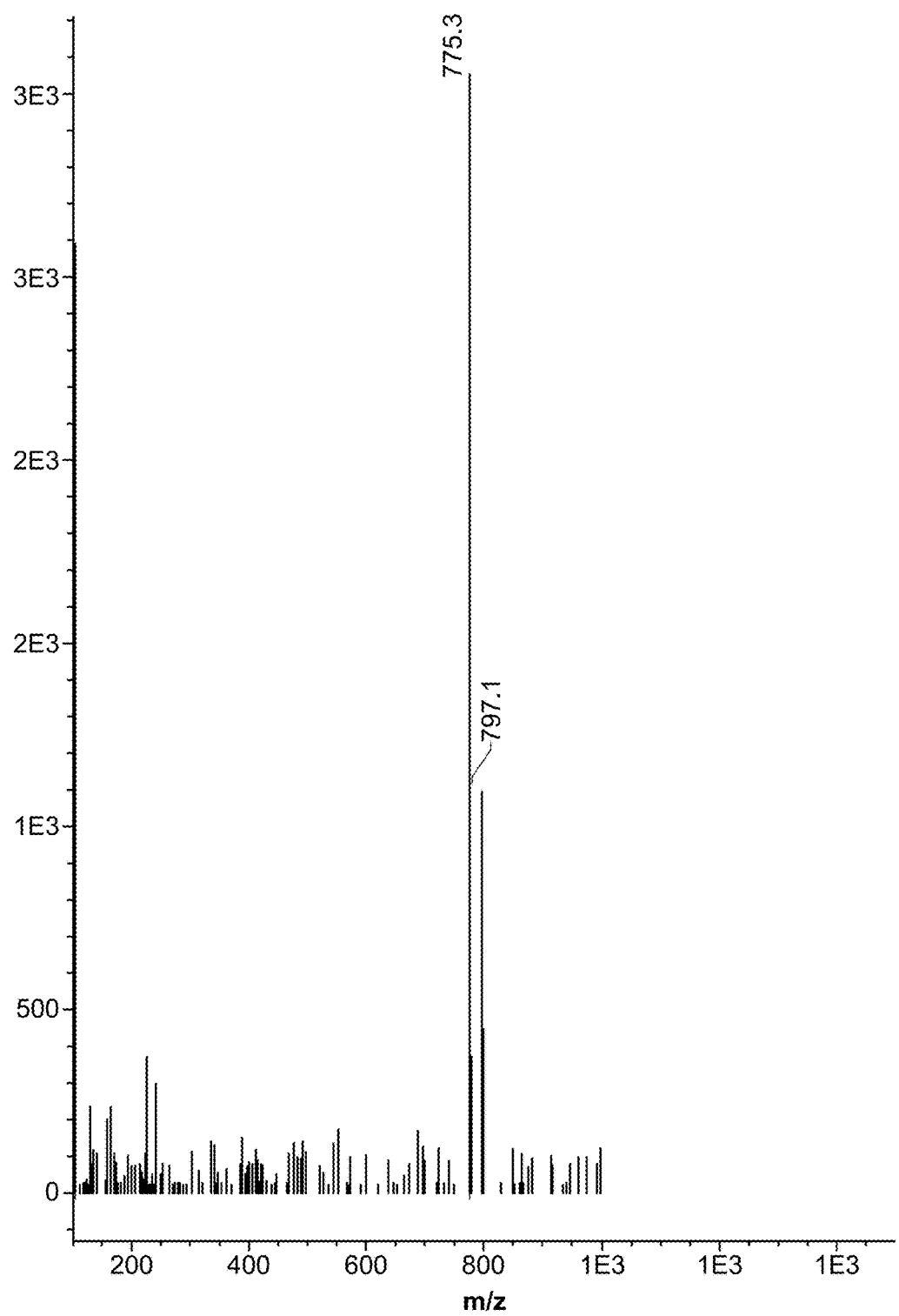
Figure 36:
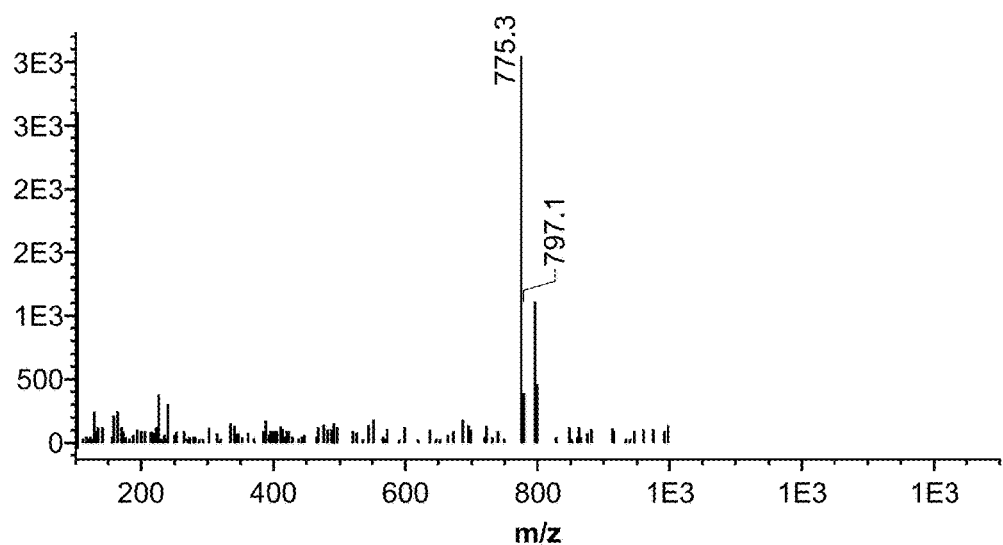
Figure 37:
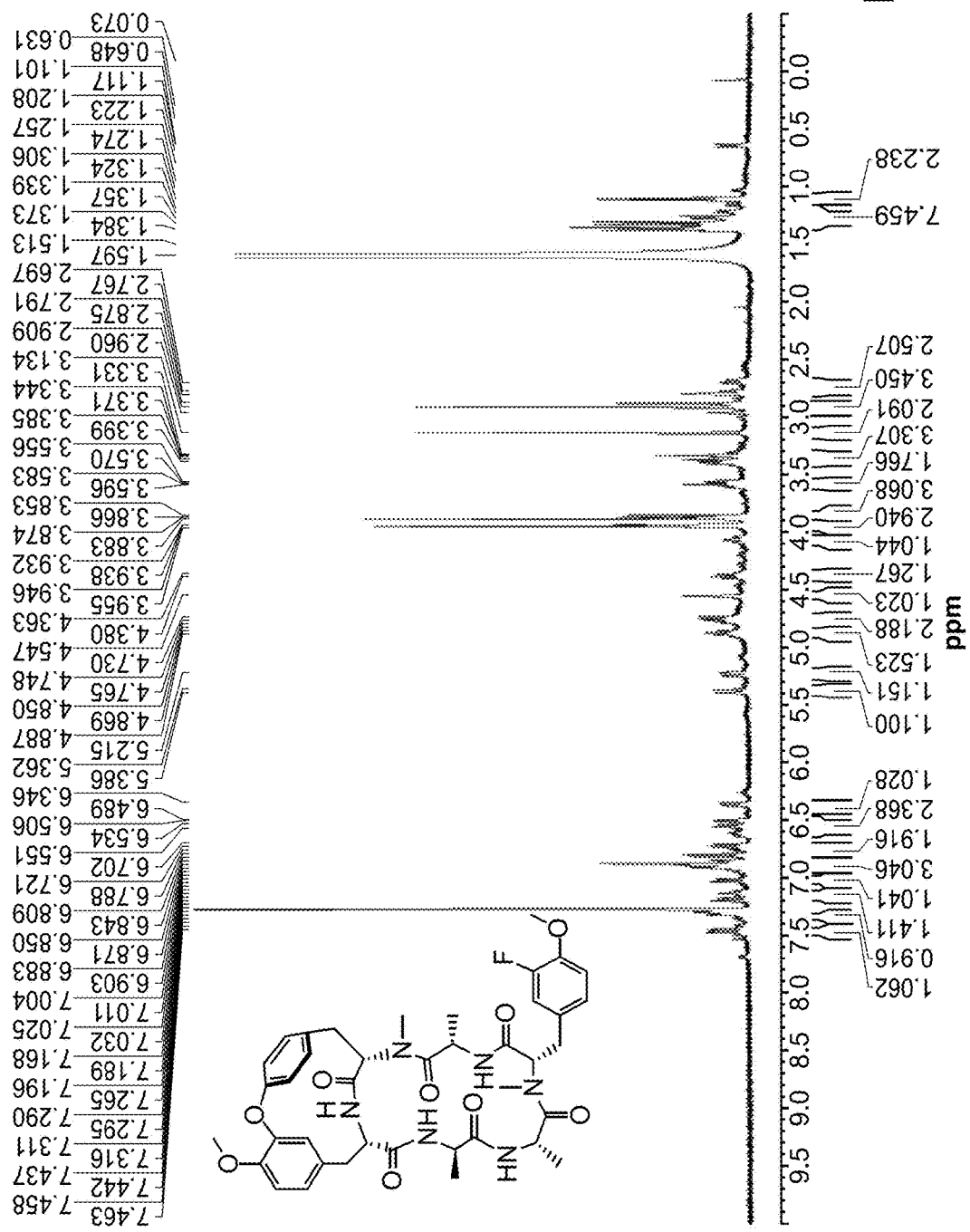
FIG. 37 shows the $^1$H NMR spectrum of N-29-H tyr-F-RA-VII.
Figure 38:
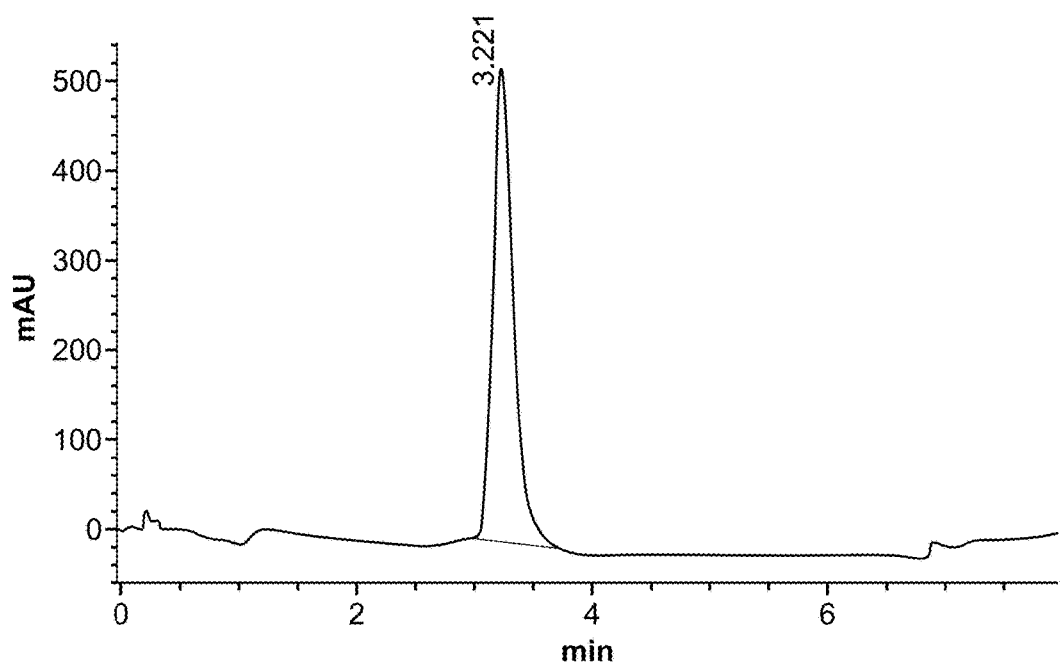
FIG. 38 shows the SFC-MS report of N-29-H tyr-F-RA-VII.
Figure 39:
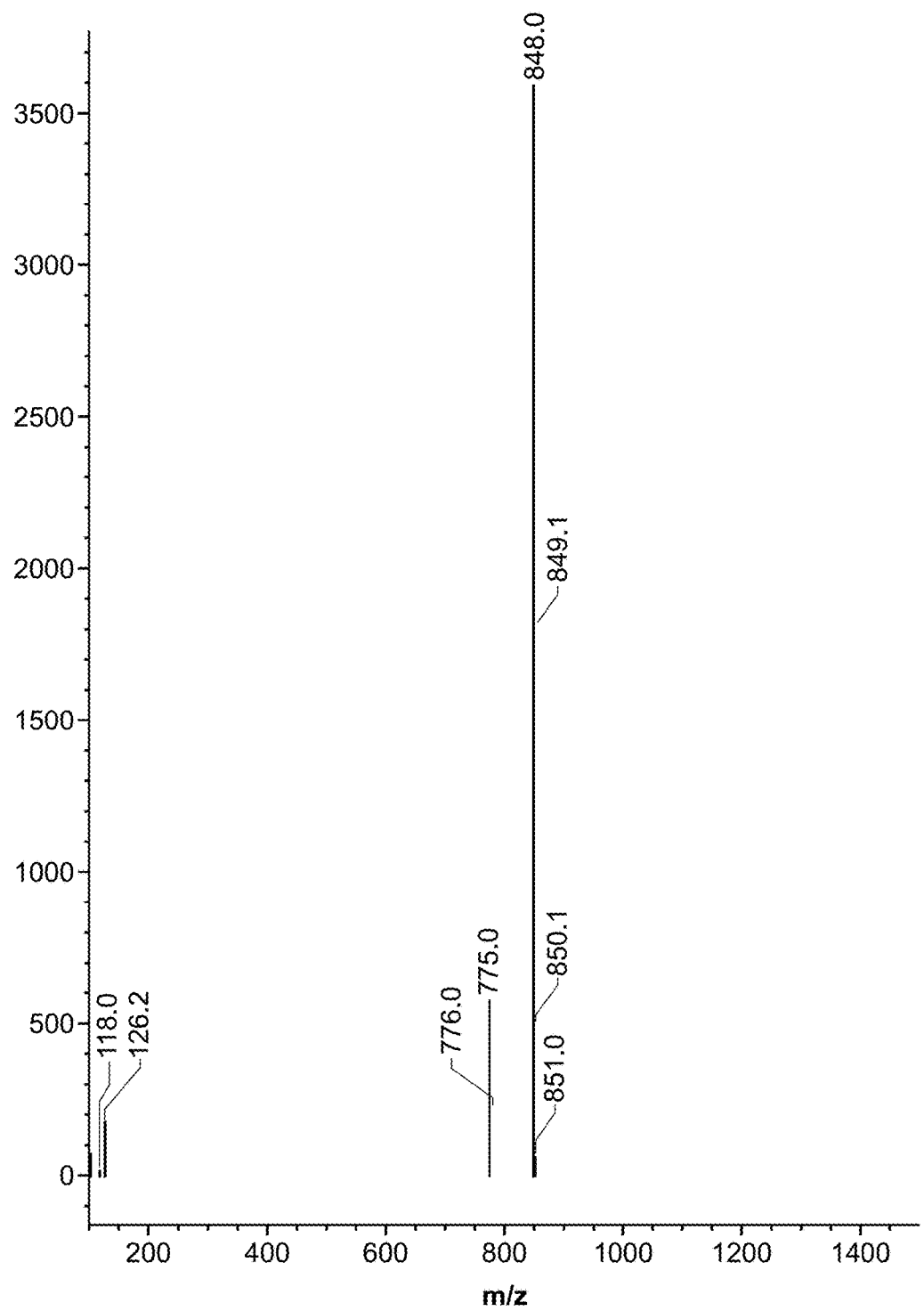
FIG. 39 shows the mass spectrum of N-29-H tyr-F-RA-VII.

FIG. 21 shows that meta Br-N-29-H RA-VII synergizes with the BRAF inhibitor PLX4032 in clonogenic assays. The ability of meta Br-N-29-H RA-VII and PLX4032 to demonstrate synergy in clonogenic assays, which determine the ability of a single cell to form a colony over prolonged exposure to different treatments was tested. HS294T melanoma cells were plated at a low concentration to allow for the formation of single colonies. These cells were then treated with meta Br-N-29-H RA-VII alone, PLX4032 alone and a combination of the two and then processed using the quantitative sulfhorhodamine B assay. When compared to untreated cells, cells treated with 20 nM of meta Br-N-29-H RA-VII show greater than 90% survival. Cells treated with PLX4032 at a concentration of 500 nM show around 60% survival, demonstrating that this cell line is relatively refractory to this BRAF inhibitor. The combination of meta Br-N-29-H RA-VII and PLX4032 showed less than 20% survival, a value much lower than the predicted 50% survival if the two treatments were additive. These data demonstrate that meta Br-N-29-H RA-VII and PLX4032 synergize in clonogenic assays.

FIG. 22 shows that meta Br-N-29-H RA-VII synergizes with inhibitors of BRAF, MEK and P13K/TOR. The combinations of meta Br-N-29-H RA-VII and three commercially available targeted agents (PLX4032 BRAF inhibitor, TAK-333 MEK inhibitor and PF-0491502 P13K/TOR dual inhibitor) were tested at various drug doses. Combination Index values were computed from cell growth assays as previously described (Gladstone et al., Disease Models and Mechanisms, 2012, PMID: 22344740). The tables show average CI values for the combination of meta Br-N-29-H RA-VII and each targeted agent. FA='fraction affected' or fraction of cells killed, reflecting the drug doses used. The CI values that indicate three modes on drug-drug interaction are indicated in the legend and differentially shaded in the table. CI~1 denote additive action (un-shaded). CI>1 denote antagonistic action (darker shade). CI<1 denote synergy (lighter shade). meta Br-N-29-H RA-VII displays synergy with each of the three targeted agents over a range of FA.

While exemplary embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A compound of Formula I, or a pharmaceutically acceptable salt thereof,

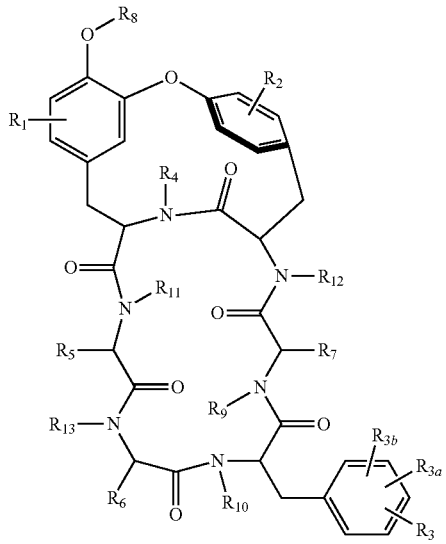

(I)

wherein:
- $R_1$ is selected from a group consisting of: halogen, hydroxyl, $C_{1-8}$ alkyl, $C_{1-8}$ haloalkyl, heteroalkyl, $C_{3-8}$ cycloalkyl, amino, cyano, nitro, aryl, heteroaryl, aminoacyl and acylamino;
- $R_2$, $R_3$, $R_{3a}$ and $R_{3b}$ are independently selected from a group consisting of: hydrogen, halogen, hydroxyl, $C_{1-8}$ alkyl, $C_{1-8}$ haloalkyl, heteroalkyl, $C_{3-8}$ cycloalkyl, amino, cyano, nitro, aryl, heteroaryl, aminoacyl and acylamino;
- $R_4$ is selected from a group consisting of: hydrogen, $C_{2-8}$ alkyl, $C_{1-8}$ haloalkyl, $C_{3-8}$ cycloalkyl, heteroalkyl, aryl and heteroaryl;
- $R_5$, $R_6$ and $R_7$ are independently selected from a group consisting of: hydrogen, $C_{1-8}$ alkyl, $C_{1-8}$ haloalkyl, heteroalkyl, $C_{3-8}$ cycloalkyl, alkyl carboxylic acid, alkylaryl, alkylheteroaryl, aryl and heteroaryl;
- $R_8$, $R_9$, $R_{10}$, $R_{11}$, $R_{12}$ and $R_{13}$ are independently selected from a group consisting of: hydrogen, $C_{1-8}$ alkyl, heteroalkyl, aryl, heteroaryl, $C_{1-8}$ haloalkyl and $C_{3-8}$ cycloalkyl.

2. The compound of claim 1 or its pharmaceutically acceptable salt thereof, wherein at least one of $R_5$, $R_6$, or $R_7$ is independently selected from a group consisting of: hydrogen, $C_{2-8}$ alkyl, $C_{1-8}$ haloalkyl, heteroalkyl, $C_{3-8}$ cycloalkyl, alkyl carboxylic acid, alkylaryl, alkylheteroaryl, aryl and heteroaryl.

3. The compound of claim 2 or its pharmaceutically acceptable salt thereof, wherein at least one of $R_5$, $R_6$, or $R_7$ is hydrogen.

4. The compound of claim 1 or its pharmaceutically acceptable salt thereof, wherein $R_1$ is halogen or cyano.

5. The compound of claim 1 or its pharmaceutically acceptable salt thereof, wherein $R_1$ is bromine.

6. The compound of claim 1 or its pharmaceutically acceptable salt thereof, wherein $R_1$ is cyano.

7. The compound of claim 1 or its pharmaceutically acceptable salt thereof, wherein $R_1$ is chlorine.

8. The compound of claim 1, with the proviso that the compound of Formula I or its pharmaceutically acceptable salt thereof is not

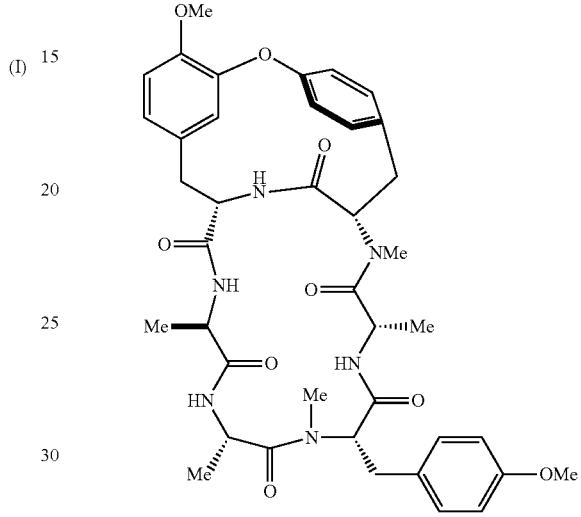

or its pharmaceutically acceptable salt.

9. A method for treating cancer in a subject comprising administering to the subject the compound of claim 1 or a pharmaceutically acceptable salt thereof in a therapeutically effective amount.

10. The method of claim 9, further comprising administering to the subject a therapeutically effective amount of a radiation therapy.

11. The method of claim 9, further comprising administering to the subject a therapeutically effective amount of a chemotherapeutic agent or a pharmaceutically acceptable salt thereof.

12. The method of claim 9, wherein the cancer is selected from a group consisting of: a melanoma, a blood cancer, a head cancer, a neck cancer, a lung cancer, a lymphatic cancer, and a central nervous system cancer.

13. The method of claim 11, wherein the chemotherapeutic agent or the pharmaceutically acceptable salt thereof is selected from a group consisting of: a composition comprising taxane or a pharmaceutically acceptable salt thereof, a composition comprising a platinum-based chemotherapy drug or a pharmaceutically acceptable salt thereof, a composition comprising doxorubicin or a pharmaceutically acceptable salt thereof and any combination thereof.

14. The method of claim 11, wherein the chemotherapeutic agent or pharmaceutically acceptable salt thereof is administered at a concentration of 0.01 to 10 milligrams per kilogram (mg/kg).

15. The method of claim 10, wherein the radiation therapy is given at a dosage of 20 Gray (Gy) to 80 Gy total, fractionated into smaller doses over a course of treatment.

16. A pharmaceutical composition comprising the compound of claim 1 or a pharmaceutically acceptable salt thereof and at least one carrier or diluent.

17. A method of making the pharmaceutical composition of claim 16, wherein the method comprises contacting the compound with the at least one carrier or diluent.

18. The pharmaceutical composition of claim 16, further comprising a chemotherapeutic agent or a pharmaceutically acceptable salt thereof.

19. The pharmaceutical composition of claim 18, wherein the chemotherapeutic agent or the pharmaceutically acceptable salt thereof comprises a taxane or a pharmaceutically acceptable salt thereof, a platinum-based chemotherapy drug or a pharmaceutically acceptable salt thereof, a doxorubicin or a pharmaceutically acceptable salt thereof, or any combination thereof.

20. A kit comprising the compound of claim 1 or a pharmaceutically acceptable salt thereof and instructions for use.

21. A method of making the kit of claim 20, wherein the method comprises placing the instructions for use and the compound or pharmaceutically acceptable salt thereof in a packaging.

22. The method of claim 9, wherein the subject is in need thereof.

23. The method of claim 9, wherein prior to the administering, the subject has been diagnosed with the cancer.

24. The pharmaceutical composition of claim 16, wherein the pharmaceutical composition is in a unit dose form.

* * * * *